US010220142B2

(12) United States Patent
Bechtel et al.

(10) Patent No.: US 10,220,142 B2
(45) Date of Patent: Mar. 5, 2019

(54) REDUCING DISRUPTION DURING MEDICATION ADMINISTRATION

(71) Applicant: CERNER INNOVATION, INC., Kansas City, KS (US)

(72) Inventors: Stephanie Palmer Bechtel, Overland Park, KS (US); Mark Nolte, Lee's Summit, MO (US)

(73) Assignee: Cerner Innovation, Inc., Kansas City, KS (US)

( * ) Notice: Subject to any disclaimer, the term of this patent is extended or adjusted under 35 U.S.C. 154(b) by 1070 days.

(21) Appl. No.: 14/529,432

(22) Filed: Oct. 31, 2014

(65) Prior Publication Data

US 2015/0057635 A1 Feb. 26, 2015

Related U.S. Application Data

(63) Continuation of application No. 13/731,235, filed on Dec. 31, 2012, which is a continuation-in-part of
(Continued)

(51) Int. Cl.
*A61M 5/172* (2006.01)
*A61M 5/142* (2006.01)
(Continued)

(52) U.S. Cl.
CPC .......... *A61M 5/172* (2013.01); *A61B 5/0205* (2013.01); *A61B 5/1113* (2013.01);
(Continued)

(58) Field of Classification Search
CPC .... G06F 19/327; G06F 19/3409; G06F 19/30; G06F 19/3418; G06F 19/3406;
(Continued)

(56) References Cited

U.S. PATENT DOCUMENTS 4,669,263 A 6/1987 Sugiyama
4,857,716 A 8/1989 Gombrich et al.
(Continued)

FOREIGN PATENT DOCUMENTS

DE 19844918 A1 4/2000
WO 2009018422 A1 2/2009
WO 2012122002 A1 9/2012

OTHER PUBLICATIONS

First Action Interview Office Action dated Aug. 8, 2016 in U.S. Appl. No. 13/731,235, 8 pages.
(Continued)

*Primary Examiner* — Boniface Nganga
(74) *Attorney, Agent, or Firm* — Shook, Hardy & Bacon L.L.P.

(57) ABSTRACT

Methods, computer systems, and computer readable media are provided for transitioning a clinical care room from a first scene to a second scene in order to facilitate completion of a medication-administration process. The first scene in the clinical care room is presented where the clinical care room has one or more zones. The first scene is associated with a first group of setting for components within the one or more zones. An input indicating that the medication-administration process has been initiated is received. Incident to receiving the input, the second scene is provided. The second scene is associated with a second group of settings for the components. The second group of settings is optimized to facilitate completion medication-administration process.

19 Claims, 30 Drawing Sheets

Related U.S. Application Data application No. 13/339,828, filed on Dec. 29, 2011, now Pat. No. 8,727,981, which is a continuation-in-part of application No. 13/235,837, filed on Sep. 19, 2011, now Pat. No. 8,655,680, which is a continuation-in-part of application No. 13/164,167, filed on Jun. 20, 2011, now Pat. No. 8,620,682.

(51) Int. Cl.

| | | |
|---|---|---|
| *G09B 5/02* | (2006.01) | |
| *A61G 7/002* | (2006.01) | |
| *A61B 19/00* | (2006.01) | |
| *G08B 21/02* | (2006.01) | |
| *A61B 5/00* | (2006.01) | |
| *A61B 5/0205* | (2006.01) | |
| *A61B 5/11* | (2006.01) | |
| *G08B 21/04* | (2006.01) | |
| *G06F 19/00* | (2018.01) | |
| *G06Q 10/00* | (2012.01) | |
| *G06Q 50/22* | (2018.01) | |
| *A61M 21/02* | (2006.01) | |
| *G06K 9/00* | (2006.01) | |
| *A61B 90/30* | (2016.01) | |
| *G16H 40/63* | (2018.01) | |
| *G16H 10/60* | (2018.01) | |
| *G16H 20/10* | (2018.01) | |
| *G16H 40/67* | (2018.01) | |
| *G16H 70/00* | (2018.01) | |
| *A61B 7/00* | (2006.01) | |
| *A61G 7/00* | (2006.01) | |
| *A61M 21/00* | (2006.01) | |
| *A61M 16/00* | (2006.01) | |

(52) U.S. Cl.
CPC .......... *A61B 5/6889* (2013.01); *A61B 5/7275* (2013.01); *A61B 90/30* (2016.02); *A61G 7/002* (2013.01); *A61M 5/142* (2013.01); *A61M 5/1723* (2013.01); *A61M 21/02* (2013.01); *G06F 19/00* (2013.01); *G06F 19/30* (2013.01); *G06F 19/3418* (2013.01); *G06K 9/00302* (2013.01); *G06Q 10/00* (2013.01); *G06Q 50/22* (2013.01); *G08B 21/02* (2013.01); *G08B 21/043* (2013.01); *G08B 21/0476* (2013.01); *G08B 21/0492* (2013.01); *G09B 5/02* (2013.01); *G16H 10/60* (2018.01); *G16H 20/10* (2018.01); *G16H 40/63* (2018.01); *G16H 40/67* (2018.01); *G16H 70/00* (2018.01); *A61B 5/1115* (2013.01); *A61B 5/1128* (2013.01); *A61B 5/4824* (2013.01); *A61B 5/6891* (2013.01); *A61B 5/743* (2013.01); *A61B 5/7475* (2013.01); *A61B 7/00* (2013.01); *A61B 2562/029* (2013.01); *A61B 2562/0252* (2013.01); *A61G 7/00* (2013.01); *A61M 16/0051* (2013.01); *A61M 16/024* (2017.08); *A61M 2005/14208* (2013.01); *A61M 2021/005* (2013.01); *A61M 2021/0016* (2013.01); *A61M 2021/0027* (2013.01); *A61M 2021/0044* (2013.01); *A61M 2202/0241* (2013.01); *A61M 2205/18* (2013.01); *A61M 2205/3306* (2013.01); *A61M 2205/3334* (2013.01); *A61M 2205/3368* (2013.01); *A61M 2205/3375* (2013.01); *A61M 2205/3553* (2013.01); *A61M 2205/3561* (2013.01); *A61M 2205/3584* (2013.01); *A61M 2205/3592* (2013.01); *A61M 2205/505* (2013.01); *A61M 2205/52* (2013.01); *A61M 2205/581* (2013.01); *A61M 2205/582* (2013.01); *A61M 2205/583* (2013.01); *A61M 2205/6018* (2013.01); *A61M 2205/6054* (2013.01); *A61M 2205/6072* (2013.01); *A61M 2205/80* (2013.01); *A61M 2210/12* (2013.01); *A61M 2230/06* (2013.01); *A61M 2230/42* (2013.01); *A61M 2230/62* (2013.01); *A61M 2230/63* (2013.01)

(58) Field of Classification Search
CPC .............. G06F 19/3412; G08B 21/043; G08B 21/0476; G08B 21/22; G08B 21/02; A61M 2205/6054; A61M 2205/3584; A61M 2205/3561; A61M 2205/3553; A61M 2205/3375; A61M 2205/3368; A61M 2205/582; A61M 2205/18; A61M 2205/583; A61M 2205/6018; A61M 2205/52; A61M 2205/6072; A61M 2205/581; A61M 2205/505; A61M 2205/3592; A61M 5/1723; A61M 5/142; A61M 5/172; A61M 2005/14208; A61B 90/30; A61B 5/6889; A61B 5/0205; A61B 5/1113; A61G 7/002; G09B 5/02; G06K 9/0032
USPC .................................................... 604/65–67
See application file for complete search history.

(56) References Cited

U.S. PATENT DOCUMENTS

| | | |
|---|---|---|
| 5,031,228 A | 7/1991 | Lu |
| 5,448,221 A | 9/1995 | Weller |
| 5,482,050 A | 1/1996 | Smokoff et al. |
| 5,592,153 A | 1/1997 | Welling et al. |
| 5,798,798 A | 8/1998 | Rector et al. |
| 5,838,223 A | 11/1998 | Gallant et al. |
| 5,915,379 A | 6/1999 | Wallace et al. |
| 5,942,986 A | 8/1999 | Shabot et al. |
| 6,050,940 A | 4/2000 | Braun et al. |
| 6,095,984 A | 8/2000 | Amano et al. |
| 6,160,478 A | 12/2000 | Jacobsen et al. |
| 6,174,283 B1 | 1/2001 | Nevo et al. |
| 6,188,407 B1 | 2/2001 | Smith et al. |
| 6,269,812 B1 | 8/2001 | Wallace et al. |
| 6,287,452 B1 | 9/2001 | Allen et al. |
| 6,322,502 B1 | 11/2001 | Schoenberg et al. |
| 6,369,838 B1 | 4/2002 | Wallace et al. |
| 6,429,869 B1 | 8/2002 | Kamakura et al. |
| 6,614,349 B1 | 9/2003 | Proctor et al. |
| 6,727,818 B1 | 4/2004 | Wildman et al. |
| 6,804,656 B1 | 10/2004 | Rosenfeld et al. |
| 7,015,816 B2 | 3/2006 | Wildman et al. |
| 7,122,005 B2 | 10/2006 | Shusterman |
| 7,154,397 B2 | 12/2006 | Lerhusen et al. |
| 7,237,287 B2 | 7/2007 | Weismiller et al. |
| 7,323,991 B1 | 1/2008 | Eckert et al. |
| 7,408,470 B2 | 8/2008 | Wildman et al. |
| 7,420,472 B2 | 9/2008 | Tran |
| 7,430,608 B2 | 9/2008 | Noonan et al. |
| 7,612,679 B1 | 11/2009 | Fackler et al. |
| 7,669,263 B2 | 3/2010 | Menkedick et al. |
| 7,715,387 B2 | 5/2010 | Schuman |
| 7,724,147 B2 | 5/2010 | Brown |
| 7,756,723 B2 | 7/2010 | Rosow et al. |
| 7,890,349 B2 | 2/2011 | Cole et al. |
| 7,895,055 B2 | 2/2011 | Schneider et al. |
| 7,908,153 B2 | 3/2011 | Scherpbier et al. |
| 7,945,457 B2 | 5/2011 | Zaleski |
| 7,962,544 B2 | 6/2011 | Torok et al. |
| 7,972,140 B2 | 7/2011 | Renaud |
| 8,123,685 B2 | 2/2012 | Brauers et al. |
| 8,237,558 B2 | 8/2012 | Seyed Momen et al. |
| 8,273,018 B1 | 9/2012 | Fackler et al. |

(56) References Cited

U.S. PATENT DOCUMENTS

| | | |
|---|---|---|
| 8,432,263 B2 | 4/2013 | Kunz |
| 8,451,314 B1 | 5/2013 | Cline et al. |
| 8,529,448 B2 | 9/2013 | McNair |
| 8,565,500 B2 | 10/2013 | Neff |
| 8,620,682 B2 | 12/2013 | Bechtel et al. |
| 8,655,680 B2 | 2/2014 | Bechtel et al. |
| 8,700,423 B2 | 4/2014 | Eaton, Jr. et al. |
| 8,727,981 B2 | 5/2014 | Bechtel et al. |
| 8,769,153 B2 | 7/2014 | Dziubinski |
| 8,890,937 B2 | 11/2014 | Skubic et al. |
| 8,902,068 B2 | 12/2014 | Bechtel et al. |
| 9,072,929 B1 | 7/2015 | Rush et al. |
| 9,129,506 B1 | 9/2015 | Kusens |
| 9,147,334 B2 | 9/2015 | Long et al. |
| 9,159,215 B1 | 10/2015 | Kusens |
| 9,305,191 B2 | 4/2016 | Long et al. |
| 9,408,561 B2 | 8/2016 | Stone et al. |
| 9,489,820 B1 | 11/2016 | Kusens |
| 9,519,969 B1 | 12/2016 | Kusens |
| 9,536,310 B1 | 1/2017 | Kusens |
| 9,538,158 B1 | 1/2017 | Rush et al. |
| 9,597,016 B2 | 3/2017 | Stone et al. |
| 9,729,833 B1 | 8/2017 | Kusens |
| 9,741,227 B1 | 8/2017 | Kusens |
| 9,892,310 B2 | 2/2018 | Kusens et al. |
| 9,892,311 B2 | 2/2018 | Kusens et al. |
| 9,892,611 B1 | 2/2018 | Kusens |
| 9,905,113 B2 | 2/2018 | Kusens |
| 2002/0015034 A1 | 2/2002 | Malmborg |
| 2002/0077863 A1 | 6/2002 | Rutledge et al. |
| 2002/0101349 A1 | 8/2002 | Rojas, Jr. |
| 2002/0115905 A1 | 8/2002 | August |
| 2002/0183976 A1 | 12/2002 | Pearce |
| 2003/0037786 A1 | 2/2003 | Biondi et al. |
| 2003/0070177 A1 | 4/2003 | Kondo et al. |
| 2003/0092974 A1 | 5/2003 | Santoso et al. |
| 2003/0095147 A1 | 5/2003 | Daw |
| 2003/0135390 A1 | 7/2003 | O'Brien et al. |
| 2003/0140928 A1 | 7/2003 | Bui et al. |
| 2003/0227386 A1 | 12/2003 | Pulkkinen et al. |
| 2004/0019900 A1 | 1/2004 | Knightbridge et al. |
| 2004/0052418 A1 | 3/2004 | DeLean |
| 2004/0054760 A1 | 3/2004 | Ewing et al. |
| 2004/0097227 A1 | 5/2004 | Siegel |
| 2004/0116804 A1 | 6/2004 | Mostafavi |
| 2004/0193449 A1 | 9/2004 | Wildman et al. |
| 2005/0038326 A1 | 2/2005 | Mathur |
| 2005/0182305 A1 | 8/2005 | Hendrich |
| 2005/0231341 A1 | 10/2005 | Shimizu |
| 2005/0249139 A1 | 11/2005 | Nesbit |
| 2006/0004606 A1 | 1/2006 | Wendl et al. |
| 2006/0047538 A1 | 3/2006 | Condurso et al. |
| 2006/0049936 A1 | 3/2006 | Collins et al. |
| 2006/0058587 A1 | 3/2006 | Heimbrock et al. |
| 2006/0089541 A1 | 4/2006 | Braun et al. |
| 2006/0092043 A1 | 5/2006 | Lagassey |
| 2006/0107295 A1 | 5/2006 | Margis et al. |
| 2006/0145874 A1 | 7/2006 | Fredriksson et al. |
| 2006/0261974 A1 | 11/2006 | Albert et al. |
| 2007/0085690 A1 | 4/2007 | Tran |
| 2007/0118054 A1 | 5/2007 | Pinhas et al. |
| 2007/0120689 A1 | 5/2007 | Zerhusen et al. |
| 2007/0129983 A1 | 6/2007 | Scherpbier et al. |
| 2007/0136218 A1 | 6/2007 | Bauer et al. |
| 2007/0279219 A1 | 12/2007 | Warriner |
| 2007/0296600 A1 | 12/2007 | Dixon et al. |
| 2008/0001763 A1 | 1/2008 | Raja et al. |
| 2008/0002860 A1 | 1/2008 | Super et al. |
| 2008/0004904 A1 | 1/2008 | Tran |
| 2008/0009686 A1 | 1/2008 | Hendrich |
| 2008/0015903 A1 | 1/2008 | Rodgers |
| 2008/0071210 A1* | 3/2008 | Moubayed ............ A61M 5/172 604/67 |
| 2008/0087719 A1 | 4/2008 | Sahud |
| 2008/0106374 A1 | 5/2008 | Sharbaugh |
| 2008/0126132 A1* | 5/2008 | Warner ................ A61B 5/0002 705/3 |
| 2008/0228045 A1* | 9/2008 | Gao ..................... A61B 5/0024 600/301 |
| 2008/0249376 A1 | 10/2008 | Zaleski |
| 2008/0267447 A1 | 10/2008 | Kelusky et al. |
| 2008/0277486 A1 | 11/2008 | Seem et al. |
| 2008/0281638 A1 | 11/2008 | Weatherly et al. |
| 2009/0082829 A1 | 3/2009 | Panken et al. |
| 2009/0091458 A1 | 4/2009 | Deutsch |
| 2009/0099480 A1 | 4/2009 | Salgo et al. |
| 2009/0112630 A1 | 4/2009 | Collins, Jr. et al. |
| 2009/0119843 A1 | 5/2009 | Rodgers et al. |
| 2009/0177327 A1 | 7/2009 | Turner |
| 2009/0224924 A1 | 9/2009 | Thorp |
| 2009/0278934 A1 | 11/2009 | Ecker et al. |
| 2009/0322513 A1 | 12/2009 | Hwang et al. |
| 2010/0117836 A1 | 5/2010 | Seyed Momen et al. |
| 2010/0169114 A1 | 7/2010 | Henderson et al. |
| 2010/0169120 A1 | 7/2010 | Herbst et al. |
| 2010/0176952 A1 | 7/2010 | Bajcsy et al. |
| 2010/0188228 A1 | 7/2010 | Hyland |
| 2010/0205771 A1 | 8/2010 | Pietryga et al. |
| 2010/0245577 A1 | 9/2010 | Yamamoto et al. |
| 2010/0285771 A1 | 11/2010 | Peabody |
| 2010/0305466 A1 | 12/2010 | Corn |
| 2011/0018709 A1 | 1/2011 | Kornbluh |
| 2011/0022981 A1 | 1/2011 | Mahajan et al. |
| 2011/0025493 A1 | 2/2011 | Papadopoulos et al. |
| 2011/0025499 A1 | 2/2011 | Hoy et al. |
| 2011/0035057 A1 | 2/2011 | Receveur et al. |
| 2011/0035466 A1 | 2/2011 | Panigrahi |
| 2011/0054936 A1 | 3/2011 | Cowan et al. |
| 2011/0068930 A1 | 3/2011 | Wildman et al. |
| 2011/0077965 A1 | 3/2011 | Nolte et al. |
| 2011/0087079 A1 | 4/2011 | Aarts |
| 2011/0102133 A1 | 5/2011 | Shaffer |
| 2011/0102181 A1 | 5/2011 | Metz et al. |
| 2011/0106560 A1 | 5/2011 | Eaton, Jr. et al. |
| 2011/0106561 A1 | 5/2011 | Eaton, Jr. et al. |
| 2011/0175809 A1 | 7/2011 | Markovic et al. |
| 2011/0190593 A1 | 8/2011 | McNair |
| 2011/0227740 A1 | 9/2011 | Wohltjen |
| 2011/0254682 A1 | 10/2011 | Sigrist Christensen |
| 2011/0288811 A1 | 11/2011 | Greene |
| 2011/0295621 A1 | 12/2011 | Farooq et al. |
| 2011/0301440 A1 | 12/2011 | Riley et al. |
| 2011/0313325 A1 | 12/2011 | Cuddihy |
| 2012/0025991 A1 | 2/2012 | O'Keefe et al. |
| 2012/0026308 A1 | 2/2012 | Johnson et al. |
| 2012/0075464 A1 | 3/2012 | Derenne et al. |
| 2012/0092162 A1 | 4/2012 | Rosenberg |
| 2012/0098918 A1 | 4/2012 | Murphy |
| 2012/0154582 A1 | 6/2012 | Johnson et al. |
| 2012/0212582 A1 | 8/2012 | Deutsch |
| 2012/0259650 A1 | 10/2012 | Mallon et al. |
| 2013/0027199 A1 | 1/2013 | Bonner |
| 2013/0120120 A1 | 5/2013 | Long et al. |
| 2013/0122807 A1 | 5/2013 | Tenarvitz et al. |
| 2013/0184592 A1 | 7/2013 | Venetianer et al. |
| 2013/0309128 A1 | 11/2013 | Voegeli et al. |
| 2013/0332184 A1 | 12/2013 | Burnham et al. |
| 2014/0039351 A1 | 2/2014 | Mix et al. |
| 2014/0070950 A1 | 3/2014 | Snodgrass |
| 2014/0085501 A1 | 3/2014 | Tran |
| 2014/0191861 A1 | 7/2014 | Scherrer |
| 2014/0327545 A1 | 11/2014 | Bolling et al. |
| 2016/0093195 A1 | 3/2016 | Ophardt |
| 2017/0143240 A1 | 5/2017 | Stone et al. |

OTHER PUBLICATIONS

Final Office Action dated Apr. 14, 2017 in U.S. Appl. No. 13/731,235, 15 pages.
First Action Interview Preinterview Communication dated Jun. 30, 2017 in U.S. Appl. No. 14/088,923, 5 pages.
First Action Interview Office Action dated Aug. 25, 2017 in U.S. Appl. No. 14/088,923, 8 pages.

(56) References Cited

OTHER PUBLICATIONS

Non-Final Office Action dated Sep. 27, 2017 in U.S. Appl. No. 13/731,235, 18 pages.
First Action Interview Pre-Interview Communication dated Sep. 28, 2017 in U.S. Appl. No. 14/244,160, 4 pages.
First Action Interview Office Action dated Nov. 28, 2017 in U.S. Appl. No. 14/244,160, 3 pages.
Tom Mooney, "Rhode Island ER first to test Google Glass on medical conditions", http://www.ems1.com/ems-products/cameras-video/articles/1860487-Rhode-Island-ER-first . . . printed on Mar. 11, 2014.
Raheja, et al., "Human Facial Expression Detection From Detected in CapturedImage Using Back Propagation Neural Network", International Journal of Computer Science and Information Technology (IJCSIT), vol. 2, No. 1, Feb. 2010, 8 pages.
Virtual Patient Observation: Centralize Monitoring of High-Risk Patients with Video-Cisco Video Surveillance Manager, https://www.cisco.com/c/en/us/products/collateral/physical-security/video-surveillance-manager/white paper_C11-715263.pdf.
First Action Interview Preinterview Communication dated Apr. 7, 2016 in U.S. Appl. No. 13/731,235, 4 pages.
Final Office Action dated Apr. 18, 2018 in U.S. Appl. No. 13/731,235, 15 pages.
Notice of Allowance dated May 29, 2018 in U.S. Appl. No. 14/244,160, 8 pages.

* cited by examiner

FIG. 7B.

*(Screen capture of patient monitoring interface)*

Menu bar: FILE | EDIT | ACTIONS | VIEW | REFERENCE | HELP

Tabs (702): PATIENT SEARCH | ICU SUMMARY | MED REVIEW | 24 HOUR HEMO | 7 DAY I&O | RAPID VIEW SCHMITT, EUGENE  84 YEARS M  DOB: 8/19/1926  MRN: 33146723  FIN: 237698  LOCATION: 2 EAST 2153
DOSE WEIGHT: 70 KG (10/10/2010 1536)  ACTUAL WEIGHT: 73.2KG (10/10/2010 1121)  ALLERGIES: REGLAN, IODINE

RAPID VIEW (708)

- HR 101  LEAD II
- LEAD AVR

*(ECG waveform traces)*

Timeline axis: 11:35 · 11:40 · 11:45 · 11:50 · 11:55 · 12:00 · 12:05 · 12:10 · 12:15

Event markers (710):
- V-TACH (PULSELESS)
- CODE TEAM PAGED
- BEGIN CPR
- AIRWAY
- 200J 300J 360J
- RN RONA B. MANSON
- RN CHRISTINE
- DR. BLACK
- RT SARAH
- CODING BEGINS

CODE DURATION 0:10:05
CURRENT 12:10:05 PM

PATIENT SUMMARY (704)

| | |
|---|---|
| PATIENT HISTORY: | CORONARY ARTERY DISEASE |
| PROCEDURE HISTORY: | CARDIAC CATHETERIZATION (2004) |
| SURGICAL HISTORY: | (NONE) |
| ADMITTING DIAGNOSIS: | CARDIAC ARREST |
| ATTENDING MD: | DR. GRANT BLACK |

PROTOCOL: VTACH PULSELESS (706)

- CODE TEAM PAGED ———— 12:01 >
- BEGIN CPR ———————— 12:03 >
- AIRWAY ————————— 12:04 >
- DEFIBRILLATE 200J ——— 12:05 >
- VASOPRESSIN 40 UNITS — 12:07 >
- DEFIBRILLATE 300J ——— 12:07 >
- DEFIBRILLATE 360J ——— 12:09 >

LAB RESULTS (712)

ABG (10/10/10...
| | |
|---|---|
| PH: 7.30 | PCO2: 48 |
| PO2: 92 | HCO3: 18 |

FIG. 7C.

REDUCING DISRUPTION DURING MEDICATION ADMINISTRATION

CROSS REFERENCE TO RELATED APPLICATIONS

This application, having attorney docket number CRNI.220710, is a Continuation application of copending U.S. patent application Ser. No. 13/731,235, filed Dec. 31, 2012, entitled "Management of Patient Fall Risk;" which is a Continuation-In-Part Application of U.S. Pat. No. 8,727, 981 (U.S. patent application Ser. No. 13/339,828), filed Dec. 29, 2011, issued May 20, 2014, entitled "Ambient Sensing of Patient Discomfort;" which is a Continuation-in-Part Application of U.S. Pat. No. 8,655,680 (U.S. application. Ser. No. 13/235,837), filed Sep. 19, 2011, issued Feb. 18, 2014, entitled "Minimizing Disruption During Medication Administration;" which is a Continuation-in-Part Application of U.S. Pat. No. 8,620,682 (US application Ser. No. 13/164,167), filed Jun. 20, 2011, issued Dec. 21, 2013, entitled "Smart Clinical Care Room." The aforementioned applications are incorporated by reference herein.

BACKGROUND

The prevention and reduction of patient falls are important concerns in a healthcare facility. Traditional ways of reducing the number of patient falls include identifying patients who are at risk for falls and attempting to prevent falls for this patient group by ordering that bed guard rails be placed in an upright position at all times. However, some patients can easily lower the guard rails and attempt to leave the bed without assistance. Further, current nursing demands make it infeasible for nurses to continuously monitor this patient group. The result is that patient falls continue to be a problem at many healthcare facilities.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter. The present invention is defined by the claims.

Embodiments of the present invention are directed to methods, computer systems, and computer storage media for managing fall risk for a patient in a clinical care room. Patients that have been classified as being a fall risk are automatically monitored through fall risk sensors located throughout the patient's clinical care room. The fall risk sensors include weight sensors and guard rail sensors associated with the patient's bed as well as location sensors that can determine the location and/or position of the patient within the clinical care room. Inputs from the fall risk sensors are utilized to determine if the patient is currently at risk for falling. If the patient is at risk for falling, alerts are initiated and settings in the clinical care room are modified to help decrease the patient's fall risk. For instance, an alert may be communicated to members of the patient's care team and a message may be presented on a display device in the patient's room informing the patient to stay in bed and that a caregiver will arrive shortly to assist the patient. These measures reduce the number of patient falls which, in turn, leads to improved patient safety and well-being.

BRIEF DESCRIPTION OF THE DRAWINGS

Embodiments are described in detail below with reference to the attached drawing figures, wherein:

FIGS. 7A-7C depict exemplary graphical user interfaces generated by a clinician dashboard component suitable to implement embodiments of the present invention;

DETAILED DESCRIPTION

Figure 1:
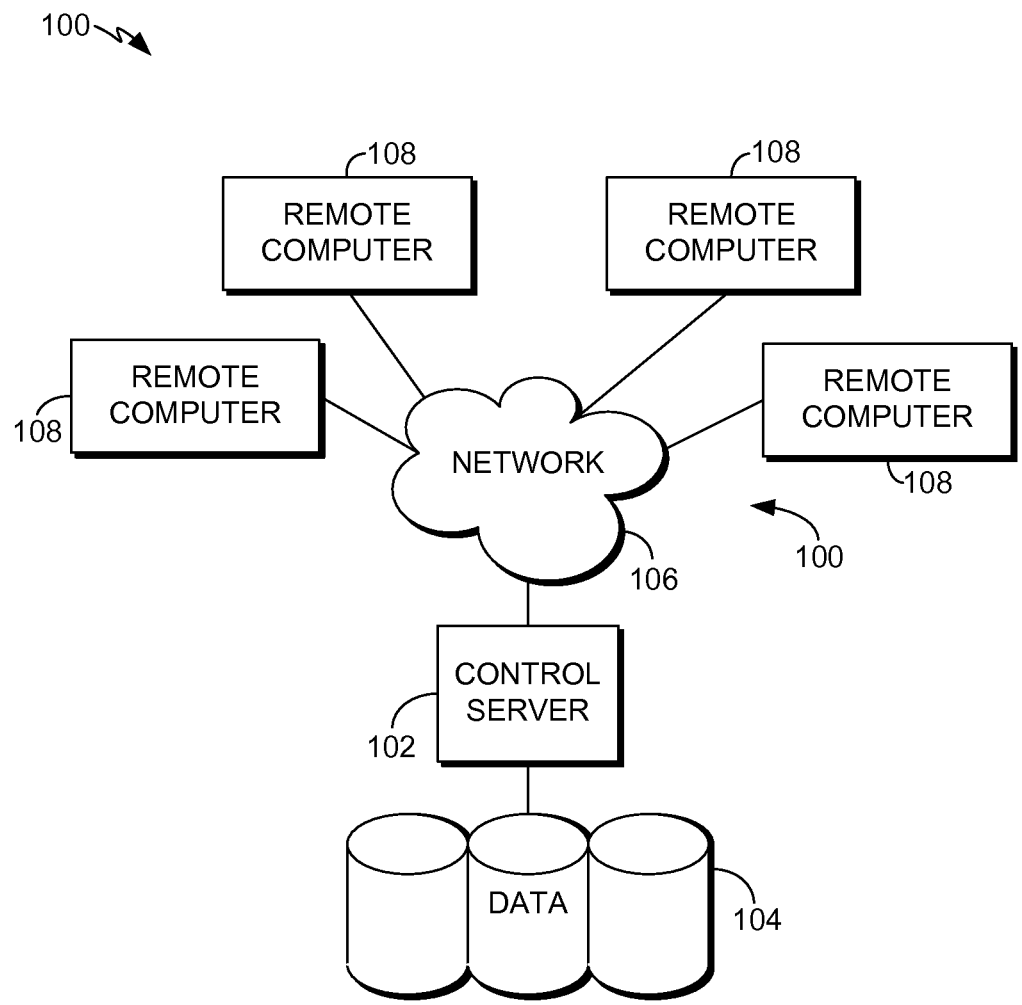
FIG. 1 is a block diagram of an exemplary computing environment suitable to implement embodiments of the present invention.

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies. Moreover, although the terms "step" and/or "block" might be used herein to connote different elements of methods employed, the terms should not be interpreted as implying any particular order among or between various steps herein disclosed unless and except when the order of individual steps is explicitly stated.

Embodiments of the present invention are directed to methods, computer systems, and computer storage media for managing fall risk for a patient in a clinical care room. Patients that have been classified as being a fall risk are automatically monitored through fall risk sensors located throughout the patient's clinical care room. The fall risk sensors include weight sensors and guard rail sensors associated with the patient's bed as well as location sensors that can determine the location and/or position of the patient within the clinical care room. Inputs from the fall risk sensors are utilized to determine if the patient is currently at risk for falling. If the patient is at risk for falling, alerts are initiated and settings in the clinical care room are modified to help decrease the patient's fall risk. For instance, an alert may be communicated to members of the patient's care team and a message may be presented on a display device in the patient's room informing the patient to stay in bed and that a caregiver will arrive shortly to assist the patient. These measures help to reduce the number of patient falls which, in turn, leads to improved patient safety and well-being.

Accordingly, one embodiment of the present invention is directed towards one or more computer-storage media having computer-executable instructions embodied thereon that, when executed by one or more computing devices, perform a method for managing fall risk for a patient in a clinical care room. The method comprises determining that the patient has previously been classified as a fall risk and automatically receiving one or more inputs from one or more fall risk sensors in the clinical care room. Based on the one or more inputs, it is determined that the patient is currently at risk for falling. One or more alerts are initiated and settings for components in the clinical care room are adjusted such that the patient's fall risk is decreased.

Another embodiment of the invention is directed towards one or more computer-storage media having computer-executable instructions embodied thereon that, when executed by one or more computing devices, perform a method for transitioning a clinical care room from a first scene to a second scene in order to facilitate management of a patient's fall risk. The method comprises presenting the first scene in the clinical care room having one or more zones, where the first scene is associated with a first group of setting for components within the one or more zones. It is determined that the patient has previously been classified as being at risk for falling. One or more inputs from fall risk sensors located in the clinical care room are automatically received, and it is determined, based on the inputs that the patient is currently at risk for falling. A second scene in the clinical care room is provided, where the second scene is associated with a second group of settings for the components within the one or more zones. The second group of settings is optimized to facilitate the management of the patient's fall risk.

Yet another embodiment of the invention is directed towards one or more computer-storage media having computer-executable instructions embodied thereon that, when executed by one or more computing devices, perform a method for managing fall risk for a patient in a clinical care room. The method comprises accessing the patient's electronic medical record and determining that the patient is classified as a fall risk. One or more inputs are received from fall risk sensors in the clinical care room. The fall risk sensors comprise one or more of a weight sensor, a rail sensor, or a location sensor. Based on the one or more inputs, it is determined that the patient is currently at risk for falling. Further, it is determined that a clinician is not in the clinical care room. Based on this information one or more actions are initiated; the actions comprise notifying one or more clinicians that the patient is currently at risk for falling, and communicating a message to the patient.

Having briefly described embodiments of the present invention, an exemplary operating environment suitable for use in implementing embodiments of the present invention is described below. FIG. 1 is an exemplary computing environment (e.g., medical-information computing-system environment) with which embodiments of the present invention may be implemented. The computing environment is illustrated and designated generally as reference numeral 100. Computing environment 100 is merely an example of one suitable computing environment and is not intended to suggest any limitation as to the scope of use or functionality of the invention. Neither should the computing environment 100 be interpreted as having any dependency or requirement relating to any single component or combination of components illustrated therein.

The present invention might be operational with numerous other purpose computing system environments or configurations. Examples of well-known computing systems, environments, and/or configurations that might be suitable for use with the present invention include personal computers, server computers, hand-held or laptop devices, multiprocessor systems, microprocessor-based systems, set top boxes, programmable consumer electronics, network PCs, minicomputers, mainframe computers, distributed computing environments that include any of the above-mentioned systems or devices, and the like.

The present invention might be described in the general context of computer-executable instructions, such as program modules, being executed by a computer. Exemplary program modules comprise routines, programs, objects, components, and data structures that perform particular tasks or implement particular abstract data types. The present invention might be practiced in distributed computing environments where tasks are performed by remote processing devices that are linked through a communications network. In a distributed computing environment, program modules might be located in association with local and/or remote computer storage media (e.g., memory storage devices).

With continued reference to FIG. 1, the computing environment 100 comprises a computing device in the form of a control server 102. Exemplary components of the control server 102 comprise a processing unit, internal system memory, and a suitable system bus for coupling various system components, including database cluster 104, with the control server 102. The system bus might be any of several types of bus structures, including a memory bus or memory controller, a peripheral bus, and a local bus, using any of a variety of bus architectures. Exemplary architectures comprise Industry Standard Architecture (ISA) bus, Micro Channel Architecture (MCA) bus, Enhanced ISA (EISA) bus, Video Electronic Standards Association (VESA) local bus, and Peripheral Component Interconnect (PCI) bus, also known as Mezzanine bus.

The control server 102 typically includes therein, or has access to, a variety of computer-readable media. Computer-readable media can be any available media that might be accessed by control server 102, and includes volatile and nonvolatile media, as well as, removable and nonremovable media. In this regard, computer-readable media might comprise RAM, ROM, EEPROM, flash memory or other memory technology, CD-ROM, digital versatile disks (DVDs) or other optical disk storage, magnetic cassettes, magnetic tape, magnetic disk storage, or other magnetic storage device, or any other medium which can be used to store the desired information and which may be accessed by the control server 102. The computer-readable media discussed provide storage of computer-readable instructions, data structures, program modules, and other data for the control server 102. Computer-readable media are non-transitory. Combinations of any of the above also may be included within the scope of computer-readable media.

The control server 102 might operate in a computer network 106 using logical connections to one or more remote computers 108. Remote computers 108 might be located at a variety of locations in a medical or research environment, including clinical laboratories (e.g., molecular diagnostic laboratories), hospitals and other inpatient settings, veterinary environments, ambulatory settings, medical billing and financial offices, hospital administration settings, home healthcare environments, and clinicians' offices. Clinicians may comprise a treating physician or physicians; specialists such as surgeons, radiologists, cardiologists, and oncologists; emergency medical technicians; physicians' assistants; nurse practitioners; nurses; nurses' aides; pharmacists; dieticians; microbiologists; laboratory experts; laboratory technologists; genetic counselors; researchers; veterinarians; students; and the like. The remote computers 108 might also be physically located in nontraditional medical care environments so that the entire healthcare community might be capable of integration on the network. The remote computers 108 might be personal computers, servers, routers, network PCs, peer devices, other common network nodes, or the like and might comprise some or all of the elements described above in relation to the control server 102. The peer devices can be personal digital assistants, smart phones, tablet PCs, personal computers, or other like devices.

Exemplary computer networks 106 comprise local area networks (LANs) and/or wide area networks (WANs). Such networking environments are commonplace in offices, enterprise-wide computer networks, intranets, and the Internet. When utilized in a WAN networking environment, the control server 102 might comprise a modem or other means for establishing communications over the WAN, such as the Internet. In a networking environment, program modules or portions thereof might be stored in association with the control server 102, the database cluster 104, or any of the remote computers 108. For example, various application programs may reside on the memory associated with any one or more of the remote computers 108. It will be appreciated by those of ordinary skill in the art that the network connections shown are exemplary and other means of establishing a communications link between the computers (e.g., control server 102 and remote computers 108) might be utilized.

In operation, an organization might enter commands and information into the control server 102 or convey the commands and information to the control server 102 via one or more of the remote computers 108 through input devices, such as a keyboard, a pointing device (commonly referred to as a mouse), a trackball, or a touch pad. Other input devices comprise microphones, satellite dishes, scanners, or the like. Commands and information might also be sent directly from a remote healthcare device to the control server 102. In addition to a monitor, the control server 102 and/or remote computers 108 might comprise other peripheral output devices, such as speakers and a printer.

Although many other internal components of the control server 102 and the remote computers 108 are not shown, such components and their interconnection are well known. Accordingly, additional details concerning the internal construction of the control server 102 and the remote computers 108 are not further disclosed herein.

Smart Clinical Care Room

Figure 2:
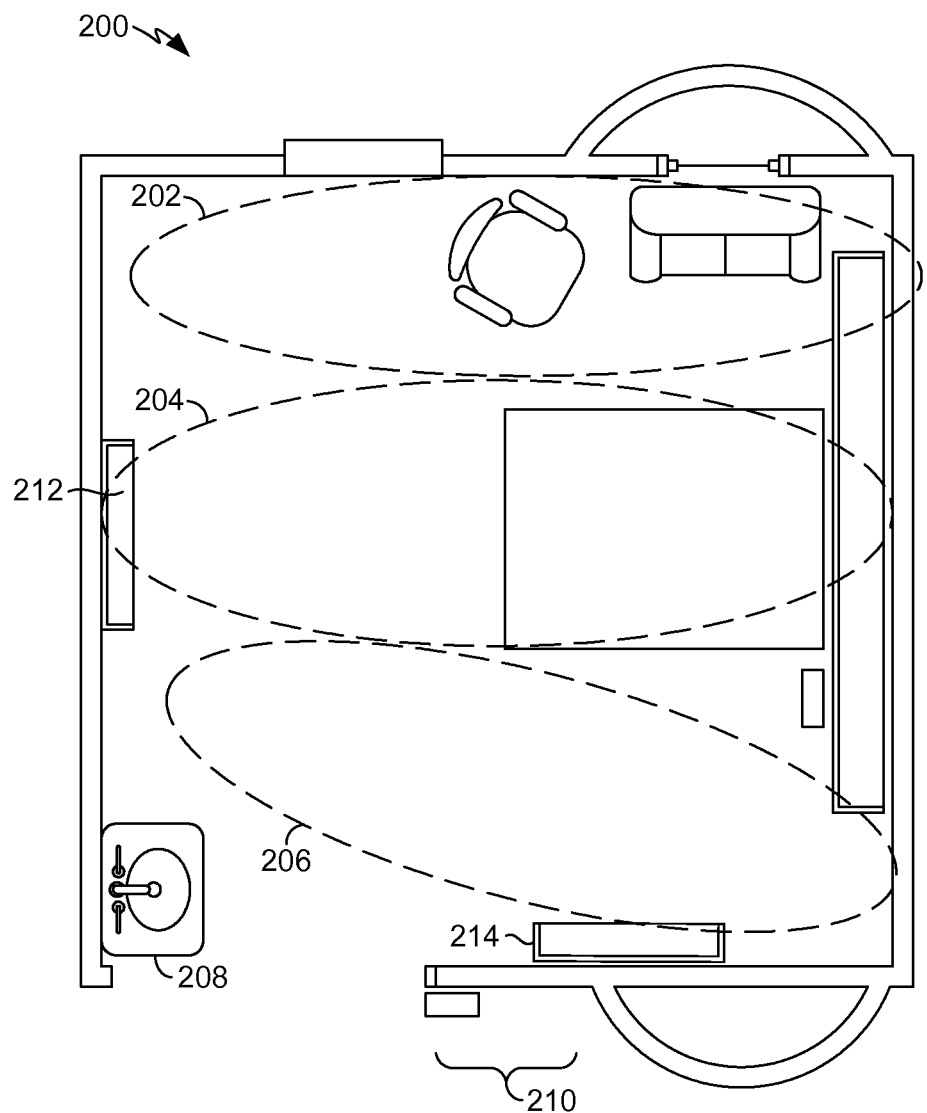
FIG. 2 depicts an exemplary layout of a smart clinical care room suitable to implement embodiments of the present invention.

Turning now to FIG. 2, an exemplary layout of a smart clinical care room 200 is depicted. FIG. 2 is merely one example of a suitable layout and is not intended to suggest any limitation as to the scope of use or functionality of the invention. In one aspect, smart clinical care room 200 is divided into three zones: a family/friend zone 202, a patient zone 204, and a clinician zone 206. The zones 202, 204, and 206 may be completely distinct from one another as shown in FIG. 2, or the zones 202, 204, and 206 may overlap. If two of the zones overlap, the area of overlap may be thought of as a conversion zone that combines features of both zones. As well, areas of overlap may support processes related to both zones depending on the individual situation.

Family/friend zone 202 is designed to be welcoming to the patient's family and/or friends and to help make them part of the patient's healthcare experience. As such, in one aspect, family/friend zone 202 is situated to be close to the patient yet out of a clinician's way. Comfortable furniture is provided that can easily be moved if more space in the room is needed. In one aspect, the furniture is designed to automatically fold up upon detection of a triggering event and upon determining that no one is sitting on the furniture. For example, upon detection of a code blue event, the furniture automatically folds up to create more room for clinicians. In yet another aspect, the family/friend zone 202 includes a television and a work area with phone and internet access (not shown) so family members can remain productive while still providing valuable support to the patient. Additionally, in still another aspect, the family/friend zone 202 includes a small suite adjacent to the smart clinical care room 200 with its own bed, shower, television, and work area (not shown). The family/friend zone 202 includes components that allow family members or friends to control their own television, lighting, and the like. Any and all such variations, and any combination thereof, are contemplated to be within the scope of embodiments of the present invention.

The patient zone 204 is generally located in the center of the smart clinical care room 200 between the family/friend zone 202 and the clinician zone 206. The patient zone 204 is where the care of a patient mainly takes place. The patient zone 204 includes certain components, including a bed, that allow the patient to manage aspects of the smart clinical care room 200. As well, certain components in the patient zone 204 assist the patient in becoming an active healthcare participant. These components are explained in greater depth below. The wall located at the head of the patient's bed is known as the head wall, while the wall at the foot of the patient's bed is known as the foot wall. In one aspect, a patient interactive station 212 (discussed in more detail later) is located on the foot wall within easy viewing distance of the patient.

Clinician zone 206 is designed to enhance a clinician's workflow as the clinician interacts with the patient and the patient's family and friends. It is generally positioned close to the entrance of the smart clinical care room 200. A sink for washing hands, and materials and equipment needed to care for the patient, are located within the clinician zone 206. The positioning of the sink and supplies reduces the number of areas the clinician contacts while in the room, which, in turn, reduces the spread of nosocomial infections. In addition, fatigue is reduced by decreasing the number of steps the clinician must travel within the smart clinical care room 200. In one aspect, a clinician-dashboard display device 214 (discussed in more detail later) is located on a wall in the clinician zone 206 within easy viewing distance of the clinician and the patient.

Although not all are depicted in FIG. 2, the smart clinical care room 200 may also include a number of other zones. By way of example, the smart clinical care room 200 may include a bathroom zone (not shown). With respect to the bathroom zone, a bathroom is located close to the patient's bed and has good lighting. As well, a clear path with railings is provided between the patient's bed and the bathroom. The bathroom may be equipped with sensors that can determine how long a patient has been in the bathroom and whether the patient has fallen while in the bathroom. Alerts may be automatically sent to a nurse if the patient has fallen or is in the bathroom for an inordinate amount of time.

The smart clinical care room 200 may also include a sanitizing zone 208 both outside the entrance to the smart clinical care room 200 (not shown) and within the smart clinical care room 200. The sanitizing zone 208 outside the entrance to the smart clinical care room 200 includes a hand-hygiene center that dispenses antiseptic hand rubs. The sanitizing zone 208 in the smart clinical care room 200 is located close to the entrance of the room within the clinician zone 206. This zone may include a sink with a timer so that clinicians, family members, and friends wash their hands for an appropriate length of time, an automatic dispenser of antiseptic handwash products, an automatic paper towel dispenser, a glove dispenser, a hands-free trash receptacle, and educational materials regarding the efficacy of handwashing in the prevention of disease. Antiseptic towelettes may be provided in the sanitizing zone 208 so that clinicians can wipe down equipment moveable from room to room such as, for example, stethoscopes. In addition, the sanitizing zone 208 in the smart clinical care room 200 may be equipped with sensors to detect the presence and identity of people at the sanitizing zone 208 and, in one aspect, to send alerts to the patient or clinician that proper handwashing has not taken place. In another aspect, upon detection of a presence at the sanitizing station, the water automatically turns on and the timer automatically starts. Any and all such variations, and any combination thereof, are contemplated to be within the scope of embodiments of the present invention.

The smart clinical care room 200 may also include a pre-room entrance zone 210, which contains the sanitizing zone 208 mentioned above along with room signage (discussed in more detail below) that delivers important information regarding the patient and/or the smart clinical care room 200.

A team zone and an operational zone may be located outside of the smart clinical care room 200. Although located outside the room, these zones have the ability to communicate and interact with the smart clinical care room 200. For example, an action taken in either the team zone or the operational zone may influence components present in the smart clinical care room 200. The team zone may be utilized in an intensive care environment where space is limited in the smart clinical care room 200. In this scenario, the team zone is located in front of a glass observation window. The zone is designed to allow multiple members of a clinical care team to congregate, view the patient through the glass observation window, view important information regarding the patient without disturbing the patient or the patient's family, and take actions that influence the components present in the smart clinical care room 200.

The operational zone is typically located at what is traditionally known as the nursing station. In one aspect, actions taken in the operational zone may influence components present in the smart clinical care room 200. The operational zone may include one or more display boards that display information not only about the patient and the smart clinical care room 200, but also about patients and components in other clinical care rooms, including smart clinical care rooms. The display boards may display information related solely to the patient in the smart clinical care room 200 upon detecting the presence of a clinician involved in the patient's care. Any and all such variations, and any combination thereof, are contemplated to be within the scope of embodiments of the present invention.

Figure 3:
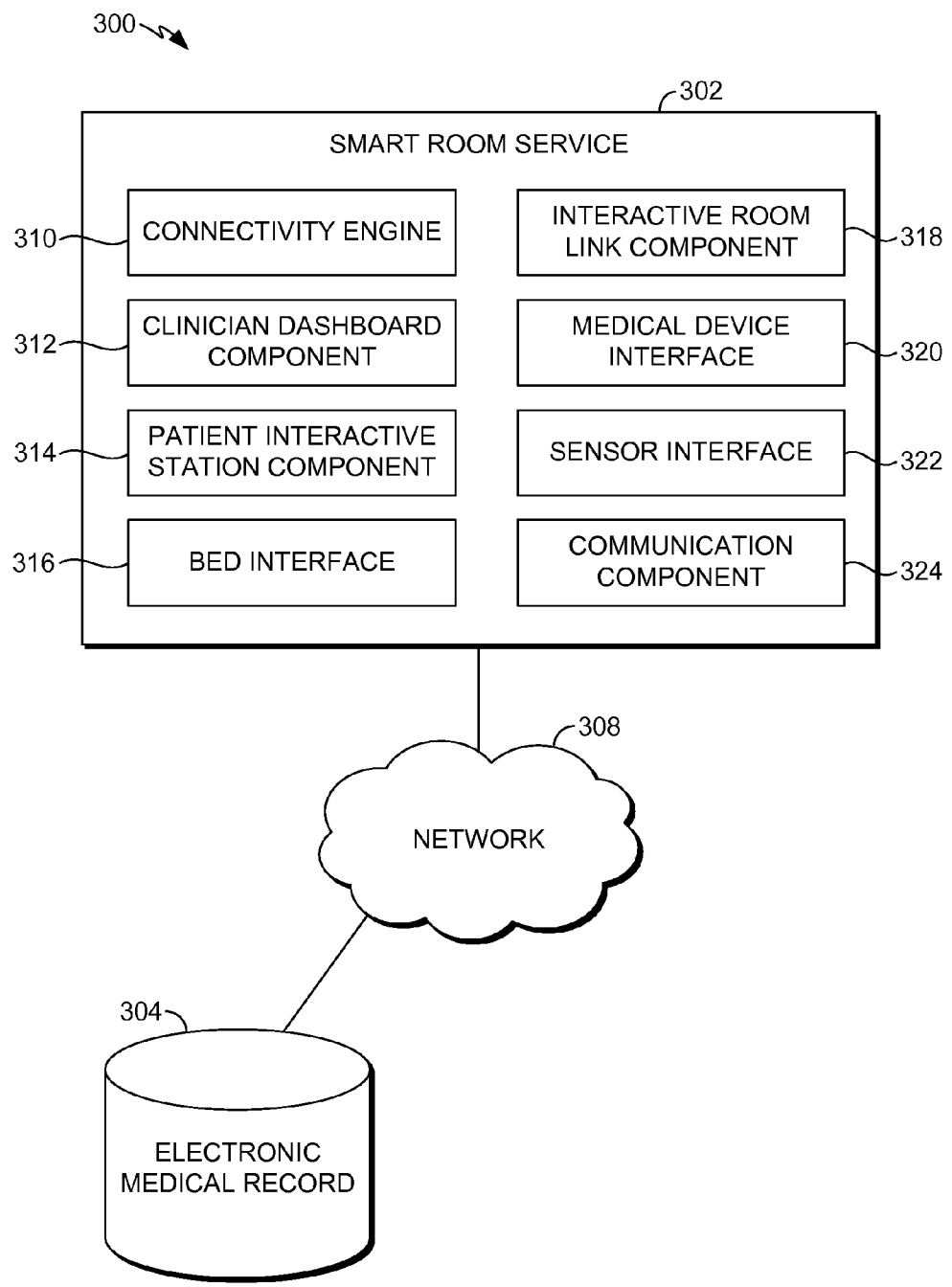
FIG. 3 is a block diagram of an exemplary computing system environment suitable for managing a smart clinical care room in accordance with an embodiment of the present invention.

Turning now to FIG. 3, a block diagram of an exemplary computing system environment 300 suitable for managing a smart clinical care room is depicted. It will be understood that the computing system environment 300 shown in FIG. 3 is merely an example of one suitable computing system environment for use with embodiments of the present invention. Neither should the computing system environment 300 be interpreted as having any dependency or requirement related to any single module/component or combination of modules/components illustrated therein. Further, many of the elements described herein are functional entities that may be implemented as discrete or distributed components or in conjunction with other components/modules, and in any suitable combination and location. Various functions described herein as being performed by one or more entities may be carried out by hardware, firmware, and/or software. For instance, various functions may be carried out by a processor executing instructions stored in memory.

The computing system environment 300 includes a smart room service 302, and an electronic medical record (EMR) 304 all in communication with one another via a network 308. The network 308 may include, without limitation, one or more local area networks (LANs) and/or wide area networks (WANs). Such networking environments are commonplace in offices, enterprise-wide computer networks, intranets and the Internet. Accordingly, the network 308 is not further described herein.

The EMR 304 comprises electronic clinical documents such as images, clinical notes, summaries, reports, analyses, or other types of electronic medical documentation relevant to a particular patient's condition and/or treatment. Electronic clinical documents contain various types of information relevant to the condition and/or treatment of a particular patient and can include information relating to, for example, patient identification information, images, physical examinations, vital signs, past medical histories, surgical histories, family histories, histories of present illnesses, current and past medications, allergies, symptoms, past orders, completed orders, pending orders, tasks, lab results, other test results, patient encounters and/or visits, immunizations, physician comments, nurse comments, other caretaker comments, and a host of other relevant clinical information.

The smart room service 302 shown in FIG. 3 integrates the components in the room with each other. The smart room service 302 may work with any type of computing device, such as, for example, control server 102 or remote computer 108, described with reference to FIG. 1.

The computing system environment 300 is merely exemplary. While the smart room service 302 is illustrated as a single unit, one skilled in the art will appreciate that the smart room service 302 is scalable. For example, the smart room service 302 may in actuality include a plurality of computing devices in communication with one another. The single unit depictions are meant for clarity, not to limit the scope of embodiments in any form.

As shown in FIG. 3, the smart room service 302 comprises a connectivity engine 310, a clinician dashboard component 312, a patient interactive station component 314, a bed interface 316, an interactive room link component 318, a medical device interface 320, a sensor interface 322, and a communication component 324. In some embodiments, one or more of the components and/or interfaces 310, 312, 314, 316, 318, 320, 322, and 324 may be implemented as stand-alone applications. In other embodiments, one or more of the components and/or interfaces 310, 312, 314, 316, 318, 320, 322, and 324 may be integrated directly into the operating system of a computing device such as the computing environment 100 of FIG. 1. In addition, one or more of the components and/or interfaces 310, 312, 314, 316, 318, 320, 322, and 324 may be integrated directly into the electronic medical record 304. The components and/or interfaces 310, 312, 314, 316, 318, 320, 322, and 324 illustrated in FIG. 3 are exemplary in nature and in number and should not be construed as limiting. Any number of components may be employed to achieve the desired functionality within the scope of embodiments hereof.

The connectivity engine 310 is connected to the components and/or interfaces 312, 314, 316, 318, 320, 322, and 324 either wirelessly or via a wired connection. The connectivity engine 310 interacts with multiple medical devices and their attendant workflows. In one aspect, the connectivity engine 310 is designed to have a touch screen and be interactive. The connectivity engine 310 displays, upon a prompt by a clinician, a list of medical devices that are available to connect with. The connectivity engine 310 also communicates with the medical device interface 320 to capture outputs from medical devices such as, for example, vital sign capture. The connectivity engine 310 also communicates with the medical device interface 320 to associate a medical device with a patient—a process that will be explained in greater detail below. The connectivity engine communicates captured data to the EMR 304.

In one embodiment of the invention, the connectivity engine 310 is able to connect to medical devices via the medical device interface 320 in the following categories: anesthesia, balloon pumps, beds, blood bank, chemistry, coagulation, communication, dialysis, fetal monitoring, hematology, imaging, laboratory automation, medication dispensing, microbiology, nurse call, ophthalmology, patient monitoring, point of care, pulse oximeters, respiratory, smart pumps, ultrasound, urinalysis, ventilators, and patient monitoring devices. This list is not meant to be exhaustive or limiting in any manner.

The connectivity engine 310 may be communicatively coupled to various medical devices through either are wired or wireless connection. In one embodiment, a computing device associated with the connectivity engine 310 is located near the medical devices. In one aspect, this location is on the headwall near the patient. In another aspect, the connectivity engine 310 is integrated into a patient's bed. In another embodiment, the connectivity engine 310 runs on a computing device (e.g., PDA, tablet PC) that is used to display data from the medical devices and/or other component/interfaces of smart room service 302.

The connectivity engine 310 also assists in detecting types of medical devices so that the appropriate driver may be loaded, which may be based on the make and model of the particular medical device. The medical device interface 320 or a component thereof communicates with the connectivity engine 310 to establish a connection to the medical device itself. In one embodiment, the connectivity engine 310 is physically present in a patient's room so that when a new medical device is brought into that room, it is connected to the connectivity engine 310 if needed. At that time, a connect event may occur, and, for example, the medical device interface 320 and/or the connectivity engine 310 broadcasts the connect event to other components who may need to know.

The clinician dashboard component 312 is a control panel that processes clinical information and drives relevant content to a clinician-dashboard display device. The clinician-dashboard display device, in turn, may comprise cathode ray tubes (CRT) systems, plasma screens, liquid crystal display (LCD) systems, rear projection systems, light emitting diode (LED) systems, organic light emitting diode (OLED) systems, and the like. Clinician dashboard component 312 processes and generates relevant content in the form of lab results, workflows, medications, orders, vital signs, allergies, notes, consult notes, patient information, a location of the patient if the patient is not currently in the room, and the like. In one aspect, the relevant content may be displayed on the clinician-dashboard display device in the form of a graphical user interface (GUI).

The clinician dashboard component 312, in one aspect, communicates with the sensor interface 322 to detect the presence and identity of a clinician in the room through the use of, for example, radio-frequency identification tags worn by the clinician. This ability to detect the presence and identity of a clinician can be leveraged to display clinical information that is particularly relevant to the identified clinician. By way of illustrative example, if the clinician is identified as a respiratory therapist, the clinician dashboard component 312 generates display information that is relevant to the respiratory therapist. In one aspect, the clinician dashboard component 312 generates a team view when multiple members of a clinical care team are present in the patient's room. The clinical information that is subsequently displayed on the clinician-dashboard display device is relevant to the clinical care team as a whole.

The clinician dashboard component 312 may be triggered to generate relevant information when a clinician pushes a button on an identification tag or interacts in some way with the clinician-dashboard display device. In one aspect of the invention, the clinician dashboard component 312 automatically generates relevant information when a clinician walks into the room by use of the sensor interface 322. In yet another aspect, the clinician dashboard component 312 is triggered to generate relevant clinical information by voice command or by the performance of a defined gesture. In addition, in one aspect, the clinician-dashboard display device automatically shuts down upon determining that the clinician is no longer in the room. Any and all such variations, and any combination thereof, are contemplated to be within the scope of embodiments of the present invention.

The clinician-dashboard display device may be a monitor(s) positioned strategically in a smart clinical care room, or it may be a handheld device (laptop, tablet PC, PDA, mobile device, etc.). In one aspect, at least one of the monitors is positioned in a clinician zone so that a clinician can view the patient and the monitor at the same time. The positioning of the clinician-dashboard display device in the clinician zone enables the patient to view the monitor along with the clinician. This helps to draw the patient into the healthcare process instead of just having the patient being a passive recipient of care.

In another aspect, the clinician-dashboard display device is located on a foot wall in a patient zone so that the patient can view the clinician-dashboard display device while in bed. The clinician dashboard component 312, in one aspect, presents a graphical user interface configured to receive patient questions regarding care when the clinician is not present in the hospital room. When the clinician is later present in the room, the clinician dashboard component 312 generates a display with the questions so that the patient and the clinician can go through the questions together—a process that also helps make the patient an active participant in the healthcare process.

The patient interactive station component 314 manages a set of modules and GUIs that are related to the modules and are displayed on a patient interactive station. The general purpose of the modules and the patient interactive station is to provide the patient and the patient's family with access to components to make the patient's stay at the hospital more enjoyable. The modules include an information module for providing the patient or the patient's family with information about the healthcare facility. For instance, the information module provides information such as a mission statement of the healthcare facility, a welcome video, or a list of amenities available to the patient. Information module also provides maps and other directional information to enable patients to find their way around the healthcare facility. Additionally, the information module may provide patients with information about the geographical area surrounding the healthcare facility, such as local events and venues for food and lodging.

A care team module provides the patient or the patient's family with information about the clinicians designated to care for the patient throughout the patient's stay at the healthcare facility. For example, the care team module provides information such as the name, position, picture and personal and professional biography of clinicians that interact with the patient during the hospital stay. The care team module is also associated with an indoor positioning system to track the physical locations of the clinicians. Additionally, the care team module in association with the indoor positioning system enables a patient to request biography information about a clinician based on the clinician's name or picture. This information, in turn, may be displayed when the clinician enters the patient's room.

An education module provides the patient with health education information. For instance, the education module enables the patient to retrieve electronic documents from, for example, EMR 304, related to the patient's illness or course of treatment. Alternatively, the education module provides interactive education tutorials for the patient. The education module, via the patient interactive station component 314, may also keep track of when a patient has completed a health education information learning activity such as retrieving an electronic document or completing an interactive tutorial. In one aspect, an alert is sent to the patient's nurse when the patient has completed a learning activity, and the nurse can complete needed follow-up with the patient to make sure the patient understands the educational materials.

A scheduling module provides the patient with a representation of specific events and/or a task list for the day. The events populated on the patient's schedule may include scheduled tests, standard food service times, chapel services, and hospital events. In addition to the scheduled events, the scheduling module provides the patient with a patient-specific task list. For example, the task list may include instructions for the patient related to treatment or education such as designated patient education tutorials and required or recommended exercises.

A health records module enables the patient to access information regarding personal care. For example, the health records module may enable the patient to access portions of the patient's personal health record and update pertinent information. The health records module, via the patient interactive station component 314, accesses the healthcare facility's records keeping system (i.e., the EMR 304) and determines via parameters set by a clinician, the portions of a patient's EMR 304 accessible by the patient. The health records module may also allow the patient to edit select portions of the EMR 304 associated with the patient. For example, the health records module may enable a patient to update information relating to allergies or update emergency contact information. Additionally, the health records module may allow the patient to communicate with the patient's physician or member of the clinical care team.

A treatment module provides real-time information from medical devices associated with the patient. For example, the treatment module retrieves the information from a bus, the medical device interface 320, the connectivity engine 310, or from data published from the medical device interface 320 to the EMR 304.

A feedback module allows patients to provide real-time opinion information regarding their stay at the healthcare facility. The feedback module solicits input from the patient via quality of care surveys. The feedback module may include instant feedback notices to allow clinicians and the healthcare facility to take immediate action regarding an issue and work to improve the overall patient experience. The notification component of the feedback module may include an escalation and relay measure, which alerts the clinicians when the results of a patient feedback survey fall below a satisfactory level. The feedback module allows the management of the healthcare facility to target specific areas for feedback regarding new protocols or processes. The feedback module eliminates the delays often associated with standard written survey results.

An environmental module allows the patient, a clinician, or the patient's family members and/or friends to control the environmental conditions of the patient's room. For instance, the environmental module enables the patient to adjust the lighting setting in the room. Alternately, the environmental module allows the patient to control the temperature of his or her room. In one aspect, the environmental module automatically adjusts the lighting settings and/or temperature settings in the room in response to a triggering event. For example, upon initiation of a code blue event, the lights may be brought to full illumination above the patient's bed.

The set of modules also includes a television module, a gaming module, a movie module, a music module, an aromatherapy module, a menu module, and a scene module. The television module provides television services to the patient and/or the patient's family and friends. For example, the television module facilitates the patient's ability to pause/rewind or record live television. Additionally, a clinician and/or a parent of the patient may control, via the television module, the times when television services are available to the patient and the type of programming accessible by the patient. Further, the television module facilitates the patient's and or clinician's ability to modulate the acoustic output from the television and/or turn the television on or off. In one aspect, the television module automatically adjusts the acoustic output and/or the power in response to a triggering event.

The gaming module provides an interactive gaming experience for the patient. For example, the gaming module facilitates gaming though externally connected gaming systems of built-in computer-based games. The movie module provides movies to the patient. The movie module may provide the movies upon demand. As with the television module, a clinician and/or a parent of the patient may control via the movie module the times when movies are available to the patient and the type of movie content accessible by the patient.

The music module provides music upon patient demand. The music module provides a music library that can be accessed via the patient interactive station component 314. Clinicians may control via the music module the times when the patient is allowed to access the music content. For instance, patients may be prohibited from accessing music content during scheduled quiet periods. Further, the music module may automatically adjust the acoustic output in response to a triggering event. The aromatherapy module provides patients with a variety of aromatherapy scents to enhance patient well-being. In turn, the menu module provides patients with access to the food service system of the healthcare facility as well as restaurants associated with the healthcare facility. The menu module may also provide access to gift shops associated with the healthcare facility.

The scene module provides the patient with the ability to initiate a variety of scenes in a smart clinical care room (i.e., the smart clinical care room 200 of FIG. 2). A scene is a combination of room settings that help to facilitate a real-world activity. By way of illustrative example, a patient may select a reading scene, a television watching scene, a relaxation scene, and the like. In one aspect, the scene module interacts with any of the other modules of patient interactive station component 314 (i.e., the television module, the environmental module, the gaming module, the aromatherapy module, etc.), any of the other components of the smart room service 302, and/or the EMR 304 to initiate the requested scene. In addition, in one aspect, the scene module controls a digital ceiling and/or a digital window located in the smart clinical care room so that the display from the digital window and/or ceiling corresponds to the requested scene. The concepts of scenes will be explored more fully below with respect to FIGS. 4A-4C and FIG. 5.

The patient interactive station is located where the patient can most easily interact with it (i.e., proximate to a patient in a patient zone of a room). For example, in one aspect, the patient interactive station is located on the foot wall; while in another aspect, it is located on a monitor beside the patient's bed or attached to the patient's bed. Interaction with the patient interactive station may be by touch. For example, the patient can touch the actual screen of the patient interactive station to make a selection. In another aspect, the patient is provided with a pillow speaker that allows interaction with the patient interactive station. In yet another aspect, the patient is provided with a small touch screen tablet to interact with the patient interactive station. Voice commands and pre-defined gesture recognition may also be used to interact with the patient interactive station. In one aspect, gesture recognition is used in conjunction with the education module. By way of illustrative example, a physical therapy order exists in the EMR 304 regarding the patient. The patient interactive station component 314 communicates with the EMR 304 and generates for display a set of physical therapy exercises. The exercises are displayed on the patient interactive station, and gesture recognition technology is utilized by the patient interactive station component 314 to document that the patient is performing the physical therapy movements correctly.

The bed interface 316 is configured to receive inputs and send out instructions to a patient bed located in a patient zone, and interface with the other components of the smart room service 302. In addition, the bed interface 316 may also interface with the EMR 304. By way of example, the bed interface 316 captures information generated by the bed related to vital sign monitoring, moisture detection, weight detection, and the like, and stores this information in the EMR 304. The bed interface 316 automatically and without human intervention adjusts the bed to any number of positions in response to certain inputs to facilitate caring for the patient. For example, the head of the bed is adjusted to a certain angle upon receiving an indication that the patient is at risk for hospital-acquired pneumonia or ventilator-acquired pneumonia. In addition, the bed interface 316 may generate alerts to the clinical care staff if, for example, the head of the bed falls below a certain angle and the patient is at risk for pneumonia or has a diagnosis of pneumonia. The bed interface 316 may also automatically adjust the bed in response to certain triggering events which will be discussed in greater depth below.

The interactive room link component 318 receives inputs and communicates with room signage located outside the entrance to a smart clinical care room (i.e., in the pre-room entrance zone 210 of FIG. 2). In one aspect, inputs are received by the interactive room link component 318 via a touch screen on the room signage, a mobile application, verbal or gesture interaction with the room signage, or by some other attribute present in the smart clinical care room such as, for example, the patient interactive station. The interactive room link component 318 may generate for display by the room signage pertinent updates as clinician orders are received. By way of illustrative example, if an order is written restricting access to food in preparation for surgery, the room signage displays a message indicating that the patient is not allowed to have any food. This effectively notifies clinical care team members, hospital staff, as well as family and friends of the patient that the patient is not allowed to have food.

In another aspect, the patient or the patient's family can push messages out to the room signage via the interactive room link component 318. For example, the patient generates a message using, for example, the patient interactive station. This message is communicated to the interactive room link component 318 and subsequently displayed on the room signage. For example, the patient posts a message that the patient is visiting the gift shop and will be back shortly.

In another aspect of the invention, the interactive room link component 318 receives inputs indicating that the healthcare facility's transport service is transporting the patient. For example, the transport service indicates start and stop times of the transporting process by interacting with the room signage or by inputting the start and stop times on a mobile application. As well, housecleaning services also indicate start and stop times of the cleaning process by interacting with the room signage, or via a mobile application. Although not detailed here, many examples exist where the interactive room link component 318 receives inputs or generates outputs related to a clinician, patient, or hospital staff.

With respect to the medical device interface 320, a clinician may wish to associate a patient and at least one medical device via the medical device interface 320. In other words, the medical device interface 320 provides the needed link between a clinician, a medical device, and a patient. This association between the medical device and the patient allows the clinician to continually receive data from the associated medical device for as long as it is associated with the patient. This continuous feed of data may be fed from the medical device to the medical device interface 320 and on to other components/interfaces of the smart room service 302. The data is then sorted, and routed to the appropriate services and applications, such as a patient-to-device association application. Medical devices include any devices or mechanisms that may be used by a patient during a hospital stay. These medical devices may include a patient bed, monitors (e.g., fetal monitors), pumps (e.g., infusion pump), cardiac ventilators, sequential compression devices, electronic security devices, pharmacy dispensing stations, and the like. Further, the association of a patient to a medical device may continue until the occurrence of a disassociation event, which will be described below. The association continues not only when the medical device is in a smart clinical care room, but may continue for an extended period of time until a disassociation event occurs.

The medical device may be associated with the patient via the medical device interface 320 using patient identification information including, but not limited to, the patient's name, gender, date of birth, identification number, and the like. There are many ways to identify a patient. For instance, a patient may be identified by scanning a barcode that is located on or near the patient. When a patient is admitted to a hospital the patient may wear a wristband that has a barcode such that the patient may be easily identified. Alternatively, a patient's bed may have the patient's identification located somewhere on it for quick access. Another form of identification may be used instead of a barcode, such as a patient identification number or other identification form that may be entered into a mobile computing device (e.g., PDA or mobile PC) to identify the patient.

Another option for identifying a patient may include searching a database for a specific patient. The database may include each patient who is currently admitted to the hospital and thus any patient who is admitted to the hospital may easily be found in the database.

As mentioned above, the connectivity engine 310 displays any medical devices that have been identified and/or associated to the patient. Medical devices are identified in many of the same ways that patients are identified. For example, a barcode located on or near a medical device may be scanned, and information corresponding to that medical device may be uploaded to a mobile or portable computing device for display. Or, an identification number or other identifier corresponding to the medical device may be entered, either manually or electronically, to a portable computing device, for example. Alternatively, a search function may allow a clinician to search for a specific medical device that is located in a database even if that medical device is not associated with the identified patient. RFID tags may be associated with devices or patients.

Embodiments of the present invention allow a clinician to disassociate medical devices that are currently associated to a patient. In one aspect, a clinician may select specific medical devices, and select a disassociate button, and the selected medical devices will be disassociated from the patient. For example, upon a patient checking out of a hospital to return home, the medical devices that had been used to treat the patient, and, thus, had been associated to the patient, may be disassociated by the method described above. There are other ways that medical devices may be disassociated from a patient. For instance, the medical device may become disassociated by a patient when another patient becomes associated with that same medical device. This override may take place when a clinician is presented with a dialog box that indicates to the clinician that another patient is associated with that medical device. The clinician may have the option, in some embodiments, to override the existing association.

Sensor interface 322 communicates with sensors and/or identifiers located not only in a smart clinical care room, but throughout the healthcare facility in which the patient is located. The sensor interface 322 tracks the location of identifiers in the healthcare facility and receives information and inputs emitted from the sensors. The sensors and/or identifiers may utilize ultrasound technology, infrared technology, radio-frequency identification (RFID) technology, or the like. Identifiers are worn by clinicians, patients, and/or family members and may take the form of a security badge, an item attached to a security badge, or the like. Sensors are located at fixed intervals in the healthcare facility including the patient room.

Signals are transmitted by the sensors and are received by the identifiers. The identifiers respond to the signals. A response from an identifier is received by the sensors and communicated to the sensor interface 322. The sensor interface 322 recognizes and determines the location and identity of the responding identifier. For example, when a clinician identifier is identified by the sensor interface 322, the location for the clinician associated with the clinician identifier is updated. The information concerning the location of the clinician may be shared with the patient and/or the patient's family. In one aspect, the sensor interface 322 communicates the information to the interactive room link component 318, and the location information is displayed on the room signage. In another aspect, the location information is displayed on a patient interactive station associated with the patient interactive station component 314.

The sensor interface 322 may also be utilized to optimize a clinical experience for a patient or an individual associated with the patient, such as a family member. The clinical experience is often overlooked for the individuals associated with the patient. Many times, family members sit with a patient for endless hours to avoid leaving the patient's side and missing an important clinical event without ever being notified of an opportunity to be included in the clinical event. Embodiments of the present invention seek to alleviate the stress on the patient and the patient's family.

Privacy regulations provide that patient information may not be shared with unauthorized individuals. Thus, embodiments of the present invention are applicable to one or more individuals that are approved by the patient to receive notifications of clinical information. The individual receiving the clinical information must also enable a computing device to receive the clinical information. Any web-enabled computing device may receive clinical information. The clinical information may be received in the form of a notification and/or message.

By way of example only, assume that a non-present party (e.g., a family member) has left the patient's room to go to a vending machine. The non-present party would like to be notified if the patient's clinician is near the patient. A mobile computing device may receive such a notification, and the non-present party can return to the room to speak with the clinician.

The non-present party may be tracked via an identifier in the same way as patients and clinicians are tracked. The present invention may also include predefined location stations to aid navigation such that it is not necessary that a non-present party be tracked. The non-present party may simply identify their location at the location station and utilize the present invention in the same way as if they were being tracked. If the non-present party is presented with turn-by-turn directions, then the steps will update upon receiving an indication from the user to present the next step. Alternatively, the non-present party could be tracked via a plurality of sensors and the directions may automatically update as the non-present party's location is updated from passing a sensor.

The communication component 324 is configured to communicate with communication devices used within a healthcare facility to receive and send information. The communication component 324 is also configured to receive requests for additional information and to communicate with other components and/or interfaces of the smart room service 302. Additionally, the communication component 324 is configured to communicate alerts and or notifications. Exemplary communication devices include personal communication devices, a workstation, a nursing station, a nurse call system, an intercom system, and an email system.

Personal communication devices include devices that are used by an individual to receive and send information, such as an in-house phone, a pager, and a mobile device. A workstation includes a remote computer terminal that is used to present information to clinicians and receive inputs from clinicians. A workstation might be set up at a nurse's station to or at a patient's bedside. A nurse call system includes communication devices that present information to and receive information from a nurse (or other healthcare professional). An intercom system includes communication devices that receive and announce information by utilizing, for example, speakers. An email system might be implemented using one or more of the other communication devices (for example, a personal communication device, or a workstation) to send and receive messages (e.g., email messages, SMS messages, etc.) to various users.

Accordingly, in an embodiment of the present invention, the communication component 324 presents information to clinicians using one or more of the communication devices outlined above. The information may be received by the communication component 324 from other components and/or interfaces of the smart room service 302. For example, the communication component 324 may receive information concerning a medical device via the medical device interface 320 or the connectivity engine 310 and communicate this information to a nurse call system, or a personal communication device. Moreover, the communication component 324 might also generate information (e.g., code-blue alert) that is communicated to other components of the smart room service 302. As well, the communication component 324 is configured to communicate to other components of the smart room service 302 requests to receive additional information. For example, a personal communication device might communicate a request of a physician to receive information from the EMR 304.

The zones and components discussed above with respect to FIGS. 2 and 3 are used to transition a smart clinical care room (i.e., the smart clinical care room 200 of FIG. 2) from a first scene to a second scene. The transition from a first scene to a second scene can be in response to some triggering event. The triggering event may be a manual trigger by a clinician, a patient, or a family member or friend of the patient. In another aspect, the triggering event is an automatic trigger upon detection of certain information. In one aspect of the invention, the second scene facilitates completion of the real-world activity. A real-world activity comprises physical involvement with one or more people to realize a tangible goal. A person may use a computing device or machine to complete the real-world activity, but the real-world activity is not solely performed by a computing device. The transition to a scene that facilitates completion of the real-world activity can be accomplished by a computing-device alone, without human interaction. One or more of the zones discussed above, along with a smart room service (i.e., the smart room service 302 of FIG. 3), are utilized to transition from a first scene to a second scene. FIGS. 4A-4C and FIG. 5 provide some illustrative examples of types of scenes contemplated to be within the scope of the invention. The arrangements shown in FIGS. 4A-4C and FIG. 5 are merely exemplary and are not meant to be limiting in any way.

Figure 4A:
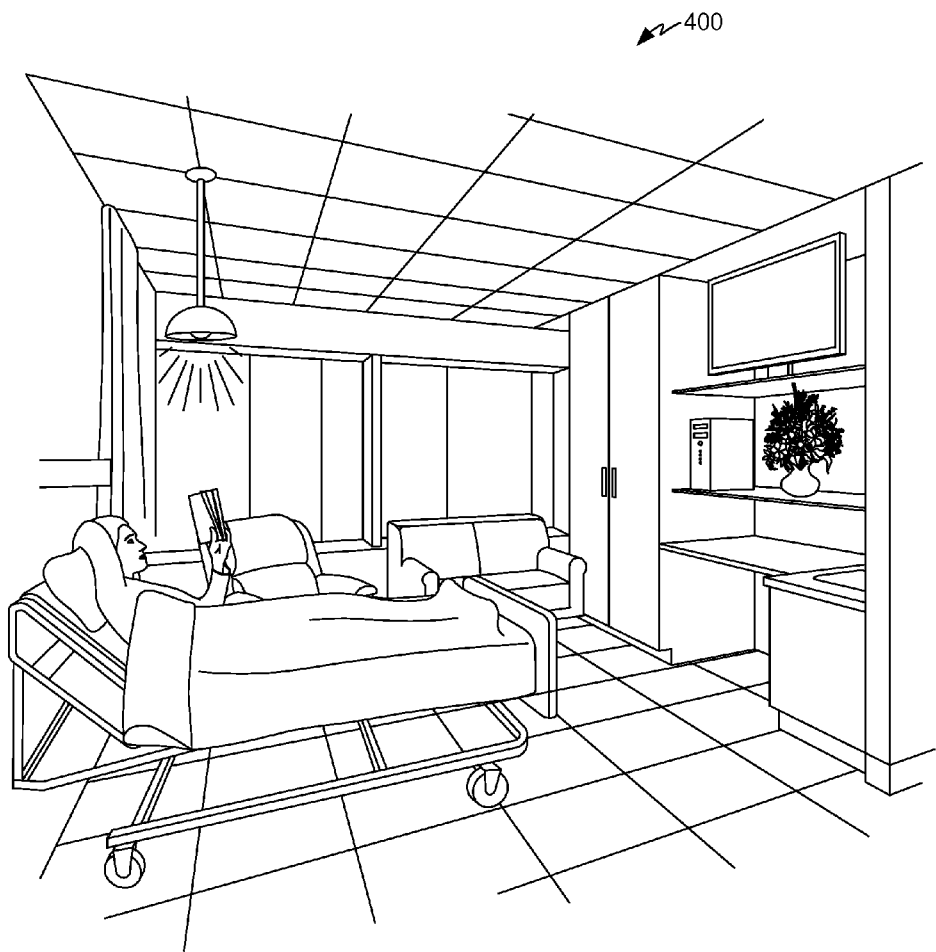
FIGS. 4A-4C depict exemplary scenes associated with a smart clinical care room suitable to implement embodiments of the present invention.

FIG. 4A depicts a reading scene and is referenced generally by the numeral 400. In one aspect, a patient, or a visitor of the patient, in a smart clinical care room interacts with, for example, a patient interactive station to request a reading scene. In another aspect, the patient interacts with some other component of a smart room service (i.e., the smart room service 302 referenced in FIG. 3) to request a reading scene. Upon receiving the request for the reading scene, the smart clinical care room is automatically and appropriately illuminated, acoustic outputs are automatically minimized, and the patient bed is automatically adjusted to a position that facilitates reading. For example, the head of the bed is adjusted to elevate the upper half of the patient's body. In another aspect of the invention, a friend or family member of the patient interacts with the patient interactive station to request a reading scene for the friend or family member. In this instance, the family zone of the smart clinical care room is illuminated and acoustic outputs minimized. Any and all such variations, and any combination thereof, are contemplated to be within the scope of embodiments of the present invention.

Figure 4B:
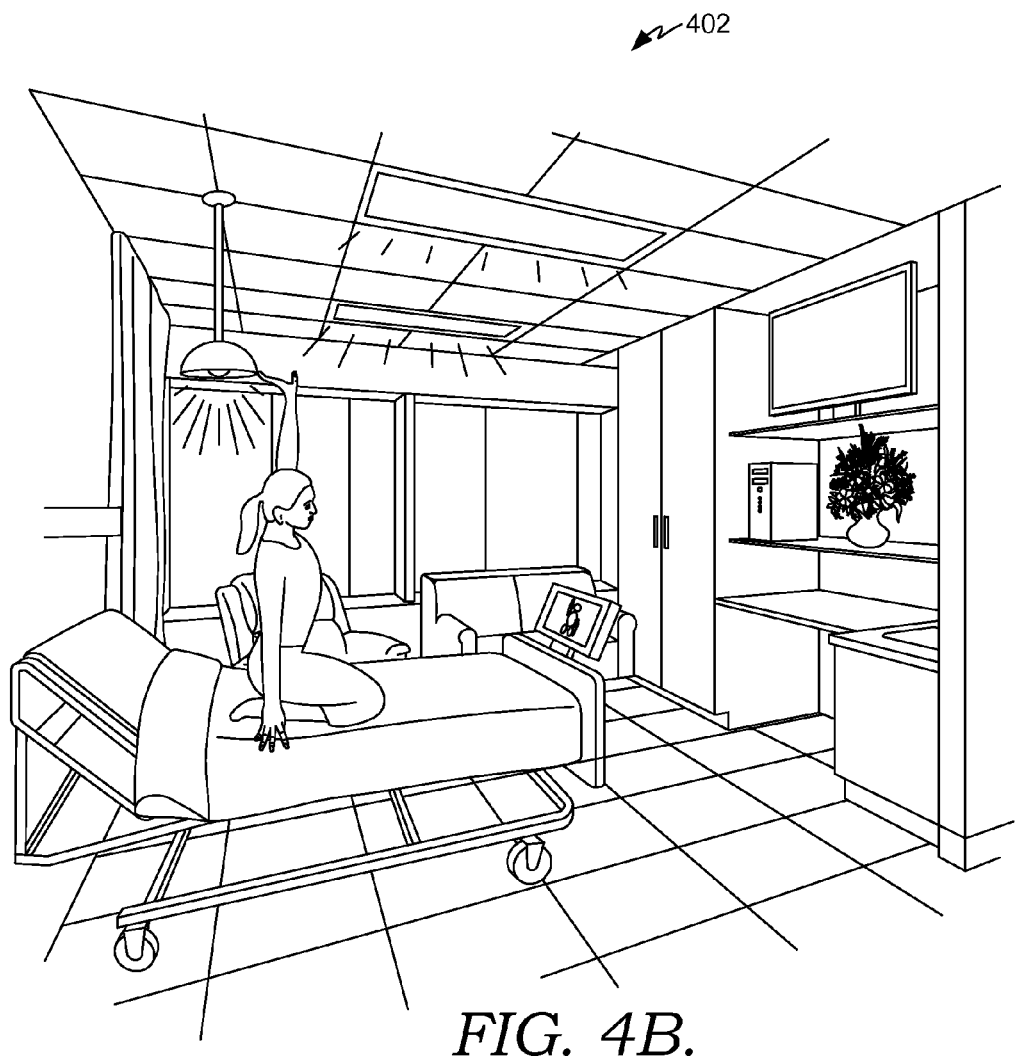

FIG. 4B depicts a physical therapy scene and is referenced generally by the numeral 402. A smart room service may receive an indication that communicates the patient is ready to begin a physical therapy session. Such an indication could be received from a clinician or from the patient. By way of illustrative example, the patient interacts with a patient interactive station, or the clinician interacts with a clinician-dashboard display device. In another aspect, the smart room service accesses the physical therapy order through an electronic medical record (i.e., the EMR 304 of FIG. 3). Incident to receiving this indication, the room is illuminated in order to facilitate the physical therapy session, acoustic outputs are adjusted so that there is minimal sound in the room, and the bed is adjusted to facilitate the patient's physical therapy, the type of adjustment is dependent upon what type of physical therapy movements are prescribed. In addition, a physical therapy module is displayed on a monitor positioned so that the patient can both view the monitor and perform the physical therapy movements. In one aspect of the invention, gesture recognition technology is utilized to ensure the patient is performing the physical therapy movements correctly. If, for example, it is detected that a movement is not being performed correctly, the physical therapy module initiates a training module to help the patient learn the correct movement. Any and all such variations, and any combination thereof, are contemplated to be within the scope of embodiments of the present invention.

Figure 4C:
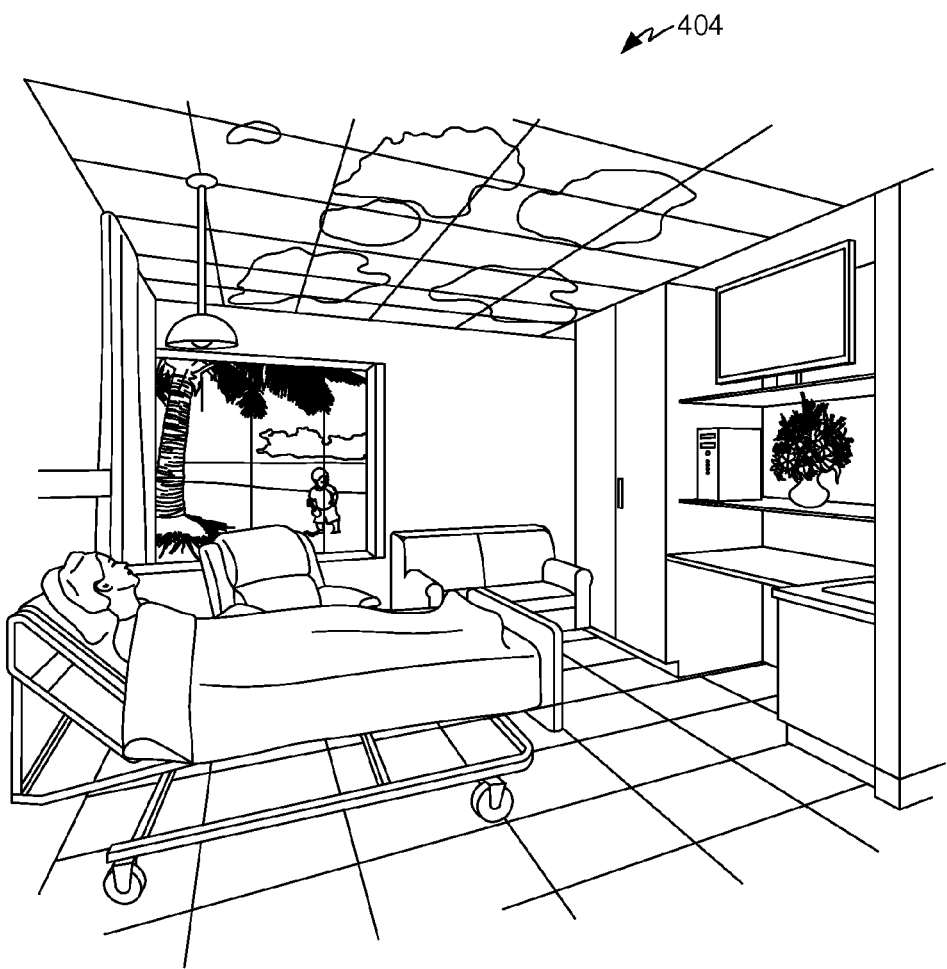

FIG. 4C depicts a relaxation scene and is referenced generally by the numeral 404. An indication is received by, for instance, a smart room service (i.e., the smart room service 302 referenced in FIG. 3) that a relaxation scene is desired. For example, the indication is received from a clinician, the patient, or a member of the patient's family and occurs through interaction with, e.g., a patient interactive station or a clinician-dashboard display device. Upon receiving the indication, a digital ceiling and/or window in a patient room is set to scenery that evokes a relaxed state of mind, illumination in the room is dimmed, soothing music is played, aromatherapy initiated, and a patient bed in the room is set to a position that facilitates relaxation. For example, the head of the bed may be adjusted so that the patient's upper body is slightly elevated. Any and all such variations, and any combination thereof, are contemplated to be within the scope of embodiments of the present invention.

Figure 5:
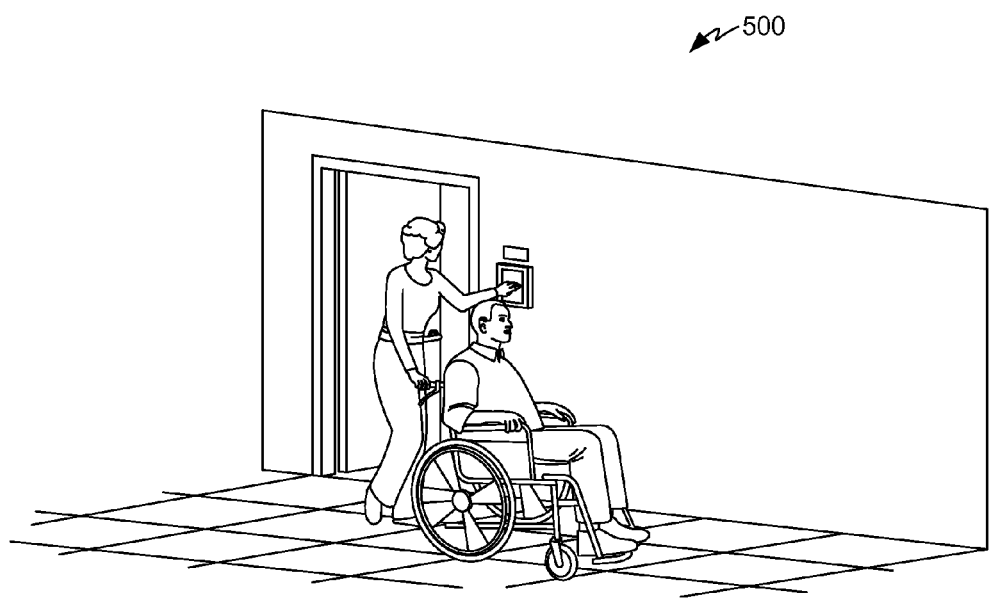
FIG. 5 depicts an exemplary scene associated with a smart clinical care room suitable to implement embodiments of the present invention.

FIG. 5 depicts a transport scene and is referenced generally by the numeral 500. The transport scene may be triggered, for example, upon a smart room service (i.e., the smart room service 302 of FIG. 3) receiving an indication from a clinician that the patient needs to be transported to a specified location in the healthcare facility. For example, an order is entered, stored in an electronic medical record (i.e., EMR 304 of FIG. 3), and communicated to the smart room service. In one aspect of the invention, a transporter receives an indication (for example, by receiving a notification via the communication component 324 of FIG. 3 on a mobile device) that a patient in a smart clinical care room needs to be transported. After assisting the patient into a wheelchair, the transporter interacts with, for example, the room signage upon leaving the room with the patient. Incident to this interaction, lights and televisions in the room are turned off, an indication that the patient is being transported is displayed on the room signage, and clinicians and family members are notified that the patient is in transport and is not present in the room. Upon returning to the smart clinical care room with the patient, the transporter again interacts with the room signage to indicate that the patient has returned to the room. Incident to this interaction, the room lights and television are adjusted to pre-transport levels, the room signage displays a message indicating the patient is in the room, and clinicians and family members are notified (via, for example, the communication component 324 of FIG. 3) that the patient is back in the room. FIGS. 4A-4C and FIG. 5 are representative examples of the many scenes that may be initiated in the smart clinical care room 200.

Figure 6:
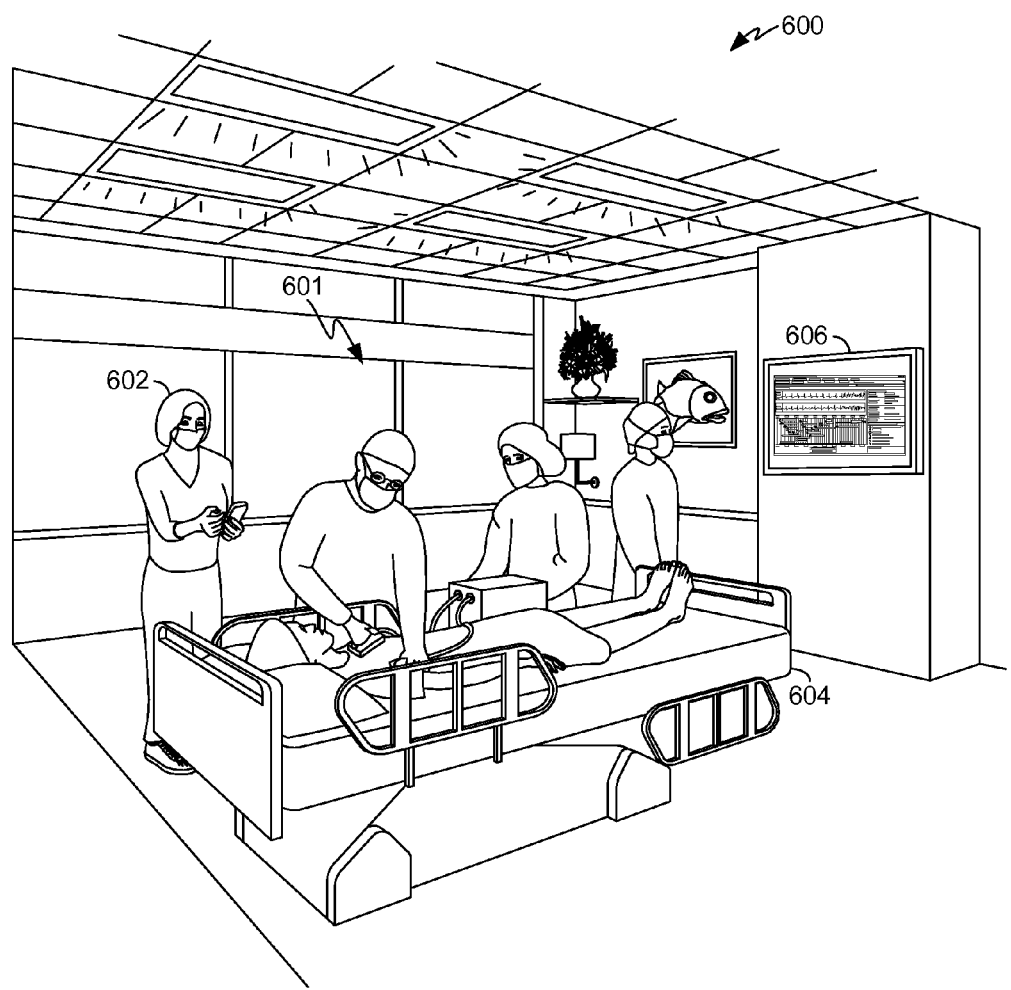
FIG. 6 depicts an exemplary code blue scene associated with a smart clinical care room suitable to implement embodiments of the present invention.

One scene that is of critical importance in a healthcare setting is a code blue scene. This scene is depicted in FIG. 6 (referenced generally by the numeral 600) and will be explained in greater depth below. The term code blue as used in this application refers to a patient experiencing cardiopulmonary arrest. The successful management of a code blue event requires quick detection of the code blue event, rapid response times by a code blue team, knowledge of code blue protocols, coordination of the code blue team, and accurate documentation of clinical events that occur during the code blue event. The smart clinical care room is designed to meet these needs through the use of the zones and the components present in the room.

In one aspect of the invention, a code blue alert is activated via voice, touch or gesture and recognized by, for example, a clinician dashboard display device or a patient interactive station. In another aspect, a code blue alert is automatically activated upon detection of a triggering event by a patient monitoring device such as, for example, a cardiac arrhythmia, asystole, pulmonary arrest, and the like. In one aspect, upon activation of the code blue alert, a clinician responsible for the patient is notified; the clinician would check the patient and initiate a full code blue alert if the code blue event is verified. In another aspect of the invention, a code blue team (referenced by the numeral 601 in FIG. 6) is automatically notified when the code blue alert is activated. The team 601 may be notified, for example, by a notification sent to one or more mobile devices associated with the code blue team 601. The notification includes information about the patient such as, for example, name and location in the healthcare facility.

Upon triggering of the code blue event, a dome light outside the room entrance is illuminated and the room signage displays a message indicating a code blue occurrence. Both of these measures allow the code blue team members 601 to quickly identify the room in which the code blue event is occurring which decreases response times. Acoustic outputs are minimized in the room by, for example, powering off any televisions that are on, and turning off any music that is playing. Referring to FIG. 6, the room is brought to full illumination. Furniture in the family zone may automatically fold up to help clear space for the code blue team members 601 upon determining that no one is sitting on the furniture. In essence, the smart clinical care room is effectively converted to one large clinician zone. A patient bed 604 in FIG. 6 is automatically positioned to a code blue position upon determining that the patient is securely on the bed. For example, a bed interface (i.e., the bed interface 316 of FIG. 3) determines that the patient's weight is substantially below a recently documented weight for the patient. Such determination prevents the bed from being automatically adjusted to a code blue position. In addition, a crash cart may be associated with the patient.

In one aspect of the invention, a clinician dashboard component (i.e., the clinician dashboard component 312 of FIG. 3) generates for display by a clinician-dashboard display device a code blue team view 606 where the team view can be seen by all members of the code blue team 601. The code blue team view 606 can be in the form of a GUI. The code view team view 606 displays clinical event information in near real-time. The clinical event information is automatically captured, or manually inputted. By way of illustrative example, the clinician dashboard component captures information from any of the components present in the smart clinical care room. As well, the clinician dashboard component captures information that is being manually documented by a member of the code blue team 601 that is in charge of documentation, hereinafter known as the documenter. The documenter is indicated by the numeral 602 in FIG. 6.

Figure 8:
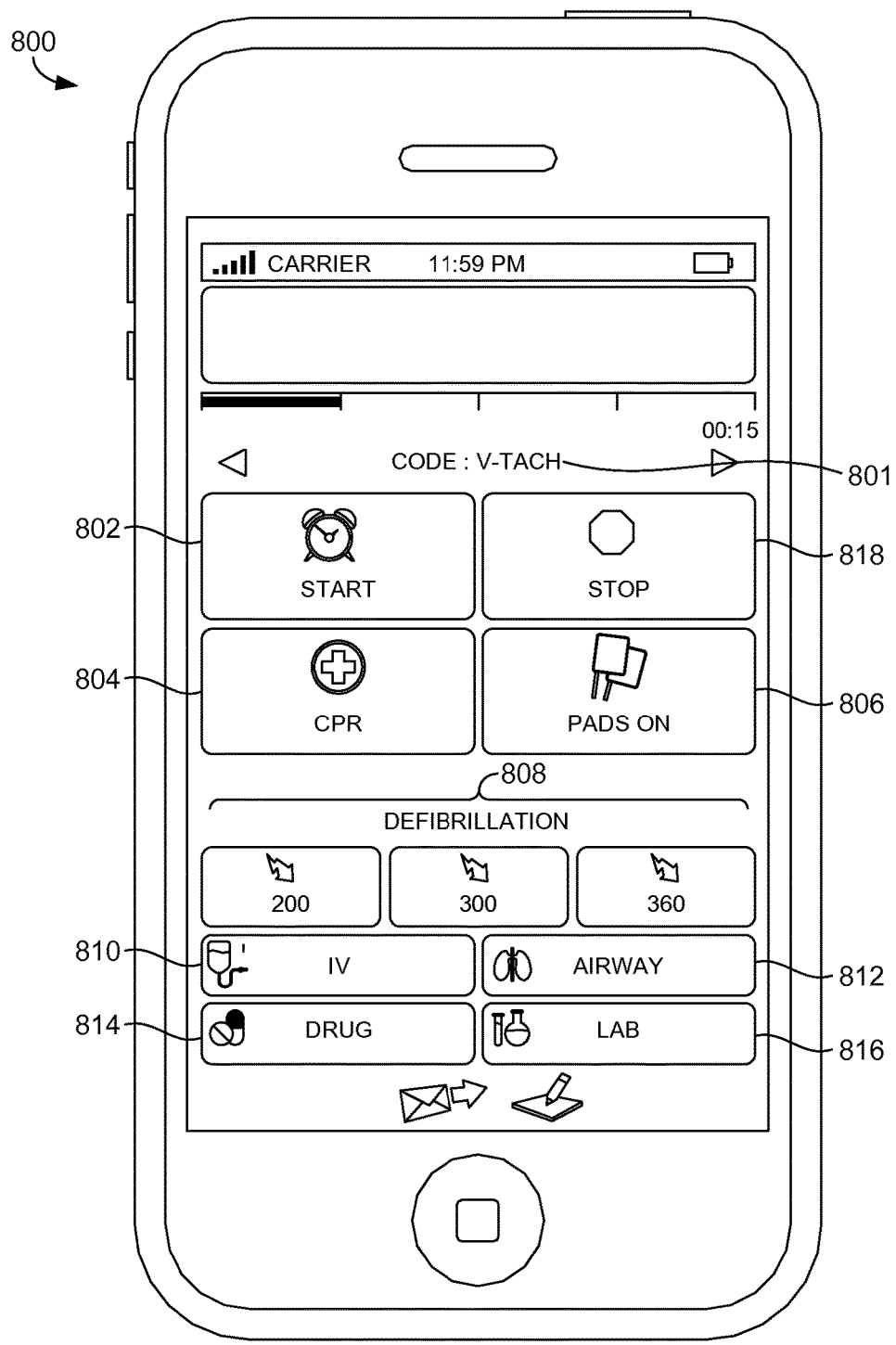
FIG. 8 depicts an exemplary graphical user interface of a device associated with a code blue event suitable to implement embodiments of the present invention.

FIG. 8 depicts an input device that is used by the documenter 602, referenced generally by the numeral 800, to record clinical event information during the code blue event. In one aspect, the information is inputted via an application on a mobile device. With respect to FIG. 8, the documenter 602 may input a medical condition 801 that initiated the code blue event, such as, for example, ventricular tachycardia (V-Tach). A time 802 the code blue response begins is documented as well as a time 804 that cardio-pulmonary-resuscitation (CPR) begins. If the patient requires defibrillation, a time 806 at which the defibrillator pads are placed on the patient is noted, along with times and energy amounts 808 of shocks delivered to the patient. The documenter 602 is able to document any intravenous fluids 810 the patient may be receiving, the necessity or type of airway 812 that may be established for the patient, drugs 814 administered to the patient, and labs and lab results 816 drawn on the patient. In addition, the documenter 602 can also input a stop time 818 for when the code blue response is terminated.

As mentioned, the clinician dashboard component captures the information inputted by the documenter 602 along with clinical event information captured by other components in the smart clinical care room. For example, the clinician dashboard component captures identities of code blue team members 601 along with a time that the code blue team members 601 arrive in the room through communication with, for example, a sensor interface (i.e., the sensor interface 322 of FIG. 3). The use of sensors in the smart clinical care room enables monitoring of the movement of code blue team members 601 and equipment throughout the room. The use of sensors also allows a position in the room to be determined for each member of the code blue team 601. This may be important at a later point in time when quality measures are reviewed with respect to the code blue response.

The code blue team view 606 generated by the clinician dashboard component dynamically changes depending on the type of clinical event information received by the smart room service. Thus, code blue protocols can be dynamically updated depending on the results of, for example, labs drawn, medications delivered to the patient, shock treatments administered to the patient, and the like.

Figure 7A:
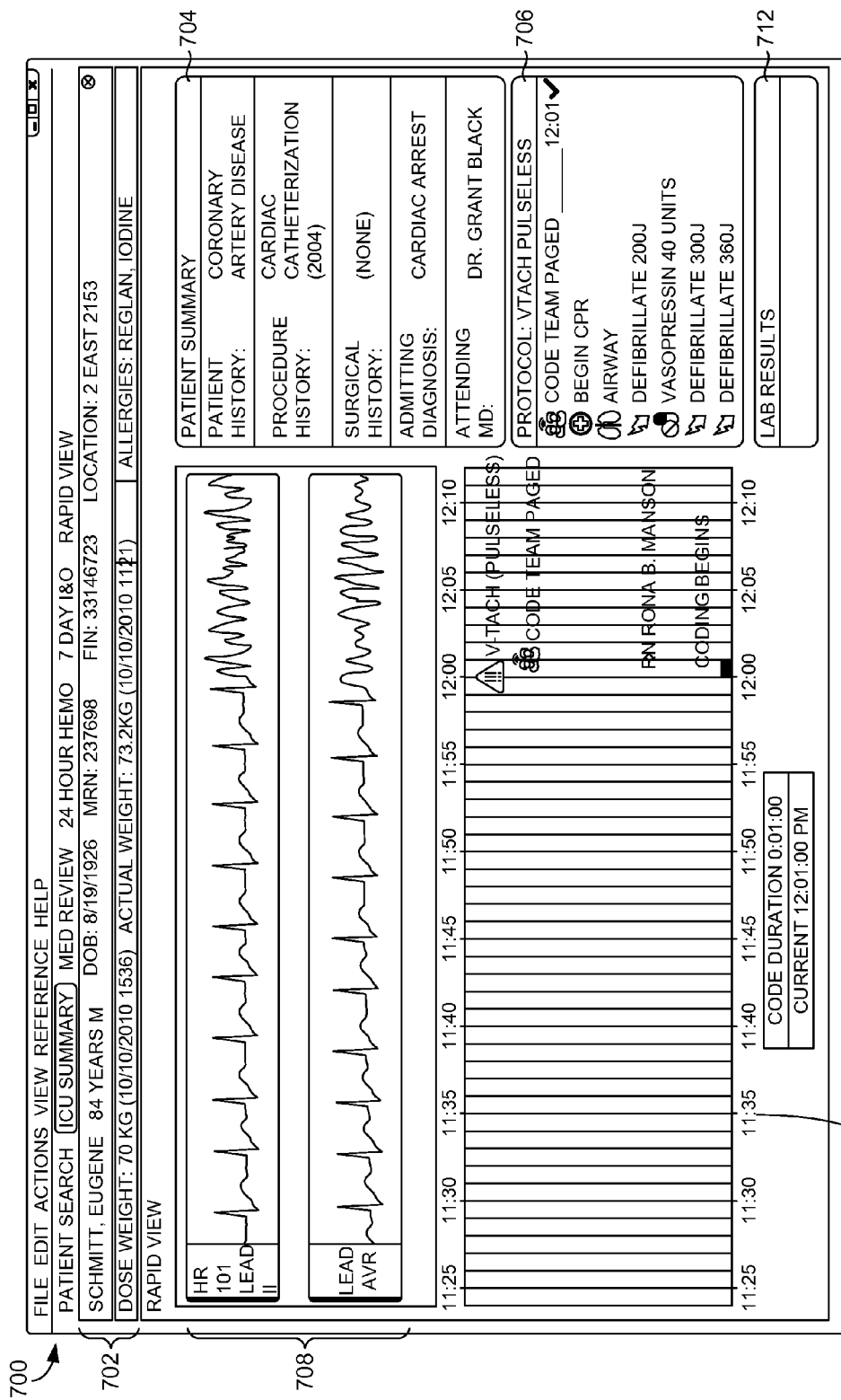
Figure 7C:
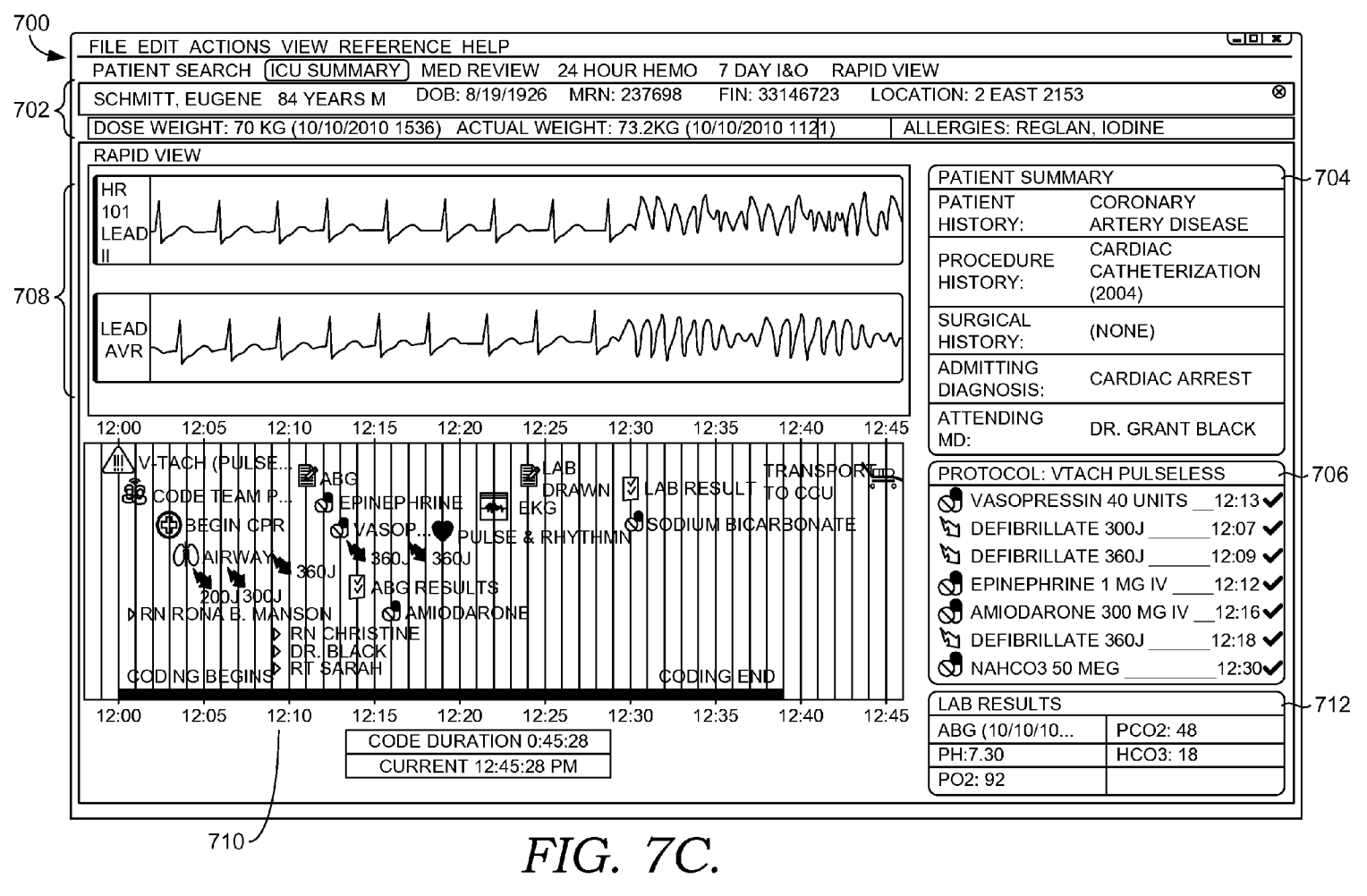

Turning to FIGS. 7A-7C, some exemplary depictions of GUIs generated by the clinician dashboard component during the code blue event are presented and are referenced generally by the numeral 700. FIGS. 7A-7C represent different times during the code blue event with FIG. 7A corresponding to the beginning of the code blue event, FIG. 7B the middle of the code blue event, and FIG. 7C corresponding to the end of the code blue event.

With respect to FIG. 7A, a general patient information area 702 contains general patient information such as, for example, patient name, patient identifier, date of birth, actual weight and dosing weight, and allergies. A patient summary area 704 includes such information as patient history, procedure history, surgical history, admitting diagnosis, and attending physician. This is just a sample of the many types of information that may be displayed in the patient summary area 704.

A protocol area 706 displays a continually updated protocol that is responsive to real-time inputs associated with the patient. In one aspect of the invention, the information displayed in the protocol area 706 includes a "suggested next care step based on patient response or incoming result." The suggested next step may be driven by a preset algorithm, a complex rules engine, or by a complex event processor monitoring transactional data from multiple sources. By way of illustrative example, the protocol area 706 initially displays a standard code blue protocol for a patient experiencing ventricular tachycardia. But as the code progresses, the heart rhythm switches from ventricular tachycardia to asystole (no heart beat). This change necessitates a completely different protocol from that used for ventricular tachycardia. Or, in another example, a lab result comes back that indicates that the patient's blood gases are outside of normal limits. The protocol area 706 dynamically changes to include unified protocol information that addresses the blood gas abnormality, the arrhythmia, and any effect the blood gas abnormality has on the arrhythmia. These are just a few of the many examples of how the protocol information updates in response to clinical event information. The protocol area 706 may also display an indication that a certain step in the protocol has been completed and a time at which it was completed.

An electrocardiogram area 708 is configured to display near real-time electrocardiogram (EKG) information associated with the patient, while a timeline area 710 displays a running timeline illustrating the clinical events that are happening with respect to the code. This information includes times at which various events occur such as, for example, a time the code blue event is initiated, a time the code blue team is paged, and a time at which various clinicians arrive in the room. In addition, the information includes the type of presenting arrhythmia and the identity of clinicians in the room. The timeline area 710 may also display a code duration time along with a current time. A lab results area 712 displays the results of labs as the information is captured by, for example, a clinician dashboard component.

FIG. 7B depicts the GUI 700 at a slightly later point in time. As can be seen in the timeline area 710, information concerning the identity and arrival of the code blue team members is documented, along with a time at which CPR was initiated, a time at which an airway was established, and when defibrillation occurred along with the energy amount of the shocks. The lab results area 712 also displays results of labs that were drawn on the patient during the code blue event.

FIG. 7C depicts the GUI 700 at a still later point in time. Besides depicting the type of information discussed above, the timeline area 710 depicts information concerning times and identities of medications administered to the patient, times at which labs were drawn, times at which lab results are received, times at which arterial blood gases were drawn and the results received, times at which a pulse and normal sinus rhythm are detected, a time when the coding protocol ends, and a time when the patient is transported to the cardiac care unit. In addition, the protocol area 706 has been updated to reflect new protocol information concerning the patient based upon responses to electrical shock, medications, and other therapeutic measures. These are just representative examples of the many types of information that can be displayed by the GUI 700. Any information pertinent to a code blue situation is contemplated to be within the scope of the invention.

At any time during the code blue event, a clinician can interact with the GUI 700. Such interaction may be via voice, touch, or gesture recognition. For example, the clinician may want to select an event occurrence on the display to access more information about that event. By way of illustrative example, the clinician touches or says the name of a medication in the timeline area 710 (i.e., vasopressin). Incident to this interaction, information is displayed concerning this medication such as dose administered, side effects, and the like.

In one aspect of the invention, an indication that the code blue event is over is triggered by a manual input. In response to the indication, the smart clinical care room transitions back to a pre-code blue scene. In one aspect of the invention, after the code blue event is over, a notification for restocking of the crash cart is automatically generated. In addition, because the crash cart was associated with the patient at the beginning of the code blue event, any charges for medications, supplies, etc. will automatically be generated and billed to the patient's account.

Figure 9:
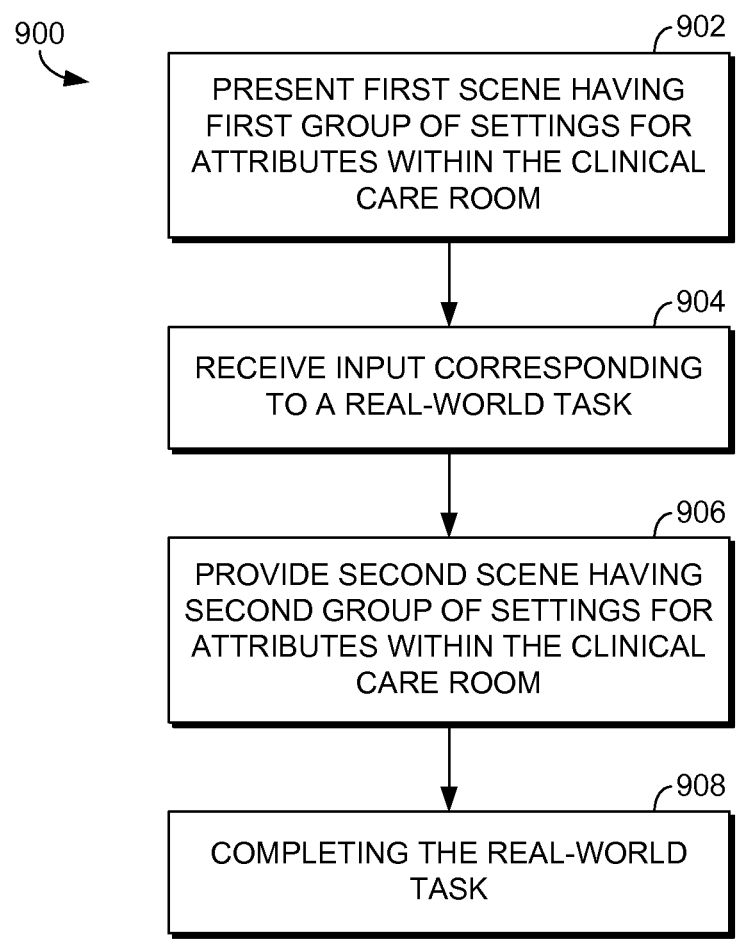
FIG. 9 depicts a flow diagram illustrating a method for transitioning a clinical care room from a first scene to a second scene in order to facilitate completion of a real-world activity suitable to implement embodiments of the present invention.

With reference to FIG. 9, a flow diagram is illustrated showing a method 900 for transitioning a clinical care room from a first scene to a second scene in order to facilitate completion of a real-world activity. At block 902, the first scene is presented in the clinical care room where the clinical care room has one or more zones. The first scene is associated with a first group of settings for components within the one or more zones. As mentioned above, the components may include any device or apparatus that impacts patient clinical care or manipulates the clinical environment in the clinical care room such as, for example, any of the components and/or interfaces of the smart room service 302 of FIG. 3. As well, the components may include any software module that provides instruction to other components. Components may also include such things as lights, television, sound system, furniture, and the like.

At block 904, an input corresponding to the real-world activity is received. As mentioned above, the input may be a manual input received from a clinician, patient, and/or family member through interaction with any of the components and/or interfaces of the smart room service, or through interaction with, for example, a patient interactive station or a clinician dashboard display device. Or the input may be an automatic input that is generated in response to a triggering event. For example, a patient monitoring device detects a heart arrhythmia and automatically generates an alert that is received as an input. The input received at step 904 corresponds to a real-world activity. There are a wide variety of examples of real-world activities, some of which were mentioned above. Some representative examples include reading, relaxation, entertainment, education, travel, personal hygiene, patient care, and the like.

At step 906, incident to receiving the input corresponding to the real-world activity, a second scene is provided. The second scene comprises a second group of setting for the components within the zones in the clinical care room. The second group of settings is different than the first group of settings. The second group of settings is optimized to facilitate completion of the real-world activity. For example, a second group of settings for a reading scene includes increasing the lighting level above a patient's bed, decreasing acoustic outputs, and positioning the bed to facilitate reading. At step 908, the real-world activity is completed.

Figure 10:
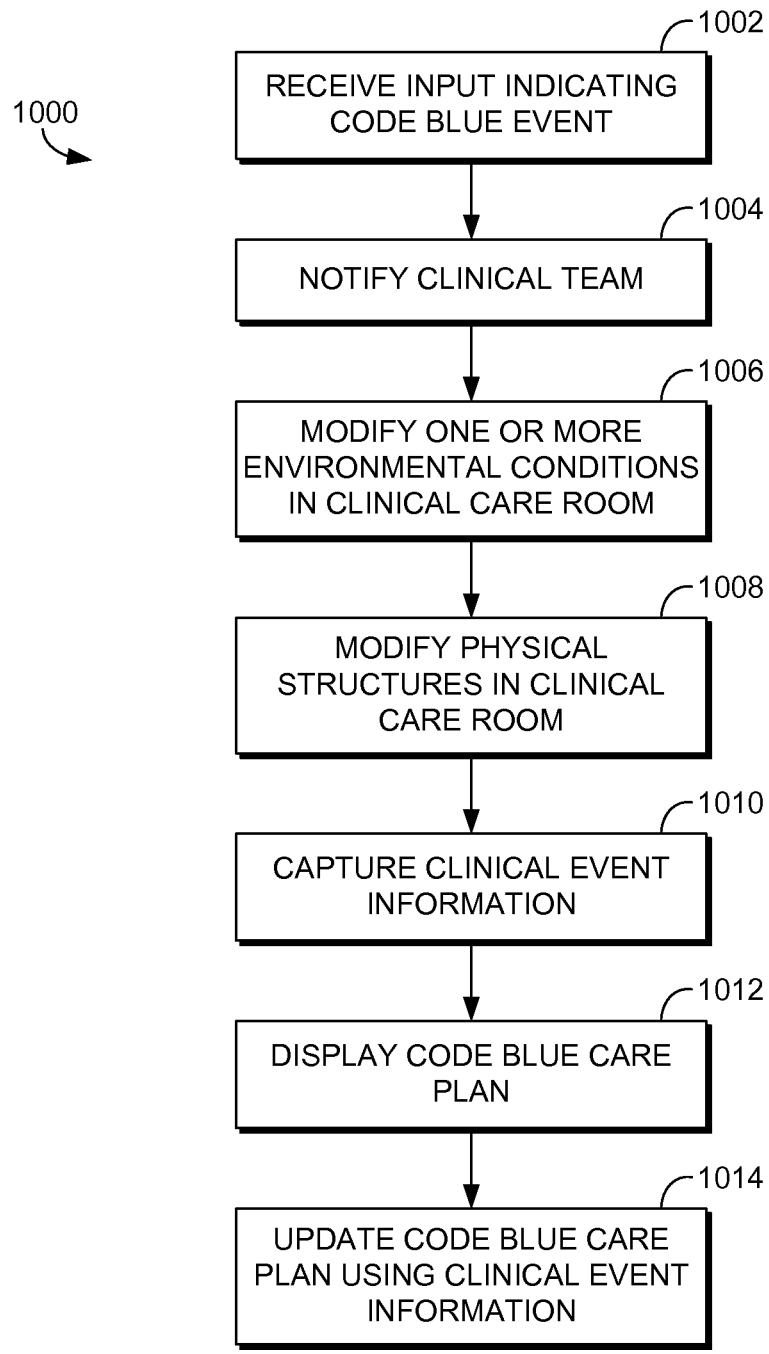
FIG. 10 depicts a flow diagram illustrating a method for adaptively utilizing a clinical care room to facilitate caring for a patient suitable to implement embodiments of the present invention.

With reference to FIG. 10, a flow diagram is depicted illustrating a method 1000 for adaptively utilizing a clinical care room to facilitate caring for a patient. At block 1002, an input is received indicating a code blue event has been initiated for the patient. At block 1004, a clinical care team is notified of the code blue event. At block 1006, one or more environmental conditions in the clinical care room are modified. One or more physical structures in the clinical care room are modified at block 1008. At block 1010, clinical event information relating to the clinical care room and the patient is captured. At block 1012, a code blue care plan is displayed to members of the clinical care team. The code blue care plan is updated using the captured clinical event information at block 1014.

Reducing Disruption During Medication Administration

Another scene of vital importance in a healthcare setting is medication administration. Medication administration begins when a clinician, in response to a medication order for a patient, retrieves the patient's medications from a medication dispensing station. Medication administration generally ends when the clinician administers the medications to the patient. Disruptions to the clinician should be kept to a minimum to reduce errors during the medication-administration process.

Figure 11:
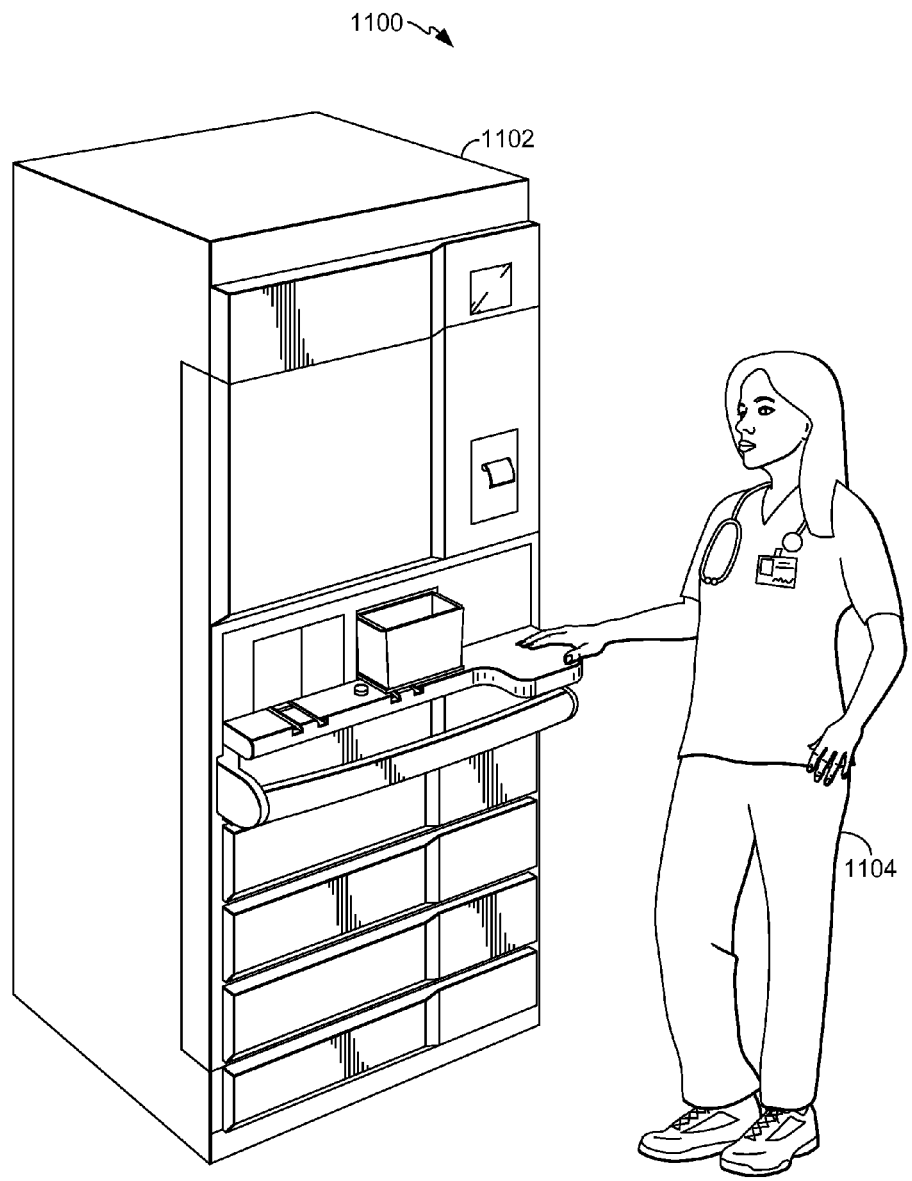
FIG. 11 depicts an exemplary scene associated with a clinician retrieving medications from a medication dispensing station suitable to implement embodiments of the present invention.

In one aspect of the invention, the medication-administration process is triggered when a clinician retrieves a patient's medications from a medication dispensing station. This triggering event is depicted in FIG. 11, and is referenced generally by the numeral 1100. FIG. 11 depicts a clinician 1104 interacting with a medication dispensing station 1102. The medication dispensing station 1102 is multi-patient oriented medical device that contains medications that are associated with one or more patients. The medication dispensing station 1102 generally contains medications for patients located in proximity to an area surrounding the medication dispensing station 1102 (e.g., patients in the same hospital wing as the medication dispensing station 1102).

The medication dispensing station 1102 generally contains multiple compartments. Each compartment is stocked with a certain medication. When the clinician 1104 wishes to begin the medication-administration process for a patient, the clinician 1104 interacts with a computer system associated with the medication dispensing station 1102 to access the medication orders for that patient (for example, the computer system may access medication orders from an electronic medical record). The computer system determines the location of the compartment that contains an ordered medication and automatically opens that compartment. Upon withdrawal of the medication by the clinician 1104, the medication is associated with the patient. This process is repeated for each ordered medication. In one aspect, the clinician 1104 may provide feedback to the computer system to verify that a specific medication has been removed from the medication dispensing station 1102. In another aspect, the medication dispensing station 1102 automatically detects when a medication(s) has been retrieved for a patient.

Because the medication dispensing station 1102 is a medical device, it is capable of communicating with a smart room service via a medical device interface or a connectivity engine (for example, the smart room service 302, the medical device interface 320, and the connectivity engine 310 of FIG. 3). Thus, when the clinician 1104 retrieves medications associated with a patient from the medication dispensing station 1102, the medical device interface receives this input, and a medication-administration process is initiated for the patient by, for example, the smart room service. The medication-administration process is initiated automatically and without human intervention.

In another aspect of the invention, the medication-administration process may be initiated upon detection of the clinician 1104 in an area where the medication dispensing station 1102 is located using a real-time location service (RTLS). For example, a sensor may be located directly above the medication dispensing station 1102. The sensor may utilize ultrasound technology, infrared technology, RFID technology, or the like to detect the presence and identity of the clinician 1104 by communicating with an identifier or badge worn by the clinician 1104. This information, in turn, is communicated to the smart room service via a sensor interface (for example, the sensor interface 322 of FIG. 3). The detection of the presence and identity of the clinician 1104 may be combined with the action of patient selection at the medication dispensing station 1102 to initiate the medication-administration process.

The medication-administration process is aborted, delayed, or cancelled if the patient is not in the clinical care room at the time the medication-administration process is initiated. For example, upon initiation of the medication-administration process, the clinician 1104 may be provided with a non-obtrusive visual notification that the patient is not currently in the clinical care room, or present in the clinical care unit. With this information, the clinician 1104 can determine if administration of medication should be delayed. This prevents the clinician 1104 from wasting valuable time gathering medications, traveling to the patient's room and discovering that the patient is not currently in the room. Alternatively, upon receiving the visual notification, the clinician 1104 may directly communicate with the department currently responsible for the patient's care and schedule a time that the patient should be returned to the clinical care room in order to receive medications. The information that the patient is not in the clinical care room may be acquired in a variety of ways.

In one aspect, a healthcare facility may have a system scheduler that tracks the schedule of all patients in the healthcare facility. For example, if a patient is scheduled for an X-ray at the same time the input is received indicating that the clinician 1104 has initiated the medication-administration process for the patient, the system scheduler automatically sends a notification to the clinician 1104 that the patient is in the X-ray department. As well, the patient receiving the medications has a personalized scheduling module that is managed by a patient interactive station component (for example, the patient interactive station component 314 of FIG. 3). The scheduling module contains schedule information unique to the patient. Again, upon receiving an input indicating that the clinician 1104 has initiated the medication-administration process for the patient, the scheduling module automatically notifies the clinician 1104 if the patient is not available because, for example, the patient has been scheduled for a procedure or test during that time.

In another aspect, RTLS may determine that the patient is not in the clinical care room and automatically notify the clinician 1104. Further, in yet another aspect, a bed in the patient room may detect that the patient is not in the bed through the use of, for example, weight sensors. The bed may communicate this information to a bed interface of a smart room service (for example, the bed interface 316 of the smart room service 302), and a notification may automatically be sent to the clinician 1104 apprising the clinician 1104 of this information.

Once the medication-administration process has been initiated, a series of events occur which help to not only minimize disruptions to the clinician 1104 during medication administration, but also to increase the efficiency of the medication-administration process. As mentioned above, clinicians face multiple demands on their time and attention during their work day. These demands come from other clinicians, patients, family members and visitors. Visual indicators are used to help alert these people that the clinician 1104 is in the midst of the medication-administration process and should not be interrupted.

Figure 12:
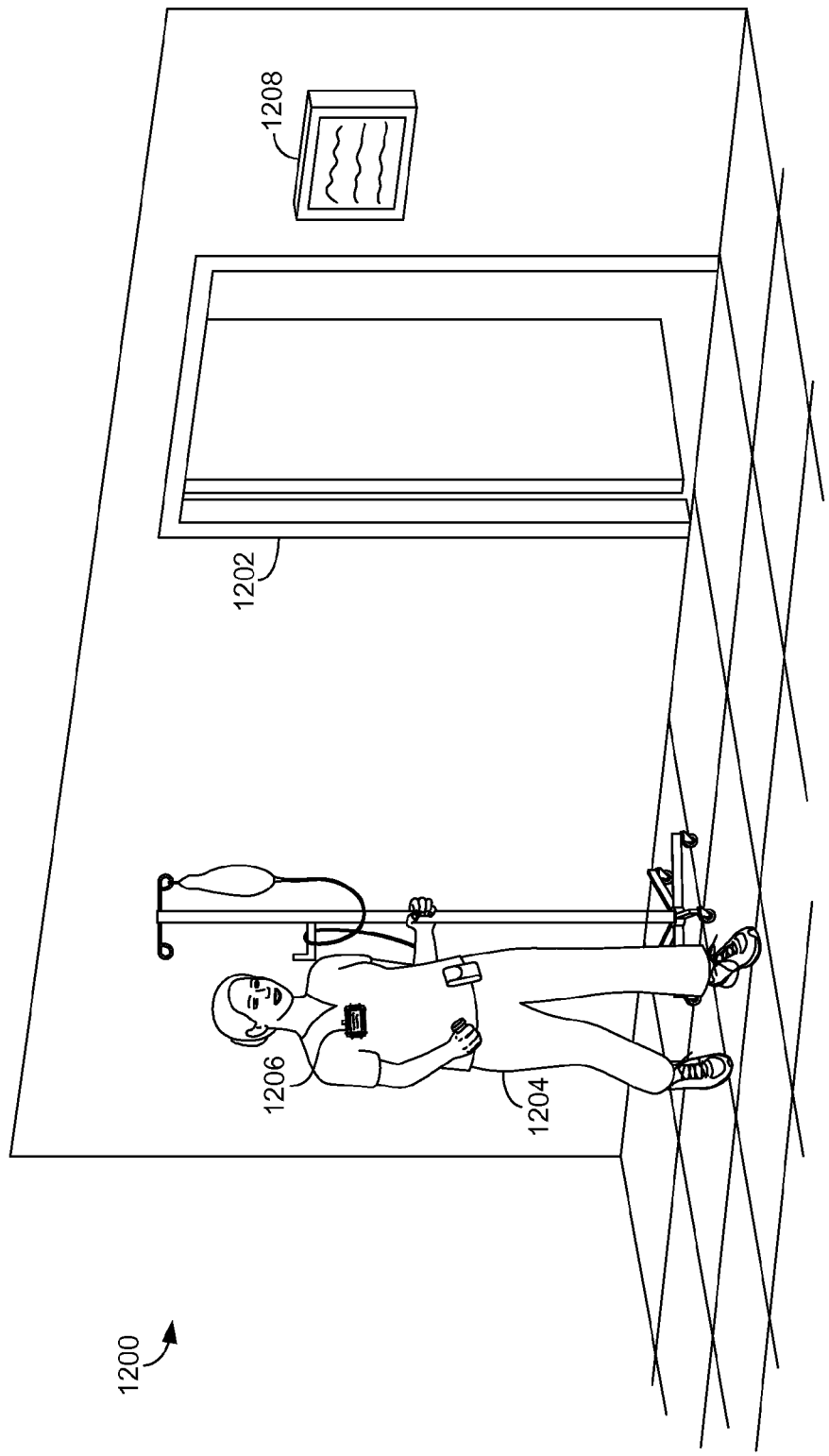
FIG. 12 depicts an exemplary scene associated with minimizing disruptions to a clinician during the medication-administration process suitable to implements embodiments of the current invention.

Turning now to FIG. 12, an exemplary scene, referenced generally by the numeral 1200, is depicted illustrating some examples of visual indicators utilized in the present invention. Scene 1200 shows a clinician 1204 during the medication-administration process (the clinician 1204 may be the same as the clinician 1104 of FIG. 11). Upon receiving an input indicating that the medication-administration process has been initiated by the clinician 1204 for a patient in a clinical care room 1202, room signage 1208 outside the entrance to the clinical care room may display a message indicating the medication-administration process is ongoing for the patient in the clinical care room 1202. In one aspect, the input may be received by an interactive room link component of a smart room service (for example, the interactive room link component 318 of the smart room service 302). Upon receiving the input, the interactive room link component may push a message out to the room signage 1208 that the medication-administration process is ongoing.

Another visual indicator is in the form of a badge or identifier 1206 worn by the clinician 1204. The badge 1206 may, in one aspect, illuminate in such a way as to alert other people that the clinician 1204 is busy with medication administration and should not be bothered. Other examples of use of the badge 1206 to alert other people include auditory alerts (e.g., an intermittent buzzing or chiming sound) and messages displayed on the badge 1206. Instead of a badge or identifier, the visual indicator may be in the form of smart phone or tablet PC. The smart phone or tablet PC may be positioned on the clinician 1204 so that it is visible to people encountering the clinician 1204. Again, the smart phone or tablet PC may illuminate, display a message, or provide auditory alerts indicating that the clinician 1204 is busy with medication administration.

Other examples of visual indicators include illumination of a nurse call dome light outside the entrance of the clinical care room 1202 as well as signage at a clinician station associated with the clinical care room 1202. The signage at the clinician station may provide information as to which clinician is involved in medication administration as well as which patient is receiving the medication(s).

Another way to reduce disruptions during the medication-administration process is to decrease the number of messages in the form of alerts and notifications received by the clinician 1204. In one aspect, all critical alerts and notifications regarding patients other than the patient in the clinical care room 1202 are routed to a back-up clinician. For example, a smart room service may determine a clinician available to act as back-up to the clinician 1204. Back-up clinicians are those clinicians not currently involved in medication administration and thus are able to address the critical alerts and notifications received by the clinician 1204 during medication administration. Further, a badge worn by the back-up clinician may illuminate to remind the back-up clinician not to begin his or her own medication-administration process until the clinician 1204 has completed the patient's medication-administration process. If a back-up clinician is unavailable, the clinician 1204 may receive a notification that the medication-administration process should be delayed until a back-up clinician becomes available.

Yet another way to reduce disruptions to the clinician 1204 during medication administration is to hold in a queue all lower priority alerts and notifications concerning patients other than the patient in the clinical care room 1202. For example, an input indicating that the medication-administration process has been initiated may be received by a communication component of a smart room service (for example, the communication component 324 of the smart room service 302 of FIG. 3). Subsequently, the communication component holds all non-critical alerts and notifications in a queue for the clinician 1204. At the end of the medication-administration process, an input is received indicating the medication-administration process is complete. At this point, the communication component releases all queued non-critical alerts and notifications to the clinician 1204.

Critical alerts and notifications may be considered alerts and notifications that directly impact a patient's care. Some examples of critical alerts include alerts that a patient is experiencing cardiopulmonary arrest, alerts that a patient is experiencing an allergic reaction to a medication, or alerts that a patient and a medical device that is important for patient care have become disassociated. Other types of critical alerts and notifications include tornado alerts, fire alerts, and the like. Non-critical alerts and notifications include alerts and notifications that either indirectly impact patient care or are independent of patient care but have some relevance to the clinician 1204. Examples of non-critical alerts and notifications include messages concerning routine patient care (e.g., patient requests for routine nursing assistance), administrative notifications, notifications regarding missed pages or telephone calls, and the like.

As mentioned earlier, the goal of efficient medication administration is to reduce disruptions between the time the medications are retrieved from a medication dispensing station and the time they are administered to the patient. Likewise, another way to reduce disruptions during medication administration is to provide a static correction to the clinician 1204 if the clinician 1204 fails to immediately travel from the medication dispensing station to the clinical care room 1202 after the medication-administration process has been initiated. In one aspect, RTLS (for example, the sensor interface 322 of the smart room service 302 of FIG. 3) can detect the location of the clinician 1204 and make a determination that the clinician 1204 has traveled to an area other than the clinical care room 1202. As mentioned earlier, RTLS makes use of sensors located throughout the health-care facility. Once it is detected that the clinician 1204 is in an area other than en route to the clinical care room 1202 or in the clinical care room 1202, a communication is sent to the badge 1206 (for example, by a communication component such as the communication component 324 of FIG. 3). The badge 1206 may buzz in response to the received communication thus alerting the clinician 1204 that the clinician 1204 needs to proceed to the clinical care room 1202. In another example, the badge 1206 may intermittently flash or ring to correct the clinician 1204.

Yet another way to improve the efficacy and safety of the medication-administration process is to increase the efficiency of the process. Increasing the efficiency of medication administration begins when a clinician removes medications for a patient from a medication dispensing station. As mentioned earlier, if it is determined that the patient is not in the clinical care room, a notification is sent to the clinician alerting the clinician to this fact, thus saving time and resources. As well, notifications related to the medication(s) may be sent to the clinician to improve efficiency. Several examples will be provided to better illustrate this aspect of the invention.

In one example, an order for intravenous (IV) administration of a certain medication may exist for the patient in the patient's electronic medical record (EMR) (for example, the EMR 304 of FIG. 3). When an input is received indicating that the clinician 1204 has initiated the medication-administration process, and it is determined that the patient requires an IV infusion, a smart room service may query a medical device interface (for example, the medical device interface 320 of FIG. 3) as to the presence and availability of the necessary medical devices in the clinical care room to administer the infusion (i.e., the presence and availability of one or more IV pumps associated with the patient, and the presence and availability of appropriate connections needed to administer the infusion). The information gathered from this query is relayed to the clinician 1204, so that the clinician 1204 can gather necessary supplies before traveling to the patient's room.

In another example, an order for a renally-excreted drug may exist in the patient's EMR. When an input is received indicating the medication-administration process has been initiated for the patient, a query may be made by, for example, a smart room service, as to lab results measuring the patient's renal function (i.e., the smart room service may query the EMR or, alternatively, the smart room service may query a medical device that generated the lab results). If the lab results indicate the patient's renal health is compromised, a notification is sent to the clinician 1204, and the clinician can begin appropriate corrective measures such as calling the ordering physician, or alerting the hospital's pharmacy staff.

Figure 13:
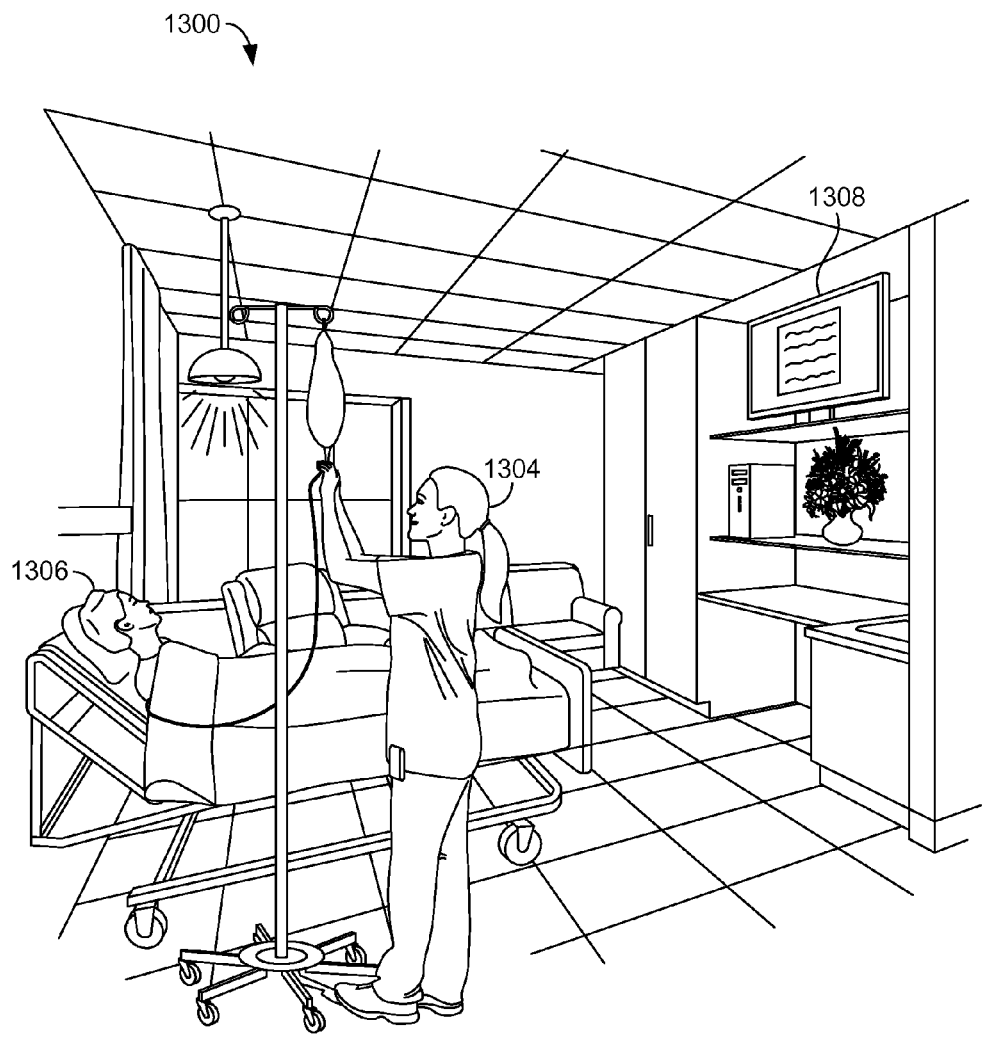
FIG. 13 depicts an exemplary scene associated with a clinician administering medications to a patient in a smart clinical care room suitable to implement embodiments of the current invention.

Another way to increase the efficiency of the medication-administration process is to prepare both the clinical care room and the patient who is to receive the medications. Some of these features are shown in FIG. 13, referenced generally by the numeral 1300, which depicts a clinician 1304 and a patient 1306 in a clinical care room. The clinician 1304 may be the same as the clinician 1204 of FIG. 12 or the clinician 1104 of FIG. 11. In one aspect, upon receiving an indication that the medication-administration process has been initiated for the patient 1306, the clinical care room is prepared by illuminating an area over the patient's bed by utilizing an environmental module of a patient interactive station component (for example, the patient interactive station component 314 of FIG. 3). As well, televisions may be powered off or muted or music volume may be lowered by utilizing the services of a television module or a music module of the patient interactive station component. Additionally, display screens such as a clinician dashboard display device and a patient interactive station 1308 may be powered up to a ready position.

In one aspect, the patient interactive station 1308 may display an alert informing the patient 1306 and the patient's visitors that the clinician 1304 will be arriving shortly to administer the medications. Educational information regarding the medications the patient 1306 will be receiving may also be displayed on the patient interactive station 1308. If this is the first time the patient 1306 is receiving the medication, an informed consent form may be displayed on the screen along with informational material regarding the new medication. This allows the patient 1306 an opportunity to review the materials before the clinician 1304 arrives in the clinical care room.

Upon receiving the indication that the medication-administration process has been initiated, a bed in the clinical care room may automatically adjust to a position that facilitates medication administration. This may be done by utilizing a bed interface such as, for example, the bed interface 316 of FIG. 3. In one aspect, the position of the bed is dependent upon an identity of the medication to be administered to the patient 1306. For example, if the patient 1306 is required to swallow a pill, the head of the bed may be elevated such that the patient's upper body is significantly elevated. But if the patient 1306 is going to receive an IV infusion over a substantial period of time, the head of the bed may be elevated only slightly so that the patient 1306 is comfortable during the infusion.

In one aspect of the invention, settings for multiple components within the clinical care room may be tailored based upon the type of medication the patient 1306 is receiving. For instance, the patient 1306 may be receiving chemotherapy for cancer treatment. This is often an emotional experience for patients, and the clinical care room can be modified to help ease anxiety. The lighting in the room may be set to a low level, aromatherapy can be initiated by utilizing an aromatherapy module of the patient interactive station component, and relaxing music can be played. Additionally, a scene module of the patient interactive station component can display a soothing scene on a digital window or digital ceiling present in the clinical care room.

Certain medical devices other than the patient's bed may also be prepared upon receiving the indication that the medication-administration process has been initiated. For instance, some medications are delivered via a patient's respirator. If an indication is received that a medication is to be delivered via the respirator, the respirator settings may automatically adjust (e.g., slowing the rate of respiration, or increasing the depth of respiration) to facilitate administration. Additionally, if a patient is scheduled to receive dialysis and the dialysis machine is present in the clinical care room, the dialysis machine may automatically adjust (e.g., warming of the dialysis solution) to facilitate the dialysis process. In yet another example, upon receiving an indication that a medication is to be administered via an IV infusion pump, the IV infusion pump may automatically turn on, and the dosage may be automatically entered along with an infusion rate and a stop time.

Returning to FIG. 13, once the clinician 1304 has arrived in the clinical care room and has verified that the correct medication is being delivered to the correct patient 1306 through the use of, for example, bar codes or RFID tags on the medication, the patient 1306, and the clinician 1304, the clinician 1304 begins medication administration. The various medical devices present in the clinical care room work together to ensure that the medication-administration process is efficient and safe. For example, an IV infusion pump may be in communication with a patient monitoring device through a medical device interface or a connectivity engine (for example, the medical device interface 320 and the connectivity engine 310 of FIG. 3). If the medication being administered through the IV infusion pump causes a precipitous drop in heart rate or blood pressure, the patient monitoring device may communicate this information to the IV infusion pump, and the IV infusion pump would slow administration of the medication. As well, an alert is generated and sent to the clinician 1304 informing the clinician 1304 of this information.

In another example, the patient 1306 may be receiving a blood transfusion through an IV infusion pump. The patient 1306 may experience an adverse reaction to the transfusion manifested by an increased heart rate and sweating. The patient's bed detects the sweating through the use of moisture sensors, and a patient monitoring device detects the increased heart rate. Both pieces of information are relayed to the IV infusion pump via a medical device interface, and the transfusion is stopped and the clinician 1304 alerted.

Once the clinician 1304 has completed the medication-administration process, an input is received indicating the medication-administration process is complete. The input may be a manual input by the clinician 1304 utilizing, for example, a clinician dashboard display device. Or the input may automatically be received by, for example, an IV infusion pump or other medical device detecting that the medication has been completely administered. In one aspect of the invention, once the input is received indicating that the medication-administration process is complete, the clinical care room may automatically return to its pre-medication administration state.

The completion point of the medication-administration process may vary in different aspects of the invention. For example, with reference to the clinician 1304, the medication-administration process is complete when an IV is established and the medication infusion has begun; the clinician 1304 may then be available to treat other patients or perform other tasks. With reference to smart room functions, the medication-administration process is complete when the medication is fully infused through an IV. In yet another aspect, the completion of the medication-administration process may be dependent upon what type of medication is being administered to the patient 1306. For example, if the medication is a pill that needs to be swallowed, medication administration is complete once the pill is swallowed by the patient 1306. But if the medication is considered toxic and requires an IV infusion, medication administration is not complete until the clinician 1304 has observed and monitored the patient 1306 during the period of time the medication is infusing and for a period of time after the infusion is complete.

Figure 14:
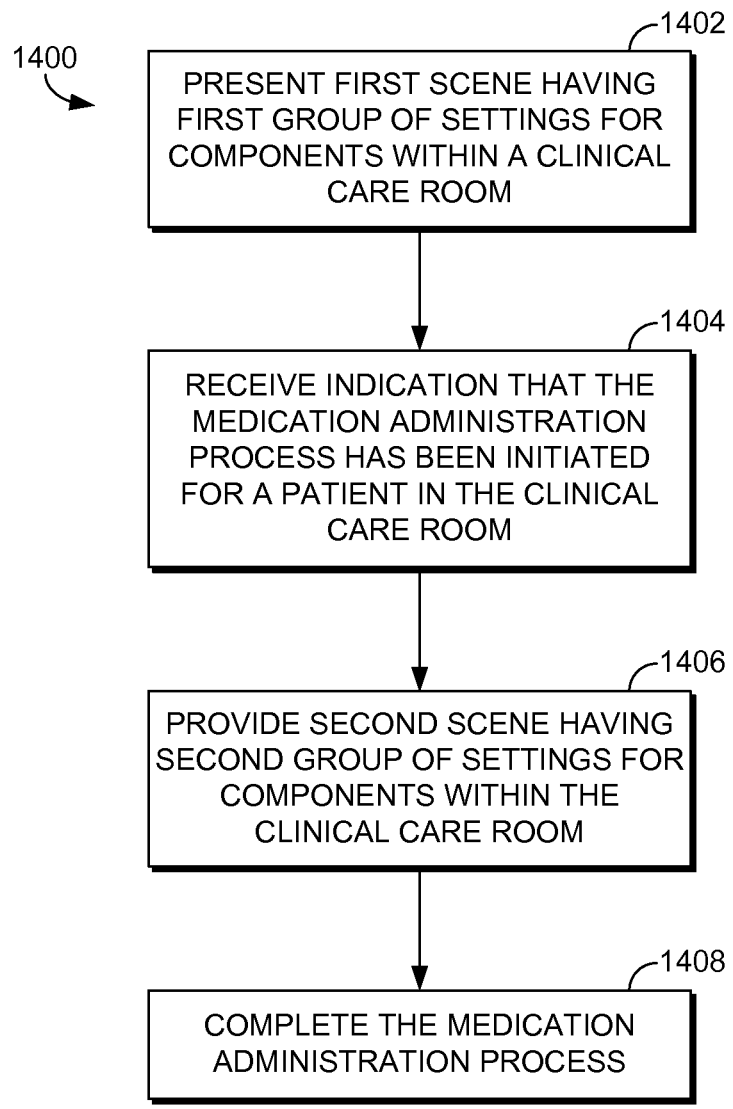
FIG. 14 depicts a flow diagram illustrating a method for preparing a clinical care room for medication administration according to an embodiment of the current invention.

Turning now to FIG. 14, a flow diagram is depicted illustrating a method for preparing a clinical care room for the medication-administration process. The method is referenced generally by the numeral 1400. At a step 1402, a first scene is presented having a first group of settings for components within the clinical care room. The first scene may be any scene associated with a patient in a clinical care room. Some examples include a reading scene, a television watching scene, or a sleeping scene. Each of these exemplary scenes is associated with different setting for components with the clinical care room. For example, the reading scene may have the lights fully illuminated, the television powered off, the music turned low, and the display screens on standby.

At a step 1404, an input is received indicating that the medication-administration process has been initiated for the patient in the clinical care room. The input may be received subsequent to an interaction between a clinician and a medication dispensing station containing medications for the patient. The input may be received by, for example, a medical device interface, a sensor interface or a connectivity engine of a smart room service. It may be determined that the patient is not in the clinical care room at the time the input is received by use of RTLS sensors or weight sensors in the patient's bed. If it is determined that the patient is not in the clinical care room, a notification may be sent to the clinician via a communication component of the smart room service.

At a step 1406, incident to receiving the input indicating the medication-administration process has been initiated, a second scene is provided having a second group of settings for the components within the clinical care room. In one aspect, the second scene may be dependent upon the type of medication to be administered to the patient. Examples of settings include illuminating the area over the patient's bed, bringing display devices to a ready position, adjusting a position of the patient's bed, powering off televisions, muting music, displaying educational materials regarding the medications, displaying informed consent forms, notifying the patient that the clinician will be arriving shortly, preparing medical devices that will be utilized during medication administration, and the like. All of these changes or modifications to the clinical care room facilitate completion of the medication-administration process as shown in a step 1408.

Figure 15:
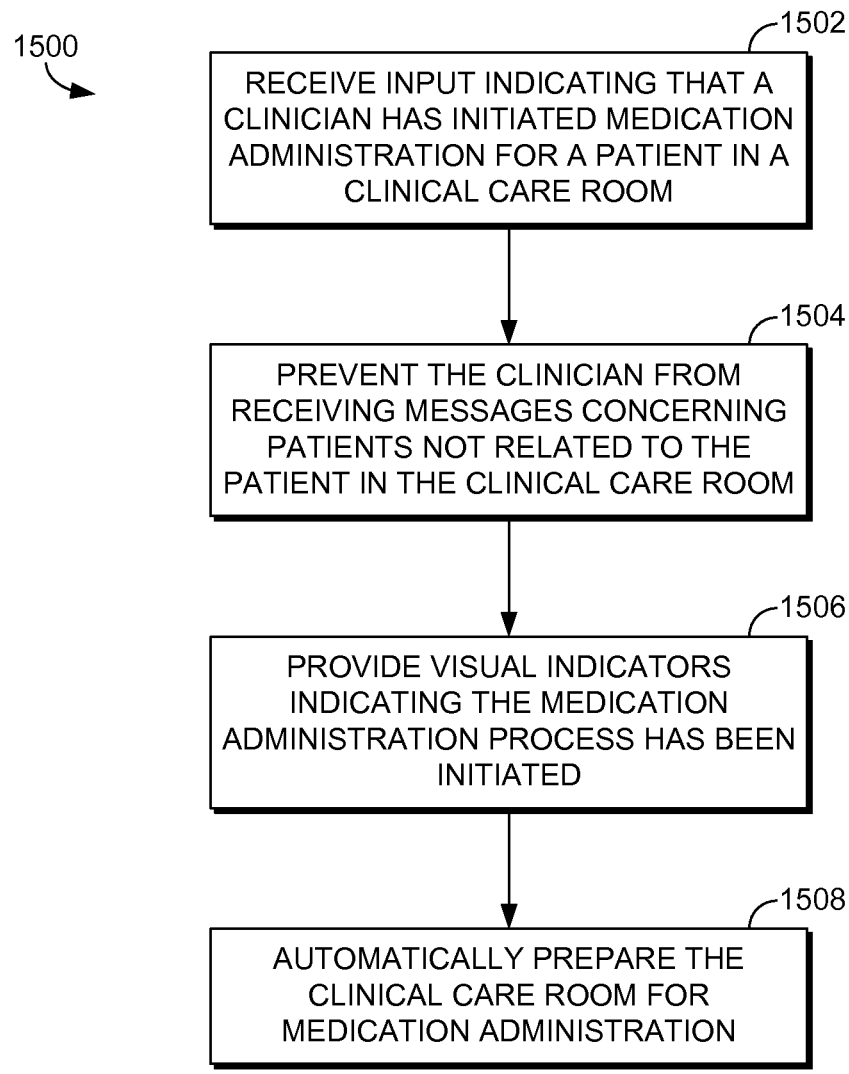
FIG. 15 depicts a flow diagram illustrating a method for minimizing disruptions to a clinician during a medication-administration process according to an embodiment of the current invention.

Turning to FIG. 15, a flow diagram is depicted illustrating a method of reducing disruptions to a clinician during the medication-administration process. At a step 1502, an input is received indicating that the clinician has initiated the medication-administration process for a patient in a clinical care room. In one aspect, the input may be received subsequent to an interaction between the clinician and a medication dispensing station. In another aspect, the input may be received upon detection by an RTLS sensor that the clinician is in an area in front of the medication dispensing station.

At a step 1504, and incident to receiving the indication that the medication-administration process has been initiated, the clinician is prevented from receiving messages concerning patients and other matters not related to the patient in the clinical care room. In one aspect, all non-patient related critical messages in the form of alerts and notifications are routed to a back-up clinician or to a clinician station associated with the clinical care room. Still further, all non-critical alerts and notifications are held in queue for the clinician until the medication-administration process is completed.

At a step 1506, one or more visual indicators are provided indicating that the medication-administration process has been initiated. The visual indicators alert other clinicians, patients, and visitors that the medication-administration process is ongoing, and the clinician should not be disturbed. The visual indicators may include room signage outside the clinical care room that displays an alerting message, a nurse call dome light outside the patient's room, signage at the clinician station associated with the clinical care room, and a badge worn by the clinician that may illuminate during the medication-administration process. At a step 1508, the clinical care room is automatically prepared for medication administration. Such preparation includes adjusting the lighting, the television, display devices, medical devices, the patient bed, music, and the like.

The present invention is designed to improve the efficacy and safety of the medication-administration process by reducing disruptions to the clinician while the clinician is actively involved in medication administration. Further, efficacy is improved by preparing the patient and the clinical care room upon receiving an indication that the medication-administration process has been initiated.

Ambient Sensing of Patient Discomfort

An embodiment of the present invention uses ambient sensing to detect patient discomfort and to initiate early intervention strategies designed to minimize the discomfort. This embodiment may be described throughout the present specification as a pain management scene or process. For a number of different reasons (e.g., patient reluctance to bother clinicians, overburdened clinicians, and lack of knowledge on the part of the patient regarding pain control), patient pain is often not detected at a point where it can be effectively managed.

Figure 16:
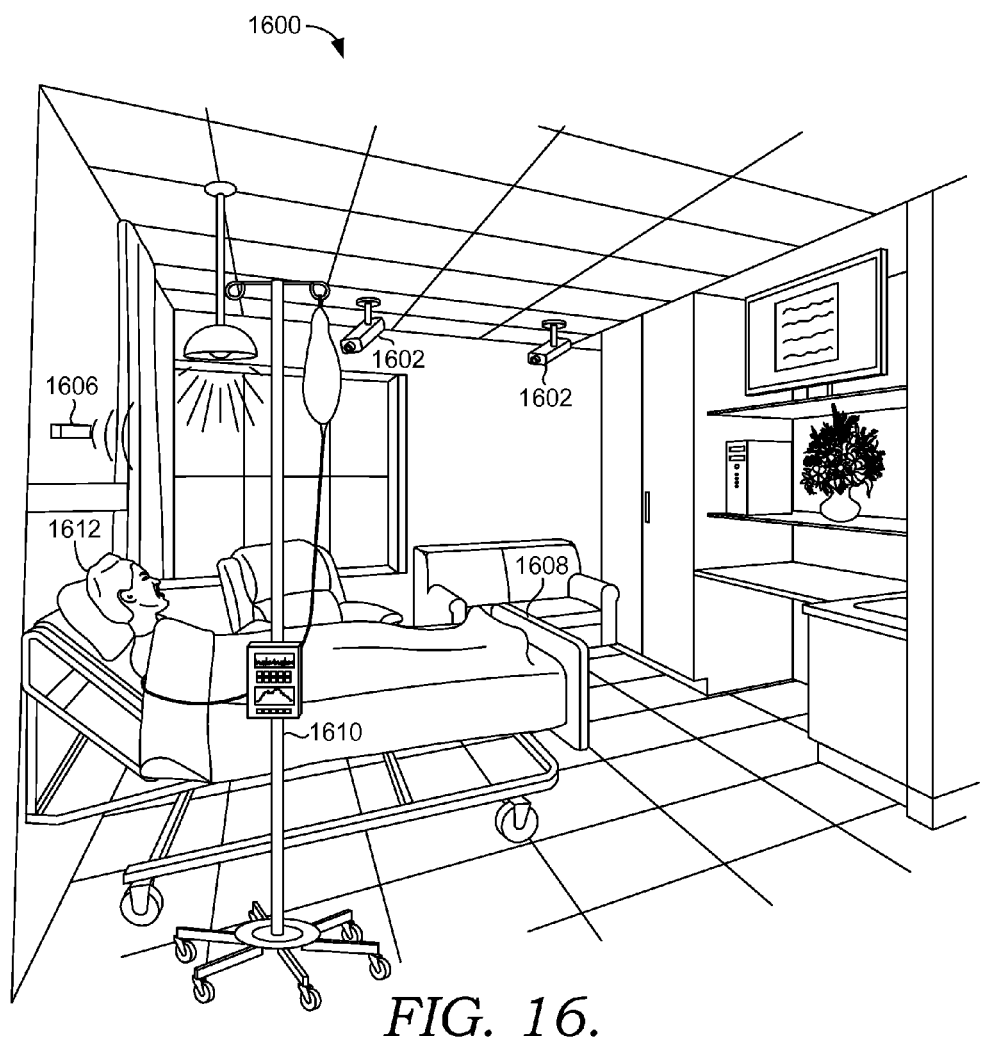
FIG. 16 depicts an exemplary scene illustrating ambient sensors in a clinical care room used to sense patient discomfort suitable to implement embodiments of the current invention.

The pain management process is triggered upon receiving inputs from ambient sensors located in a clinical care room that indicate that the patient in the room is experiencing discomfort or pain. FIG. 16 depicts a pain management scene 1600, in accordance with an embodiment of the present invention. FIG. 16 depicts a number of ambient sensors used to detect patient discomfort. The ambient sensors may include cameras 1602, audio sensors 1606, vital signs monitors 1610, and moisture sensors (not shown) and weights sensors (not shown) incorporated into a patient bed 1608. In one aspect, the cameras 1602 may comprise Web cameras, digital cameras, depth cameras, and the like. There may be a single camera 1602 or multiple cameras 1602. Further, if there are multiple cameras, each camera may be positioned differently from the other cameras, and each camera may serve a unique purpose. Any and all such variations are within the scope of embodiments of the present invention.

The camera(s) 1602 is used to monitor facial expressions of a patient 1612 in order to detect discomfort. To effectively monitor facial expressions, the camera 1602 is positioned on the ceiling over the bed 1608. The camera 1602 may also be positioned on the head wall (the wall at the head of the bed) or at other various locations throughout the room so long as the camera 1602 has a generally unobstructed view of the patient's face.

The camera 1602 may be programmed to monitor a facial image of the patient 1612 at preset intervals (i.e., every five minutes, every ten minutes, etc.). Alternatively, the camera 1602 may be triggered to monitor a facial image of the patient 1612 upon receiving an indication from one of the other ambient sensors. For instance, the vital signs monitor 1610 may detect that the patient's heart rate and respiratory rate have increased compared to the patient's baseline values; these may be signs that the patient 1612 is experiencing discomfort. This information is communicated to, for example, a connectivity engine that is part of a smart room service. The connectivity engine and smart room service may be the connectivity engine 310 and the smart room service 302 of FIG. 3. Upon receiving the information, the connectivity engine triggers the camera 1602 to capture an image of the patient's face.

Once an image is captured by the camera 1602, it is communicated to a sensor interface of the smart room service such as the sensor interface 322 of FIG. 3. The sensor interface is configured to apply an algorithm to the image in order to recognize facial gestures or expressions indicating discomfort. Once a facial gesture indicating discomfort is recognized from the image, the sensor interface compares the facial gesture to a stored image representing the normal resting face of the patient 1612 in order to gauge the severity of the discomfort.

The camera 1602 may also be used to monitor a location and position of the patient 1612 and any movement associated with the patient 1612. The camera 1602 may also be used to monitor the location, position, and movement of other family members or friends present in the clinical care room. As such, the camera 1602 is positioned on the ceiling of the room over the patient's bed 1608. Other cameras 1602 may be positioned at other locations in the room to monitor family members and friends located in a family/friend zone such as the family/friend zone 202 of FIG. 2.

Like above, the camera 1602 may be programmed to monitor the location, position, and movement of the patient 1612 at preset intervals (i.e., every five minutes, every ten minutes, etc.). Alternatively, the camera 1602 may be triggered to monitor the location, position, and movement of the patient 1612 upon receiving an indication from one of the other ambient sensors. For example, weight sensors in the patient's bed 1608 may sense that the patient is no longer in the bed. This information is communicated to the connectivity engine (via a bed or sensor interface), which, in turn, triggers some or all of the cameras 1602 to capture images from different parts of the room in order to localize the patient 1612. Depth cameras are especially suited for this type of monitoring. Depth cameras, also known as a range camera, a 3D camera, a time-of-flight camera, and/or a RGB-D camera, transmits near-infrared light and measure its "time-of-flight" after it reflects off objects.

The location, position, and movement data captured by the camera 1602 is transmitted to the sensor interface which processes the data to render three-dimensional images. The camera 1602 is able to distinguish human body parts, joints, and movements, as well as distinguish one human face from another. As such, the camera 1602 may be used to determine whether the patient 1612 is agitated (increased body movements), whether the patient 1612 is in imminent danger of falling (unsteady gait, positioned near the edge of the bed with no guard rails up), or whether the patient 1612 has fallen (patient lying on the floor of the room). Further, the camera 1602 may be used to distinguish the patient's location and movements from other people present in the room. The camera 1602 may also be used to detect if friends or family members in the clinical care room appear agitated, distressed, or hurt (i.e., lying on the floor) and need attention.

In one aspect, this data is compared to baseline camera data stored in association with the patient 1612 in order to determine if the patient's location, position, or movements indicate discomfort. For instance, if the patient 1612 is normally restless, data from the camera 1602 indicating movement may not be indicative of discomfort. However, data from the camera 1602 indicating that the patient 1612 is lying on the floor would indicate discomfort or a fall. The comparison of current data with baseline data is used to determine the presence and/or severity level of discomfort.

The audio sensors 1606 are used to capture articulations of the patient 1612 that may indicate discomfort. For instance, the audio sensors 1606 are configured to capture coughing, groaning, crying, moaning, and the like but not normal conversations. This information is received by the sensor interface. Again, the sensor interface compares the received data to baseline articulation data stored in association with the patient to determine if the patient is experiencing discomfort. Further, the sensor interface may determine a severity level of the discomfort based on the amount of variance of the current pattern of articulations as compared to the baseline articulation data.

The bed 1608 contains weight and moisture sensors that aid in detecting patient discomfort. For instance, the moisture sensors may detect increased patient perspiration indicating distress or discomfort. Weight sensors may detect fluctuations in the patient's weight over different parts of the bed 1608. For instance, agitated patients may shift their weight frequently across different parts of the bed 1608; the weight sensors are used to detect this type of movement. The weight sensors are also used to detect if the patient 1612 is not currently in the bed 1608 or if the patient's weight is distributed along the edge of the bed 1608 indicating that the patient 1612 is at risk of falling out of the bed.

Information detected by the weight and moisture sensors is received by, for example, the sensor interface and/or a bed interface such as the bed interface 316 of FIG. 3. The sensor and/or bed interface is configured to compare the received data with baseline patient data stored in, for example, an electronic medical record (EMR) such as the EMR 304 of FIG. 3, to determine if the patient 1612 is experiencing discomfort. The baseline patient data may include baseline moisture sensing data for the patient 1612, as well as baseline weight fluctuation patterns for the patient 1612. Based on this comparison, the sensor and/or bed interface determines a severity level of the discomfort.

Additionally, the EMR contains clinical care plans for the patient 1612. The clinical care plans can be accessed to determine if there is any movement restrictions associated with the patient 1612. For instance, a clinical care plan may indicate that the patient 1612 is at risk of falls due to confusion. Therefore, if weight sensor data indicates that the patient's weight is distributed within a certain proximity of the edge of the bed 1608, or if depth camera data indicates that the patient 1612 is positioned near the edge of the bed 1608, certain actions may be automatically initiated such as raising guard rails if they are not currently raised and notifying clinicians.

The vital signs monitor 1610 is used to monitor the patient's vital signs for indications of discomfort. When a patient is experiencing pain, the patient's heart rate and respiratory rate often become elevated. This information is received by, for example, the sensor interface and/or a medical device interface, such as the medical device interface 320 of FIG. 3. The sensor and/or medical device interface is configured to compare the received vital signs data to baseline vital signs data in the patient's EMR to determine if the patient 1612 may be experiencing discomfort. Further, the sensor and/or medical device interface is further configured to determine a severity level of the discomfort based on the amount of variance between the received vital signs data and the baseline vital signs data.

Ambient sensors may also include a real-time-location system (RTLS) (not shown in FIG. 16). As outlined above, RTLS utilizes sensors to detect radio-frequency identification (RFID) tags worn by patients and clinicians in order to determine a location and identity of the patient and/or clinician. In one aspect, RTLS is able to triangulate the sensors to determine if the patient 1612 is located on the floor of the room.

As discussed, the various ambient sensors monitor the patient and the clinical care room. Inputs from the ambient sensors are compared to predetermined thresholds in order to determine if the patient is experiencing discomfort. In one aspect, the predetermined thresholds are derived from data from the general population as a whole, or, in another aspect, the predetermined thresholds are derived from baseline values stored in association with the patient (i.e., stored in the patient's EMR). A severity level for each input is determined based on the amount of variance between the received input and the threshold value. In turn, a combined severity level of the discomfort is determined by aggregating individual severity levels associated with each of the inputs.

In one aspect of the invention, a patient is determined to be experiencing discomfort if only one input from the ambient sensors exceeds a respective predetermined threshold. In another aspect, patient discomfort is based on a combination of inputs exceeding respective thresholds. In still another aspect, a determination of patient discomfort is based on all of the inputs exceeding respective thresholds. In yet another aspect, a determination of patient discomfort may be based on a single or combined severity level that exceeds a given threshold. Any and all such variations are within the scope of embodiments of the current invention.

Once it is determined that the patient is experiencing discomfort or pain, various actions are automatically initiated by the smart room service. A communication component of the smart room service (such as the communication component 324 of FIG. 3) communicates a message indicating the patient's discomfort to a message queue associated with a clinician. Depending on the combined severity level, the message is placed higher in the message queue so as to be delivered to the clinician sooner. The message may include the combined severity level to better guide the clinician's decision as to how urgently the situation needs to be addressed. A message indicating the patient's discomfort may also be displayed on a digital room sign located outside the entrance to the clinical care room. For instance, the sensor interface communicates data indicating patient discomfort to an interactive room link component of the smart room service, such as the interactive room link component 318 of FIG. 3. In turn, the interactive room link component displays a message on the digital room sign. Further, the communication component may automatically establish a communication portal between the patient's room and a clinician and/or a clinician work center allowing two-way communication between the patient and clinicians.

Figure 17:
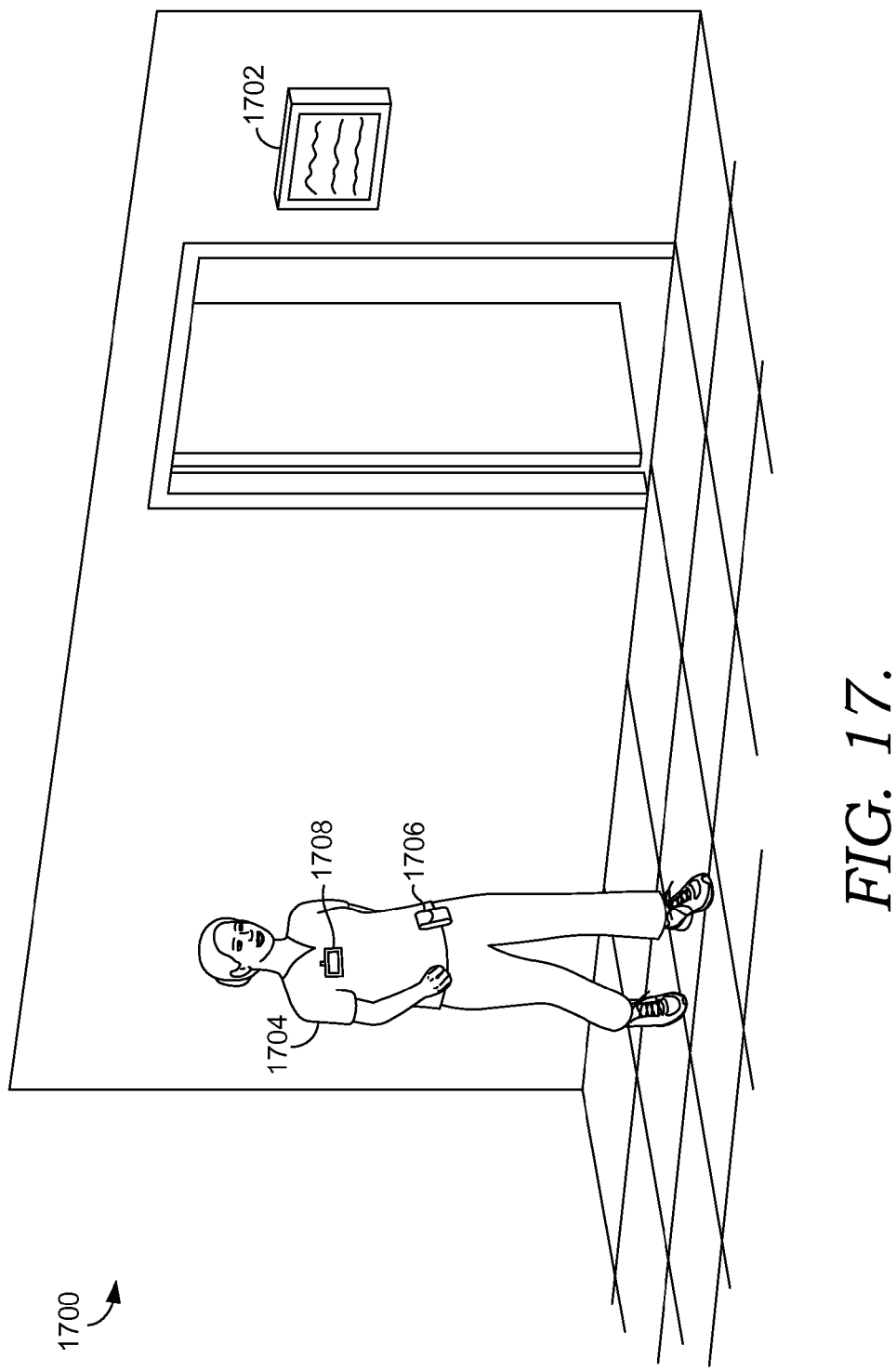
FIG. 17 depicts an exemplary scene illustrating notifications and alerts indicating that a patient is experiencing discomfort suitable to implement embodiments of the current invention.

FIG. 17 depicts an exemplary scene 1700 illustrating various notifications and alerts indicating that the patient is experiencing discomfort. A clinician 1704 receives a notification via a mobile device or pager 1706. The notification may include patient identifying information, a room number, a message indicating that the patient is experiencing discomfort, and/or a severity level associated with the discomfort. Additionally, depending on the severity level associated with the discomfort, a badge 1708 worn by the clinician may begin flashing, buzzing, vibrating, and the like to indicate that the clinician 1704 should proceed immediately to the room. Various aspects of the badge were discussed above with respect to reducing disruptions during medication administration.

Other actions designed to minimize patient discomfort are also automatically initiated upon determining that the patient is experiencing discomfort. These include different therapies that have been pre-selected by the patient. Upon being admitted to a healthcare facility, the patient may have selected various pain management protocols or therapies using, for example, a patient interactive station. These therapies may include aromatherapy where various patient-selected plant oils and other aromatic compounds are automatically dispersed in the room. The trigger for dispersion comes from a patient interactive station component of the smart room service, such as the patient interactive station component 314 of FIG. 3, upon receiving an indication via, for example, the sensor interface that the patient is experiencing discomfort.

Other therapies initiated by the patient interactive station component may include audio therapy and/or visual therapy. Audio therapy includes the automatic playing of pre-selected sounds such as white noise, thunderstorms, rain, waves, and the like, or the automatic playing of pre-selected music. Visual therapy includes the displaying of pre-selected scenes on a digital ceiling or digital window associated with the room. Additionally, images may be displayed on a television module and overhead lights may be dimmed or turned off.

Further, a camera may have captured data indicating that a family member who has been trained by the hospital staff in relaxation therapies is present with the patient. Using the communication portal discussed earlier, a clinician may instruct the family member to initiate the relaxation therapies with the patient (breathing exercises, biofeedback coaching, stretching exercises, and the like).

Figure 18:
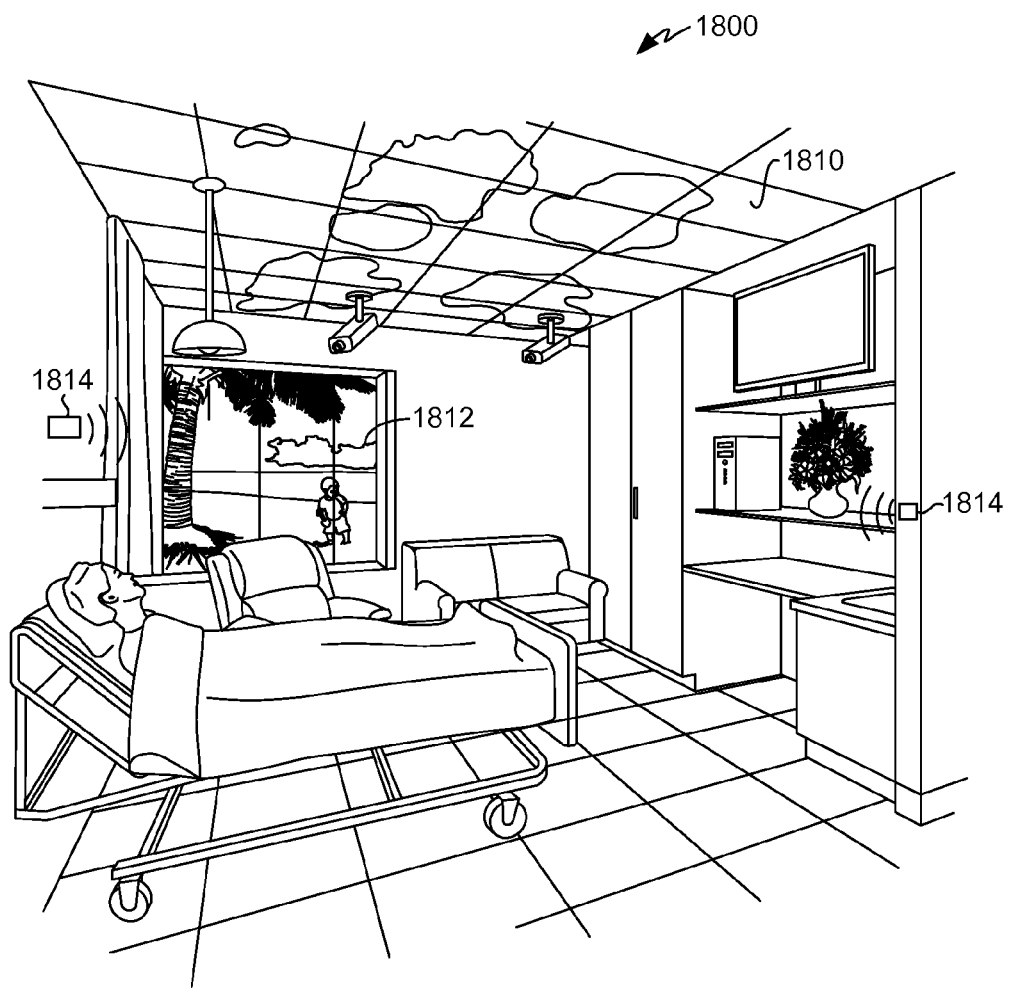
FIG. 18 depicts an exemplary scene illustrating various therapies utilized to minimize patient discomfort suitable to implement embodiments of the current invention.

FIG. 18 depicts an exemplary scene 1800 illustrating various therapies initiated upon a determination that the patient is experiencing discomfort. The scene 1800 depicts a digital ceiling 1810 displaying a pre-selected cloud scene while a digital window 1812 displays a pre-selected beach scene. The overhead light in the room has been turned off, and speakers 1814 are playing pre-selected music. All of these measures are designed to comfort the patient and to minimize pain that the patient is feeling.

Additionally, medical devices such as a patient-controlled-analgesia (PCA) pump may be automatically pre-programmed to administer pain relief. PCA pumps enable patients to self-administer pain relief when needed. These systems are effective when the patient understands how the system works and has the physical strength and dexterity to press the button that delivers the analgesic. However, in those situations when patients lack these requisite capacities, PCA pumps are not effectively utilized. The present invention aids in the effective utilization of these devices.

In one aspect, the technology supplier, the PCA pump manufacturer, the governing body of the healthcare facility, and/or certain state or federal regulations may require that verification and authorization be received from a clinician prior to the automatic administration of pain relief. In another aspect, the technology supplier, the PCA pump manufacturer, the governing body of the healthcare facility, and/or certain state or federal regulations may authorize the automatic administration of pain relief without clinician verification and authorization as long as procedures are in place to protect the safety of the patient. Some examples of procedures to ensure patient safety include sending a notification to a clinician after pain relief is administered, frequent monitoring of the patient by a clinician after pain relief has been administered, and automatically programming vital signs monitors to capture vital signs of the patient more frequently than usual.

With regard to the automatic administration of pain relief, after a determination is made that the patient is experiencing discomfort and the combined severity level exceeds a given threshold, the medical device interface determines that current vital signs associated with the patient fall within pre-set parameters. For example, it may be determined that the patient's heart rate, oxygen saturation, and respiratory rate are above a certain minimum threshold; the certain minimum threshold may have been preset by a clinician. The patient's EMR is accessed to determine that a predetermined time period has passed since pain relief was last administered, identify what dosage of pain relief was last administered, and determine if appropriate safety measures are in place. Based on these determinations an appropriate dosage of analgesic is automatically administered to the patient by the PCA pump. Once the dosage of analgesic is administered, the patient is monitored as outlined above to ensure patient safety.

Settings of other medical devices may also be adjusted to diminish patient discomfort. For instance, a patient is receiving an infusion, and the patient begins to experience a negative reaction to the infusion. This may be manifested by alterations in the patient's normal heart rate and respirations, sweating, agitation, and facial expressions indicating discomfort or anxiety. Using the ambient sensors discussed above, it is determined that the patient is experiencing a negative reaction to the infusion, and the system automatically terminates the infusion and notifies the caregiver.

Figure 19:
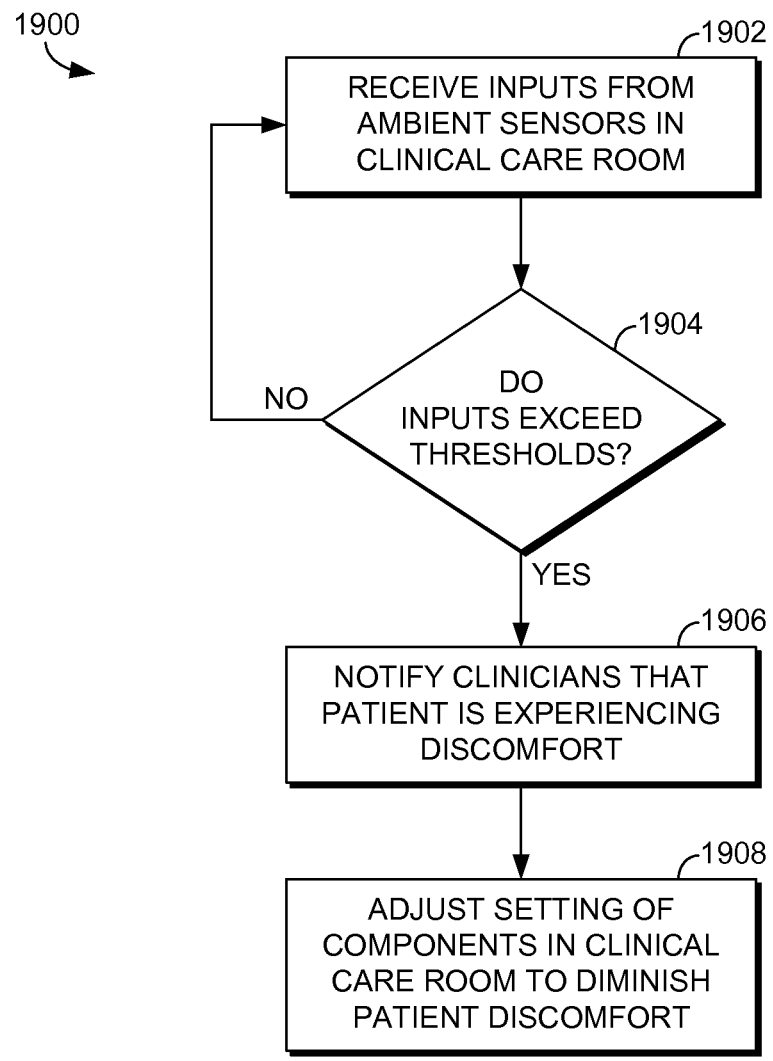
FIG. 19 depicts a flow diagram illustrating an exemplary method of minimizing patient discomfort according to an embodiment of the current invention.

Turning now to FIG. 19, a flow diagram is depicted illustrating a method 1900 of minimizing patient discomfort. At a step 1902, one or more inputs are received from ambient sensors located throughout a clinical care room. The inputs are received by various interfaces that are part of a smart room service such as the smart room service 302 of FIG. 3. The interfaces may include, for example, a sensor interface, a bed interface, and a medical device interface.

The ambient sensors may include a camera for monitoring facial expressions indicating discomfort. In one embodiment, the camera is a web camera. In another embodiment, the camera is a depth camera. In addition to monitoring facial expressions, depth cameras may monitor the location, position, identity, and movement of people in the clinical care room. Audio sensors are used to monitor patient articulations that indicate discomfort, and vital signs monitors detect alterations in heart rate and respiratory rate that may indicate discomfort. Moisture sensors and weight sensors incorporated into the patient's bed are used to detect increased perspiration and movement patterns that may indicate discomfort. Additionally, a RTLS system may be used to triangulate a location of the patient (i.e., identify whether the patient has fallen and is lying on the floor).

At a step 1904, a determination is made whether the inputs from the ambient sensors exceed predetermined or preset thresholds. This determination may be made by the bed interface, the sensor interface, and/or the medical device interface. In one aspect, the threshold values are derived using data from the general population as a whole, or, in another aspect, the predetermined thresholds are derived from baseline values stored in association with the patient's electronic medical record. Further, the thresholds may be set by a clinician. A determination that the patient is experiencing discomfort may be based on one input, a combination of inputs, or all the inputs exceeding respective predetermined thresholds. If an input exceeds a predetermined threshold, the bed interface, the sensor interface, and/or the medical device interface are further configured to determine a severity level of discomfort based on the degree of variance between the received input and the threshold—the higher the degree of variance, the greater the severity level.

If, at step 1904, it is determined that the inputs do not exceed the respective predetermined thresholds, the method 1900 reverts back to step 1902, and the patient continues to be monitored by the ambient sensors. However, if it is determined at step 1904 that one, a combination, or all of the inputs exceed the respective predetermined thresholds, then, at a step 1906, clinicians are notified that the patient is experiencing discomfort.

Clinicians may receive notifications from pagers, mobile devices, and/or badges worn by the clinicians. The notifications are made by a communication component of the smart room service. The notification is placed in a message queue and is placed higher in the queue based on the severity level of the discomfort. The notification provides information such as the name of the patient, a room number, and a severity level of the discomfort. Notifications may also be sent to a clinician work center. Further, a communication portal between the clinicians and the patient may automatically be initiated. Notifications may also be sent to the patient's family members if it is determined that the family members are present in the hospital but are currently not located in the patient's room. Further, a message may be displayed on a digital room sign located outside of the clinical care room notifying clinicians, family members, and the friends that the patient is experiencing discomfort and needs assistance.

At a step 1908, settings of components in the clinical care room are automatically adjusted to assist in diminishing the patient's discomfort. For instance, aromatherapy may be initiated as well as audio and visual relaxation therapies. The therapies are pre-selected by the patient upon admission to the healthcare facility utilizing a patient interactive station. Medical device settings may also be adjusted to help alleviate patient discomfort. For instance, a PCA pump may automatically administer pain relief after authorization and verification is received from a clinician. Alternatively, pain relief may be administered without authorization and verification from a clinician as long as appropriate patient safety measures are in place (frequent monitoring by a clinician, frequent vital signs monitoring, etc.) and other preset parameters are met. The preset parameters may include patient vital signs within a specified range, dosing intervals, and dosage amounts. The technology supplier, device manufacturer, healthcare facility, and/or state or federal regulations may govern whether pain relief is administered with or without clinician verification and authorization and what measures are needed to ensure patient safety.

Figure 20:
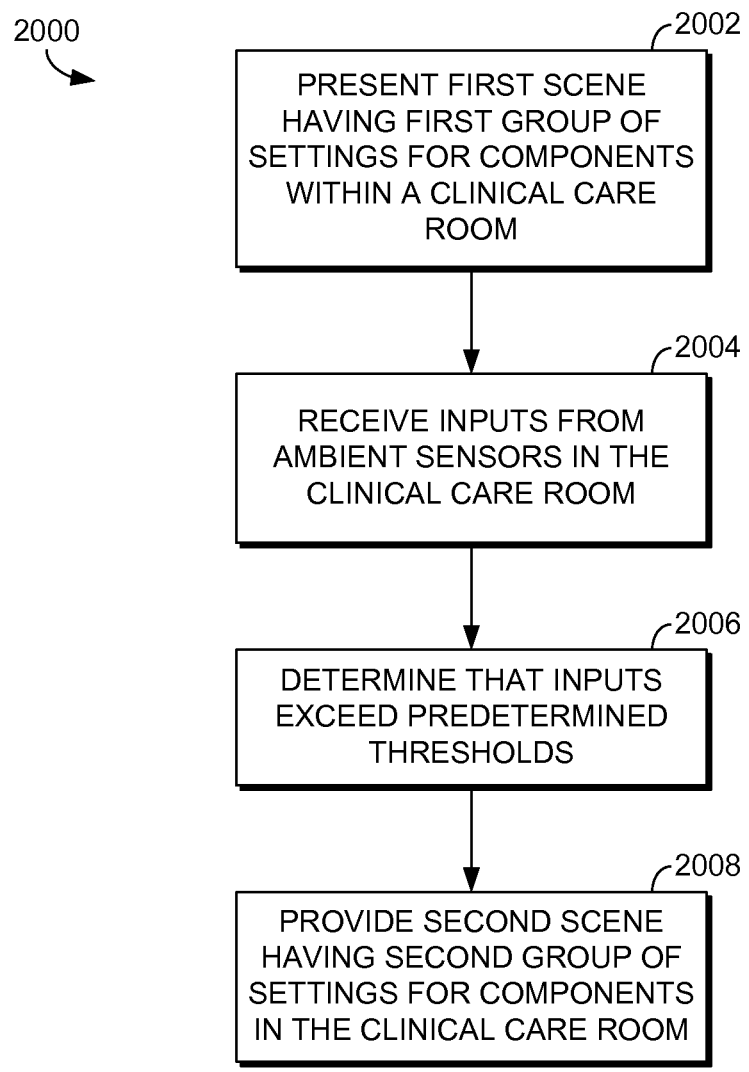
FIG. 20 depicts a flow diagram illustrating an exemplary method of transitioning a clinical care room from a first scene to a second scene in order to facilitate pain management according to an embodiment of the current invention.

Turning now to FIG. 20, FIG. 20 depicts another exemplary method 2000 of managing patient pain. At a step 2002, a first scene is presented in a clinical care room. The first scene is associated with a first group of settings for components within one or more zones of the clinical care room. The zones include a patient zone, a family/friend zone, and a caregiver zone as shown in FIG. 2. The first scene may be any of the scenes described above—a sleep scene, a relaxation scene, a medication administration scene, and the like.

At a step 2004, inputs are received from ambient sensors located throughout the clinical care room. At a step 2006, a determination is made that the received inputs exceed respective predetermined thresholds. Based on this, a determination is made that the patient is experiencing pain or discomfort. To facilitate management of the patient's pain, at a step 2008, a second scene is provided. The second scene has a second group of setting for the components in the clinical care room. As discussed above, the second scene may include aromatherapy, visual relaxation therapy, audio relaxation therapy, attention from clinicians and family members, and/or automatic administration of pain relief (with appropriate safety measures in place). After receiving an indication from the patient, family member, friend, or clinician that the patient's pain is under control, the first scene in the clinical care room is automatically provided.

The present invention is designed to detect patient discomfort at an early stage using ambient sensors in a clinical care room. Various intervention strategies are automatically initiated upon determining that the patient is experiencing discomfort; these strategies are designed to diminish or alleviate the patient's discomfort.

Management of Patient Fall Risk

An embodiment of the present invention uses fall risk sensors to detect potential or actual patient falls and to initiate intervention strategies designed to reduce the risk of falls and/or to minimize the effect of falls. This embodiment may be described throughout the present specification as a fall risk management scene or process.

Figure 21:
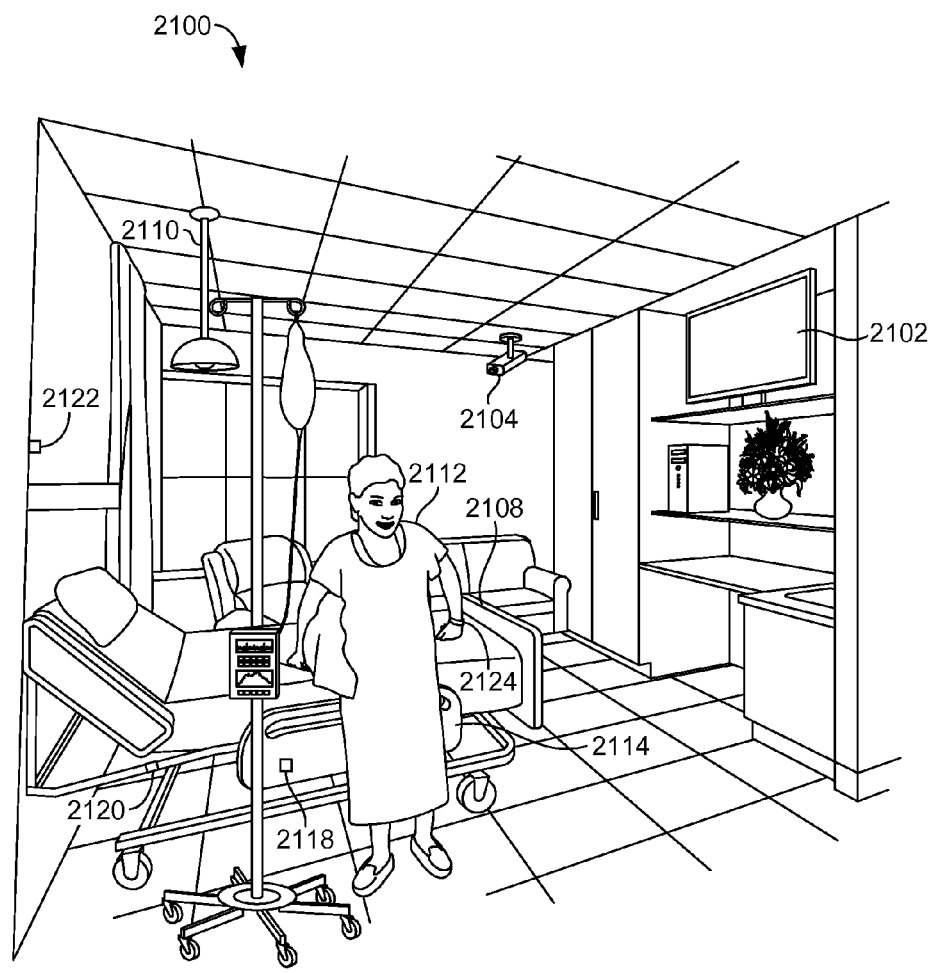
FIG. 21 depicts an exemplary scene illustrating the use of fall risk sensors to detect potential fall risk in accordance with an embodiment of the current invention.

The fall risk management scene is triggered upon receiving inputs from fall risk sensors located in a clinical care room that indicate that the patient is currently at risk for falling. FIG. 21 depicts a fall risk management scene 2100, in accordance with an embodiment of the present invention. FIG. 21 depicts a number of fall risk sensors used to detect potential fall risk scenarios. The fall risk sensors include a camera 2104, weight sensors 2120 and guard rail sensors 2118 associated with the patient's bed 2108, and an real-time-location-system (RTLS) that includes one or more sensors 2122 and an radio-frequency identification (RFID) tag 2124 worn by the patient 2112.

In one aspect, the camera 2104 may comprise a Web camera, a digital camera, a depth camera, and the like. There may be a single camera 2104 or multiple cameras 2104. Further, if there are multiple cameras, each camera may be positioned differently from the other cameras, and each camera may serve a unique purpose. Any and all such variations, or any combination thereof, are within the scope of embodiments of the present invention.

The camera 2104 may be used to monitor a location and position of the patient 2112 and any movement associated with the patient 2112. As such, the camera 2104 may be positioned on the ceiling of the room over the patient's bed 2108. Other cameras 2104 may be positioned at other locations in the room to monitor family members and friends located in a family/friend zone such as the family/friend zone 202 of FIG. 2.

The camera 2104 may be programmed to monitor the location, position, and movement of the patient 2112 upon determining that the patient 2112 has been classified or flagged as being a fall risk. Some exemplary patient groups that are classified as being at risk for falls include those patients with balance disorders, dementia, orthopedic problems, advanced age, frailty, and the like. The classification of a patient as being a fall risk often occurs at the time the patient is admitted to the healthcare facility but may be made any time during the patient's hospital stay. The classification of a patient as a fall risk is stored in association with the patient's electronic medical record (EMR).

Upon determining that the patient 2112 is classified as being a fall risk, the camera 2104 may be programmed to capture images of the patient 2112 at preset intervals (i.e., every five minutes, every ten minutes, etc.). Alternatively, the camera 2104 may be triggered to monitor the location, position, and movement of the patient 2112 upon receiving an indication from one of the other fall risk sensors. For example, the weight sensors 2120 associated with the patient's bed 2108 may sense that the patient is no longer in the bed or that the patient's weight has shifted close to the edge of the bed 2108. Additionally, the guard rail sensors 2118 may determine that one or both of the bed's guard rails 2114 are in a lowered position. This information is communicated to a connectivity engine (via a bed or sensor inter-face), which, in turn, triggers some or all of the cameras 2104 to capture images from different parts of the room in order to localize the patient 2112. Depth cameras are especially suited for this type of monitoring. Depth cameras, also known as a range camera, a 3D camera, a time-of-flight camera, and/or a RGB-D camera, transmit near-infrared light and measure its "time-of-flight" after it reflects off objects.

The location, position, and movement data captured by the camera 2104 is transmitted to the sensor interface, which processes the data to render three-dimensional images. The camera 2104 is able to distinguish human body parts, joints, and movements. As such, the camera 2104 may be used to determine whether the patient 2112 is agitated (increased body movements), whether the patient 2112 is in imminent danger of falling (unsteady gait, positioned near the edge of the bed with no guard rails up), or whether the patient 2112 has fallen (patient lying on the floor of the room). Further, the camera 2104 may be used to distinguish the patient's location and movements from other people present in the room.

As mentioned, the fall risk sensors also include the weight sensors 2120 and the guard rail sensors 2118 associated with the patient's bed 2108. The weight sensors 2120 detect fluctuations in the patient's weight over different parts of the bed 2108. The weight sensors 2120 may, for example, detect that the patient 2112 is absent from the bed 2108 or that the patient's weight is distributed close to the edge of the bed 2108. The guard rail sensors 2118 detect whether one or both of the guard rails 2114 are in an up position, a down position, or an intermediate position.

Fall risk sensors may further comprise the RTLS that includes the sensor 2122 and the RFID tag 2124 worn by the patient 2112. Although only one sensor 2122 is shown, multiple sensors may be located throughout the clinical care room. As outlined above, RTLS utilizes the sensors 2122 to detect the RFID tag 2124 worn by the patient 2112 in order to determine a location and identity of the patient 2112. In one aspect, the sensors 2122 triangulate the RFID tag 2124 to determine if the patient 2112 is located on the floor of the room or is in danger of falling off the bed.

Inputs from the fall risk sensors that may indicate that the patient 2112 is at risk for falling or has fallen include the patient's weight being disproportionately positioned towards the edge of the bed 2108 or the absence of the patient 2112 from the bed 2108, one or both of the guard rails 2114 being in a down position, camera images indicating that the patient 2112 is attempting to leave the bed or has fallen, RTLS information indicating that the patient 2112 is not in the bed 2108 or is located on the floor of the room, and the like. Any and all such variations, and any combination thereof, are contemplated as being within the scope of the invention.

The clinical care room may also include a display device 2102. The display device 2102, in one aspect, may include a television located within viewing distance of the patient 2112. The display device 2102 may also include a monitor associated with the bed 2108, a patient interactive station, a tablet PC, and/or a smart phone associated with the patient 2112. The clinical care room may further include one or more lights 2110 which may be automatically adjusted upon determining that the patient 2112 is currently at risk for a fall.

Once it is determined, based on inputs received from the fall risk sensors that the patient is currently at risk for falling or has fallen, various actions are automatically initiated by the smart room service. A communication component of the smart room service (such as the communication component 324 of FIG. 3) communicates a message indicating the patient's fall risk to a message queue of a device associated with a clinician; the device may include a smart phone, a tablet, a personal computer, and the like. The fall risk message may be classified as a critical alert and be moved up in the message priority queue. A message indicating the patient's fall risk may also be displayed on a digital room sign located outside the entrance to the clinical care room. For instance, the sensor interface communicates data indicating the patient's current fall risk to an interactive room link component of the smart room service, such as the interactive room link component 318 of FIG. 3. In turn, the interactive room link component displays a message on the digital room sign. Further, the communication component may automatically establish a communication portal between the patient's room and a clinician and/or a clinician work center allowing two-way communication between the patient 2112 and clinicians.

Figure 23:
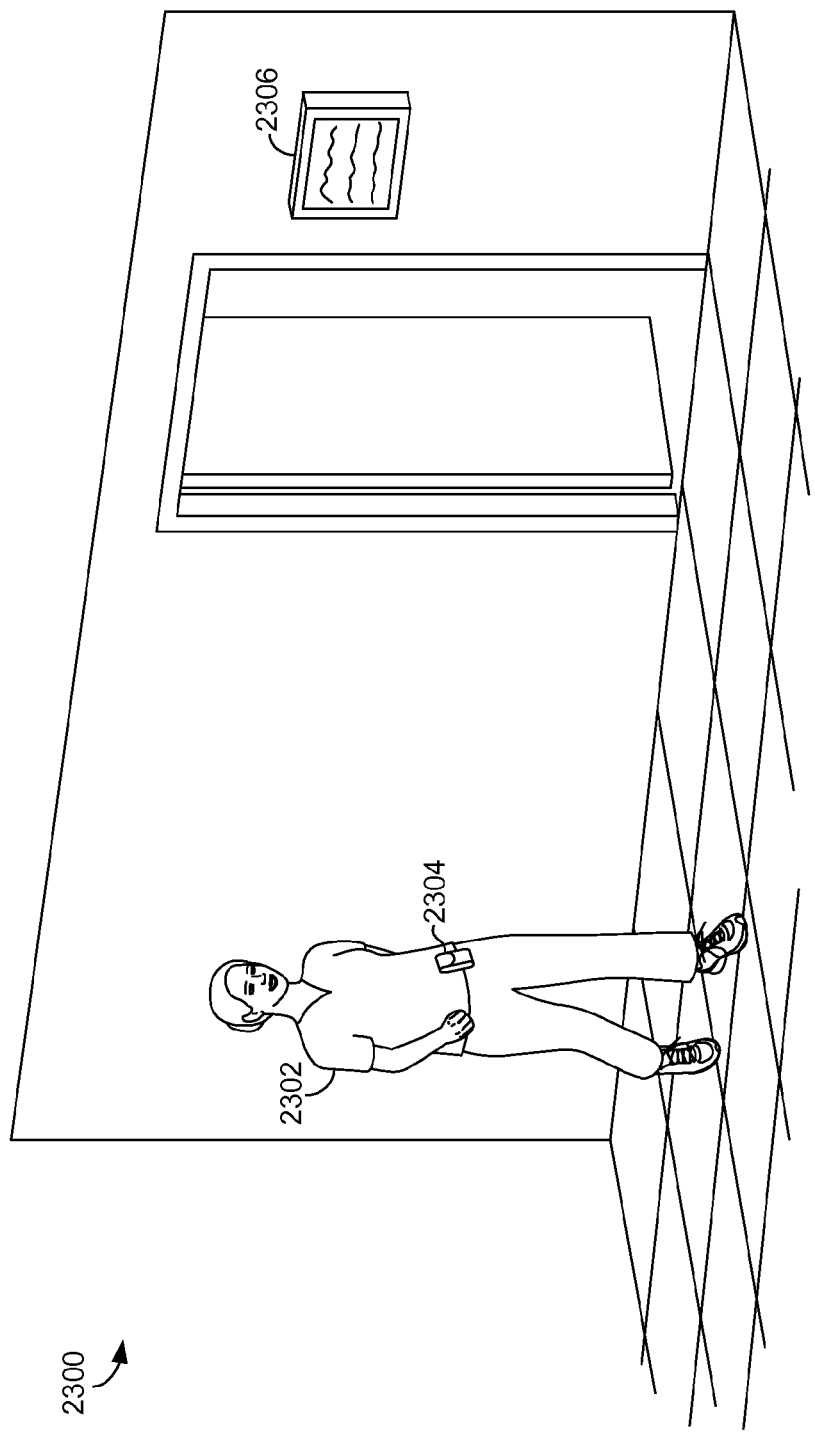
FIG. 23 depicts an exemplary scene illustrating alerts and notifications indicating that a patient is currently at risk for falling in accordance with an embodiment of the present invention.

FIG. 23 depicts an exemplary scene 2300 illustrating various notifications and alerts indicating that the patient is currently at risk for a fall. A clinician 2302 receives a notification via a device 2304. The notification may include patient identifying information, a room number, and a message indicating that the patient is currently at risk for a fall. A digital room sign 2306 displays a message indicating that the patient is currently at risk for a fall.

Other actions designed to decrease or manage the patient's current fall risk are also automatically initiated upon determining that the patient is at risk for a fall or has fallen. These include adjusting the lighting in the clinical care room (e.g., such as the light 2110 of FIG. 21) to facilitate management of the fall risk. For example, if the room is dark, the lighting may be adjusted to illuminate the room. This helps not only the patient but also those clinicians coming to assist the patient. A message may be presented on a display device such as the display device 2102 of FIG. 21. The message may include both visual and auditory components. For instance, a message may be displayed informing the patient that a clinician will be arriving shortly to assist the patient and for the patient to stay in bed or to stay still. The displayed message may be accompanied by an auditory soundtrack that details the same or similar information. Guard rails may be automatically raised upon determining that the patient is not obstructing the guard rails. Any and all such aspects, and any combination thereof, are contemplated as being within the scope of the invention.

Figure 22:
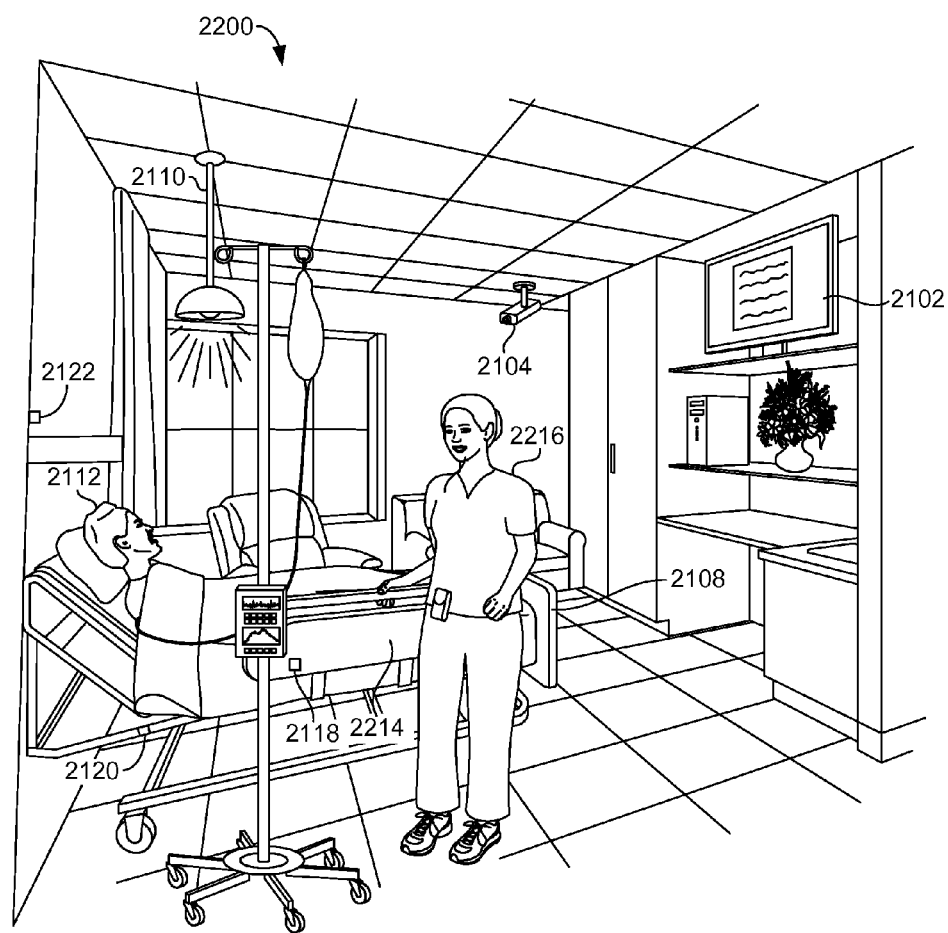
FIG. 22 depicts an exemplary scene illustrating the management of a patient's fall risk in accordance with an embodiment of the present invention.

FIG. 22 depicts a fall risk management scene 2200 where one or more actions have automatically been initiated upon determining that patient 2112 is currently at risk for a fall. The fall risk management scene 2200 represents the fall risk management scene 2100 at a later point in time. As such, like numbering is used for like elements between FIG. 21 and FIG. 22. The fall risk management scene 2200 includes the display device 2102 that is presenting a message informing the patient to stay in bed or to stay still, and that help will be arriving shortly. In one aspect, if the display device 2102 is powered off, the display device 2102 is automatically powered on and the message is presented. In another aspect, if the display device 2102 is currently presenting content, the message may appear as a pop-up or overlay on the existing content.

The fall risk management scene 2200 further indicates that that the light 2110 is fully illuminated to assist the patient 2112 and any clinicians in their actions. A clinician 2216 has arrived after being notified that the patient 2112 is experiencing a fall risk and is properly positioning the patient 2112 on the bed 2108. The guard rails 2114 have been raised either automatically upon determining that the patient is currently at risk for falling and is not obstructing the guard rails 2114, or manually by the clinician 2216.

Once the patient's fall risk has been successfully managed by, for example, repositioning the patient 2112 on the bed 2108 and placing the guard rails 2114 in the proper position, the clinician 2216 may manually indicate such success by interacting with, for example, a clinician-dashboard display device. Upon receiving the indication of a successful intervention, the smart room service may readjust the room settings such as illumination, televisions settings, and the like to approximate the settings present before the fall risk management scene was initiated. This would not include lowering the guard rails 2114.

Figure 24:
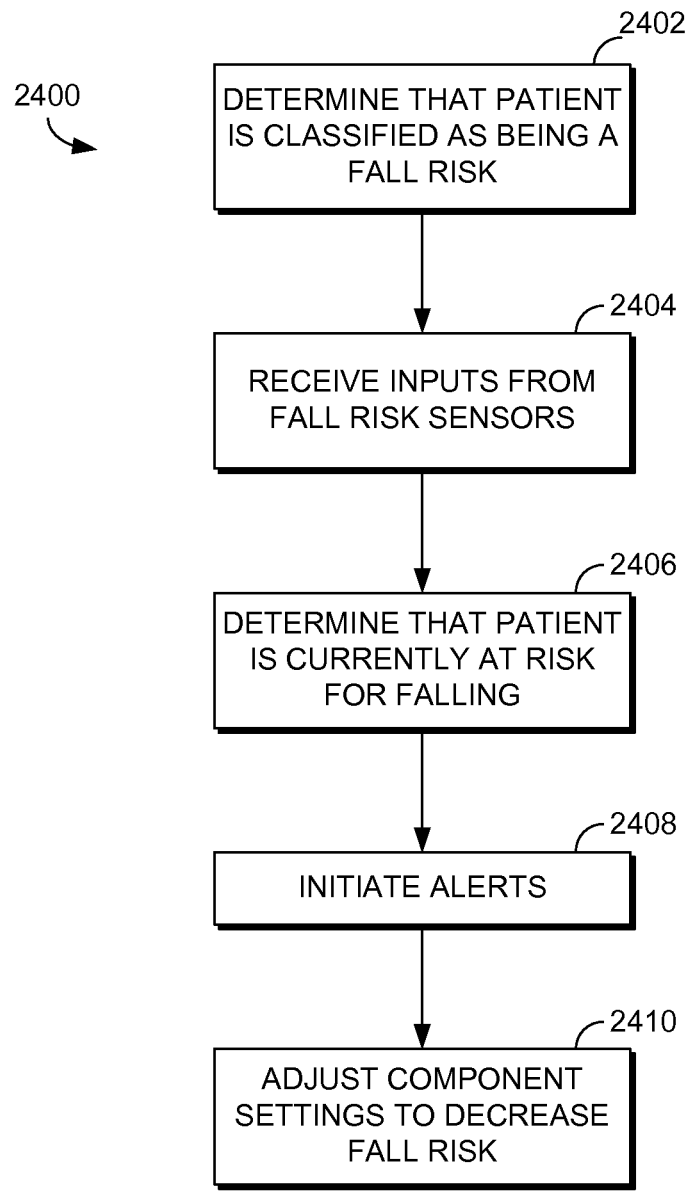
FIG. 24 depicts a flow diagram of an exemplary method of managing fall risk for a patient in a clinical care room in accordance with an embodiment of the present invention.

Turning now to FIG. 24, a flow diagram is depicted illustrating a method 2400 of managing a patient's fall risk. At a step 2402, it is determined that the patient has previously been classified or flagged as a fall risk. Classifying a patient as a fall risk may be manually performed by a clinician upon admission of the patient to the healthcare facility or during the patient's stay at the healthcare facility. It also may be done automatically by, for example, a patient management system that utilizes information from the patient's EMR in combination with standardized guidelines to determine if the patient should be classified as a fall risk. Information concerning the classification of the patient as a fall risk is stored in association with the patient's EMR. Thus, to determine if the patient has previously been classified as a fall risk, the patient's EMR is accessed and an indication that the patient has been classified as a fall risk is identified. The classification of the patient as being a fall risk may automatically initiate monitoring the patient using, for example, fall risk sensors.

At a step 2404, inputs are automatically received from fall risk sensors located in a clinical care room. The inputs are received by various interfaces that are part of a smart room service such as the smart room service 302 of FIG. 3. The interfaces may include, for example, a sensor interface, a bed interface, and a medical device interface.

The fall risk sensors may include weight and guard rail sensors associated with the patient's bed (e.g., the weight sensors 2120 and the guard rails sensors 2118 of FIGS. 21 and 22), patient location information from a real-time-location-service (e.g., the sensor 2122 and the RFID tag 2124 of FIG. 21), and location information provided by a depth camera such as the depth camera 2104 of FIG. 21. As mentioned above, the depth camera is used to monitor the location, movement, and/or position of the patient upon determining that the patient has been classified as a fall risk. The depth camera may capture patient images at preset intervals or upon receiving an indication from one or more of the other fall risk sensors that the patient is at risk for falling.

At a step 2406, using inputs received from the fall risk sensors, it is determined that the patient is currently at risk for falling. Some exemplary inputs that indicate that the patient is at risk for falling include inputs from weight sensors indicating that the patient's weight is concentrated at the edge of the bed or is distributed in one location at the edge of the bed (e.g., the patient is attempting to sit at the edge of the bed), inputs from guard rail sensors indicating that one or both of the guard rails are in a lowered positions, inputs from a depth camera indicating that the patient's location and/or position is near the edge of the bed or is on the floor, inputs from an RTLS system indicating that the patient is located on the floor, and the like.

At a step 2408, one or more alerts are automatically initiated. The alerts may comprise critical alerts that are automatically communicated to devices associated with members of the patient's care team (e.g., the patient's primary and secondary caregivers, the charge nurse, and the like). The alerts may include patient identifying information, room location, and a message indicating that the patient is currently at risk for falling or has fallen. The alerts may also comprise a notification that is displayed on a digital room sign located outside the entrance to the patient's room. The notification may comprise a message that the patient is currently at risk for a fall and that assistance is needed.

At a step 2410, settings for component in the clinical care room are adjusted so that the patient's fall risk is decreased. For example, room illumination may be increased, guard rails may be automatically raised, and a message may be displayed on a patient display device. The message may indicate that help will be arriving shortly and that the patient should remain in bed or remain where they are located. In one aspect, a communication portal may be initiated between the patient's room and a clinician or clinician work center. The communication portal allows the clinician to communicate with the patient while help is in route to the patient's room.

In one aspect, the alerts and/or actions are not initiated until it is determined that a clinician is not already located in the patient's room. For instance, a clinician may be assisting the patient out of the bed. In such a situation, a fall risk management scene would not be initiated even though fall risk sensors may be activated. A clinician's presence in the patient's room may be determined by using, for example, an RTLS system as explained above.

Figure 25:
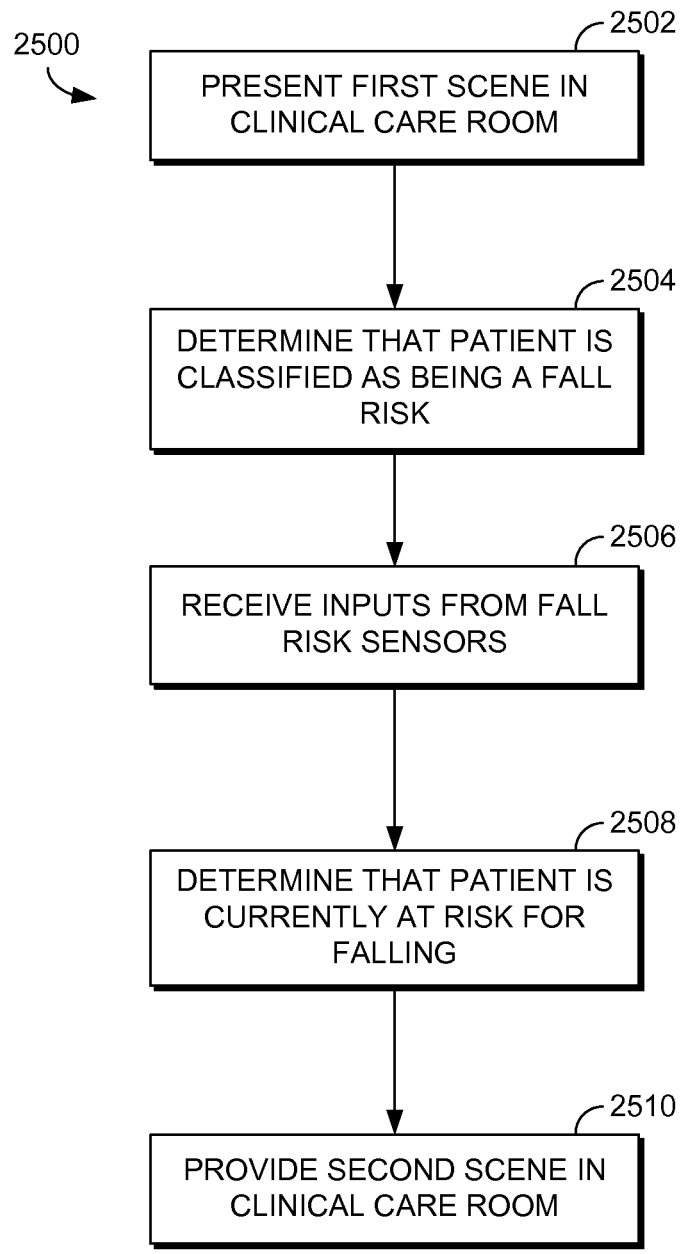
FIG. 25 depicts a flow diagram of an exemplary method for transitioning a clinical care room from a first scene to a second scene in order to facilitate management of a patient's fall risk in accordance with an embodiment of the present invention.

Turning now to FIG. 25, a flow diagram is depicted of an exemplary method 2500 for transitioning a clinical care room from a first scene to a second scene in order to facilitate management of a patient's fall risk. At a step 2502, a first scene is presented in a clinical care room. The first scene is associated with a first group of settings for components within one or more zones of the clinical care room. The zones include a patient zone, a family/friend zone, and a caregiver zone as shown in FIG. 2. Components within the zones may include a patient interactive station component, an interactive room link component, a connectivity engine, a sensor interface, a communication component, a bed interface, a medical device interface, and the like. These components were discussed above with respect to FIG. 2. The first scene may be any of the scenes described above—a sleep scene, a relaxation scene, a medication administration scene, an ambient sensing of patient discomfort scene, and the like.

At a step 2504, it is determined that the patient has previously been classified as a fall risk. This information may be stored in association with the patient's EMR such as the EMR 304 of FIG. 3. At a step 2506, inputs are automatically received from fall risk sensors located throughout the clinical care room. As mentioned, fall risk sensors include location sensors such as depth cameras, weight sensors and guard rail sensors associated with a patient bed, RTLS sensors, and the like. At a step 2508, based on the inputs from the fall risk sensors, it is determined that the patient is currently at risk for falling.

At a step 2510, to facilitate the management of the patient's fall risk, a second scene is provided in the clinical care room. The second scene is associated with a second group of settings for the components within the zones of the clinical care room. The second group of settings may be different from the first group of settings. As well, the second group of settings is optimized to facilitate management of the patient's fall risk. The second group of settings may include, for example, displaying a message indicating that the patient is currently at risk for a fall on a digital room sign located outside the entrance to the patient's room, adjusting lights in the clinical care room to facilitate management of the fall risk, automatically raising guard rails on the patient's bed, alerting members of the patient's care team that the patient is currently at risk for falling, and presenting a message on a patient display device informing the patient to stay in bed or to stay still and that help will be arriving shortly.

Figure 26:
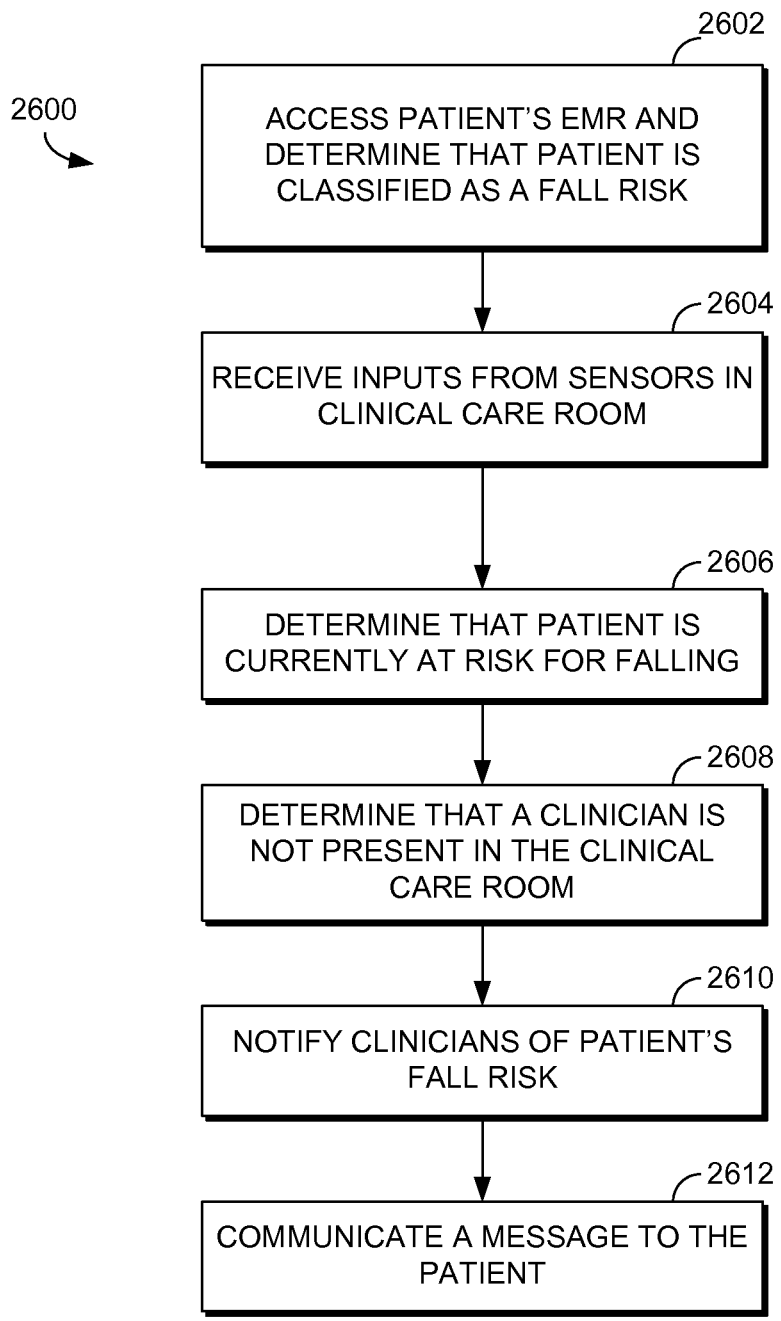
FIG. 26 depicts a flow diagram of an exemplary method for managing a patient's fall risk using fall risk sensors in accordance with an embodiment of the present invention.

FIG. 26 depicts a flow diagram of an exemplary method 2600 for managing fall risk for a patient in a clinical care room. At a step 2602, the patient's EMR is accessed, and it is determined that the patient has been classified as a fall risk. At a step 2604, inputs are received from fall risk sensors in the clinical care room. The sensors include at least weight and guard rails sensors associated with the patient's bed, and location sensors such as depth cameras.

At a step 2606, based on the inputs received from the fall risk sensors, it is determined that the patient is currently at risk for falling, and, at a step 2608 it is determined that a clinician is not present in the clinical care room. An RTLS system may be used to determine that a clinician is not present in the clinical care room. At a step 2610, clinicians are notified that the patient is currently at risk for falling. Notification may occur through pushing an alert to devices associated with members of the patient's care team. In one aspect, the alert may be a critical alert that supersedes existing patient alerts. At a step 2612, a message is communicated to the patient via, for example, a display device in the clinical care room. The display device may include a television, a patient interactive station, a smart phone, a tablet PC, and the like. The message may inform the patient that help is on the way and to remain still.

The present invention is designed to facilitate the management of a patient's fall risk by utilizing fall risk sensors in the clinical care room. The fall risk sensors monitor the patient and automatically initiate intervention strategies upon detection that the patient is currently at risk for falling. The intervention strategies are designed to reduce or eliminate the fall risk.

The present invention has been described in relation to particular embodiments, which are intended in all respects to be illustrative rather than restrictive. Further, the present invention is not limited to these embodiments, but variations and modifications may be made without departing from the scope of the present invention.

The invention claimed is:

1. A computerized method carried out by one or more computing devices having one or more processors that performs a method of automatically and without human intervention monitoring an intravenous (IV) infusion of a medication to a patient in a clinical care room, the method comprising:
   identifying an order for the medication to be administrated to the patient by an IV infusion pump;
   automatically modifying at least two physical components within the clinical care room assigned to the patient based on the order for the medication, each of the at least two physical components being modified from a first setting to a second setting;
   automatically and without human intervention monitoring, via one or more monitoring devices in the clinical care room, one or more patient parameters associated with the patient in the clinical care room while the medication is being administered via the IV infusion pump;

determining, using the one or more processors, that there is a change in at least one of the one or more patient parameters that exceeds a predefined threshold; and automatically and without human intervention adjusting settings associated with the IV infusion pump.

2. The method of claim 1, wherein the one or more monitoring devices comprises at least a vital signs monitor.

3. The method of claim 2, wherein the one or more patient parameters comprises the patient's heart rate and the patient's blood pressure.

4. The method of claim 2, wherein adjusting the settings associated with the IV infusion pump comprises slowing an infusion rate of the IV infusion pump.

5. The method of claim 1, further comprising communicating an alert to one or more of the patient's caregivers.

6. The method of claim 1, wherein the one or more monitoring devices comprise at least a moisture sensor on a bed associated with the patient in the clinical care room, and wherein the one or more patient parameters comprise the patient sweating, and wherein altering the settings associated with the IV infusion pump comprise slowing an infusion rate of the IV infusion pump.

7. The method of claim 1, wherein automatically adjusting settings associated with the IV infusion pump comprises automatically stopping administration of the medication to the patient, and wherein the method further comprise, automatically modifying the at least two physical component within the clinical care room to return each physical component to the first setting.

8. One or more non-transitory computer-readable media having embodied thereon computer-executable instructions that, when executed by a computing device, cause the computing device to perform a method of automatically and without human intervention monitoring an intravenous (IV) infusion of a medication to a patient in a clinical care room, the method comprising:

identifying an order for the medication to be administrated to the patient by an IV infusion pump;

automatically modifying at least two physical components within the clinical care room assigned to the patient based on the order for the medication, each of the at least two physical components being modified from a first setting to a second setting;

automatically and without human intervention monitoring, via one or more monitoring devices in the clinical care room, one or more patient parameters associated with the patient in the clinical care room while the medication is being administered via the IV infusion pump;

determining, using the one or more processors, that there is a change in at least one of the one or more patient parameters that exceeds a predefined threshold; and automatically and without human intervention adjusting settings associated with the IV infusion pump.

9. The computer-readable media of claim 8, wherein the one or more monitoring devices comprises at least a vital signs monitor.

10. The computer-readable media of claim 9, wherein the one or more patient parameters comprises the patient's heart rate and the patient's blood pressure.

11. The computer-readable media of claim 9, wherein adjusting the settings associated with the IV infusion pump comprises slowing an infusion rate of the IV infusion pump.

12. The computer-readable media of claim 8, wherein the method further comprises communicating an alert to one or more of the patient's caregivers.

13. The computer-readable medium of claim 8, wherein the one or more monitoring devices comprise at least a moisture sensor on a bed associated with the patient in the clinical care room, and wherein the one or more patient parameters comprise the patient sweating, and wherein altering the settings associated with the IV infusion pump comprise slowing an infusion rate of the IV infusion pump.

14. A system for automatically and without human intervention monitoring an intravenous (IV) infusion of a medication to a patient in a clinical care rooms, the system comprising:

a computing device associated with the clinical care room, the computing device having one or more processors and one or more computer-readable media; one or more monitoring devices in the clinical care room communicatively coupled to the computing device; and a data store communicatively coupled with the computing device; wherein the computing device:

identifies an order for the medication to be administrated to the patient by an IV infusion pump;

automatically modifies at least two physical components within the clinical care room assigned to the patient based on the order for the medication, each of the at least two physical components being modified from a first setting to a second setting;

automatically and without human intervention monitors, receives one or more patient parameters associated with the patient in the clinical care room via the one or more monitoring devices, the one or more patient parameters being received while the medication is being administered via the IV infusion pump;

determines that there is a change in at least one of the one or more patient parameters that exceeds a predefined threshold; and automatically and without human intervention adjusts settings associated with the IV infusion pump.

15. The system of claim 14, wherein the one or more monitoring devices comprises at least a vital signs monitor.

16. The system of claim 15, wherein the one or more patient parameters comprises the patient's heart rate and the patient's blood pressure.

17. The system of claim 15, wherein adjusting the settings associated with the IV infusion pump comprises slowing an infusion rate of the IV infusion pump.

18. The system of claim 14, wherein the computing device further communicates an alert to one or more of the patient's caregivers.

19. The system of claim 14, wherein the one or more monitoring devices comprise at least a moisture sensor on a bed associated with the patient in the clinical care room, and wherein the one or more patient parameters comprise the patient sweating, and wherein altering the settings associated with the IV infusion pump comprise slowing an infusion rate of the IV infusion pump.

* * * * *

UNITED STATES PATENT AND TRADEMARK OFFICE
CERTIFICATE OF CORRECTION

PATENT NO. : 10,220,142 B2
APPLICATION NO. : 14/529432
DATED : March 5, 2019
INVENTOR(S) : Stephanie Palmer Bechtel et al.

Page 1 of 1

It is certified that error appears in the above-identified patent and that said Letters Patent is hereby corrected as shown below:

In the Claims

Column 45, Line 25: Please remove "comprise" and replace with --comprises--.

Column 46, Line 07: Please remove "medium" and replace with --media--.

Column 46, Line 14: Please remove "comprise" and replace with --comprises--.

Column 46, Line 62: Please remove "comprise" and replace with --comprises--.

Signed and Sealed this
Twenty-third Day of April, 2019

Andrei Iancu
*Director of the United States Patent and Trademark Office*